US011590214B2

(12) United States Patent
Hadrup et al.

(10) Patent No.: US 11,590,214 B2
(45) Date of Patent: Feb. 28, 2023

(54) ANTIGEN PRESENTING SCAFFOLDS FOR IMMUNE-CELL MANIPULATION

(71) Applicant: Danmarks Tekniske Universitet, Kgs. Lyngby (DK)

(72) Inventors: Sine Reker Hadrup, Virum (DK); Vibeke Mindahl Rafa, Copenhagen S (DK); Søren Nyboe Jakobsen, Charlottenlund (DK)

(73) Assignee: Danmarks Tekniskte Universitet, Kgs. Lyngby (DK)

( * ) Notice: Subject to any disclaimer, the term of this patent is extended or adjusted under 35 U.S.C. 154(b) by 411 days.

(21) Appl. No.: 16/470,503

(22) PCT Filed: Dec. 20, 2017

(86) PCT No.: PCT/EP2017/083862
§ 371 (c)(1),
(2) Date: Jun. 17, 2019

(87) PCT Pub. No.: WO2018/115146
PCT Pub. Date: Jun. 28, 2018

(65) Prior Publication Data
US 2019/0316069 A1 Oct. 17, 2019

(30) Foreign Application Priority Data
Dec. 21, 2016 (EP) .................................. 16205918

(51) Int. Cl.
*C12M 1/12* (2006.01)
*A61K 35/17* (2015.01)
(Continued)

(52) U.S. Cl.
CPC .......... *A61K 39/0011* (2013.01); *A61K 35/17* (2013.01); *A61K 39/001104* (2018.08);
(Continued)

(58) Field of Classification Search
None
See application file for complete search history.

(56) References Cited

U.S. PATENT DOCUMENTS 10,435,668 B2 * 10/2019 Schneck ................. A61P 43/00
2011/0318380 A1 12/2011 Brix et al.
(Continued)

FOREIGN PATENT DOCUMENTS

EP 1470821 A2 10/2004
EP 1377609 B1 6/2015
(Continued)

OTHER PUBLICATIONS

Yu Xia et a. (Asian Pacific Journal of Tropical Medicine, 2013, p. 467-472).*
(Continued)

*Primary Examiner* — Agnieszka Boesen
(74) *Attorney, Agent, or Firm* — Knobbe, Martens, Olson & Bear, LLP

(57) ABSTRACT

The present invention relates to artificial antigen presenting cell (aAPC) scaffolds to provide cells with specific functional stimulation to obtain phenotypic and functional properties ideal to mediate tumor regression or viral clearance. In particular, the scaffolds of the present invention comprise antigens, such as peptide-MHC (pMHC) class I molecules, and specific combinations of cytokines and co-stimulatory molecules to allow effective expansion and functional stimulation of specific T cells.

18 Claims, 29 Drawing Sheets
Specification includes a Sequence Listing.

(51) Int. Cl.

| | | |
|---|---|---|
| *C12N 5/0783* | (2010.01) | |
| *A61K 39/00* | (2006.01) | |
| *A61P 31/22* | (2006.01) | |
| *A61P 31/16* | (2006.01) | |
| *A61P 35/00* | (2006.01) | |
| *A61K 39/12* | (2006.01) | |
| *A61K 39/145* | (2006.01) | |
| *A61K 39/245* | (2006.01) | |
| *C12N 7/00* | (2006.01) | |

(52) U.S. Cl.
CPC .......... *A61K 39/001106* (2018.08); *A61K 39/001112* (2018.08); *A61K 39/001113* (2018.08); *A61K 39/001114* (2018.08); *A61K 39/001124* (2018.08); *A61K 39/001168* (2018.08); *A61K 39/001182* (2018.08); *A61K 39/001195* (2018.08); *A61K 39/12* (2013.01); *A61K 39/145* (2013.01); *A61K 39/245* (2013.01); *A61P 31/16* (2018.01); *A61P 31/22* (2018.01); *A61P 35/00* (2018.01); *C12M 25/14* (2013.01); *C12N 5/0636* (2013.01); *C12N 7/00* (2013.01); *A61K 2039/5154* (2013.01); *A61K 2039/5158* (2013.01); *A61K 2039/55527* (2013.01); *A61K 2039/55533* (2013.01); *A61K 2039/605* (2013.01); *A61K 2039/6087* (2013.01); *A61K 2039/645* (2013.01); *C12N 2501/2302* (2013.01); *C12N 2501/2315* (2013.01); *C12N 2501/2321* (2013.01); *C12N 2501/50* (2013.01); *C12N 2533/70* (2013.01); *C12N 2710/16134* (2013.01); *C12N 2710/16234* (2013.01); *C12N 2760/16034* (2013.01)

(56) References Cited

U.S. PATENT DOCUMENTS

| | | |
|---|---|---|
| 2012/0321666 A1 | 12/2012 | Cooper et al. |
| 2016/0051698 A1* | 2/2016 | Schneck .............. A61P 31/00 424/134.1 |

FOREIGN PATENT DOCUMENTS

| | | |
|---|---|---|
| WO | WO 02/072631 A2 | 9/2002 |
| WO | WO 2005/070090 A2 | 8/2005 |
| WO | WO 2005/118788 A2 | 12/2005 |
| WO | WO 2009/003492 A1 | 1/2009 |
| WO | WO 2009/094273 A2 | 7/2009 |
| WO | WO 2015/188839 A2 | 12/2015 |
| WO | WO 2015/189356 A1 | 12/2015 |

OTHER PUBLICATIONS

Bruns et al. (Clinical cancer research, 2015, p. 2075-2083).*
Andersen, R. S. et al.."Dissection of T-cell antigen specificity in human melanoma", Cancer Res. 72, 1642-50 (2012).
Barrett, D. M. et al., "Relation of clinical culture method to T-cell memory status and efficacy in xenograft models of adoptive immunotherapy", Cytotherapy 16, 619-630 (2014).
Brimnes, MK et al., "Generation of autologous tumor-specific T cells for adoptive transfer based on vaccination, in vitro restimulation and CD3/CD28 dynabead-induced T cell expansion", Cancer Immunol Immunother. 61(8):1221-3, Aug. 2012.
Bruns, H. et al., "CD47 Enhances In Vivo Functionality of Artificial Antigen-Presenting Cells", Clin. Cancer Res. 1-10 (2015).
Buchholz, V. R. et al., "The origin of diversity: Studying the evolution of multi-faceted CD8 + T cell responses", Cell. Mol. Life Sci. 69, 1585-1595 (2012).
Graef, P. et al., "Serial Transfer of Single-Cell-Derived Immunocompetence Reveals Stemness of CD8+ Central Memory T Cells", Immunity 41, 116-126 (2014).
Huarte, E. et al., "Ex vivo expansion of tumor specific lymphocytes with IL-15 and IL-21 for adoptive immunotherapy in melanoma", Cancer Lett. 285, 80-8 (2009).
Poschke, I. et al., "Tumor-induced changes in the phenotype of blood-derived and tumor-associated T cells of early stage breast cancer patients", Int. J. Cancer 131, 1611-20 (2012).
Radvanyi, L. G. et al., "Specific lymphocyte subsets predict response to adoptive cell therapy using expanded autologous tumor-infiltrating lymphocytes in metastatic melanoma patients", Clin. cancer Res. (2012).
Rapoport, A. P. et al., "Rapid Immune Recovery and Graft-versus-Host Disease-Like Engraftment Syndrome following Adoptive Transfer of Costimulated Autologous T Cells", Clin. Cancer Res. 15, 4499-4507 (2009).
Rosenberg, S. A. et al., "Adoptive cell transfer as personalized immunotherapy for human cancer", Science (80-.). 348, 62-68 (2015).
Toebes, M. et al., "Design and use of conditional MHC class I ligands", Nat.Med. 12, 246-251 (2006).
Wu, F. et al., "Human effector T cells derived from central memory cells rather than CD8+T cells modified by tumor-specific TCR gene transfer possess superior traits for adoptive immunotherapy", Cancer Lett. 339, 195-207 (2013).
Yu X et al., "Artificial antigen presenting cells plus IL-15 and IL-21 efficiently induce melanoma-specific cytotoxic CD8(+)CD28(+) T lymphocyte responses", Asian Pacific Journal of Tropical Medicine, vol. 6, 2013, pp. 467-472.
Zhou, J et al., "Persistence of multiple tumor-specific T-cell clones is associated with complete tumor regression in a melanoma patient receiving adoptive cell transfer therapy", J. Immunother. 28, 53-62 (2005).

* cited by examiner

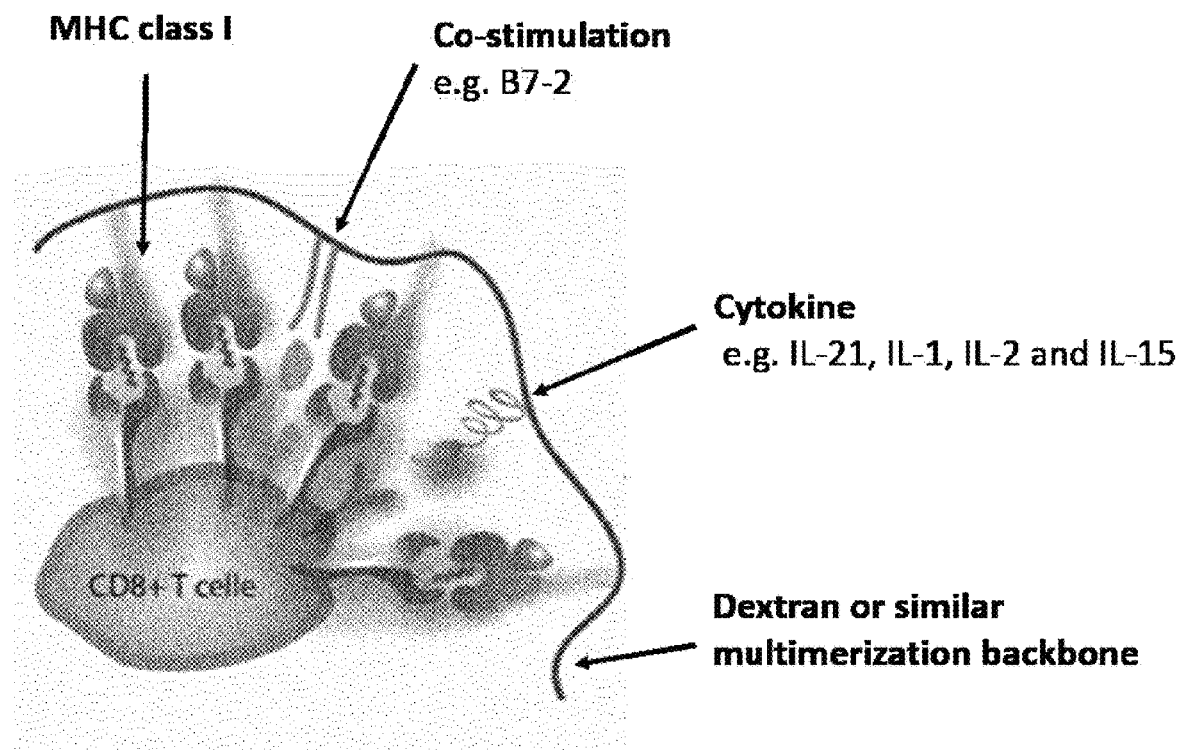
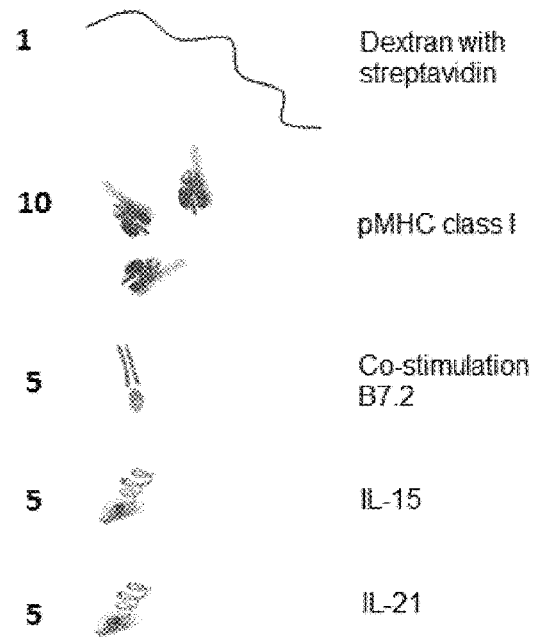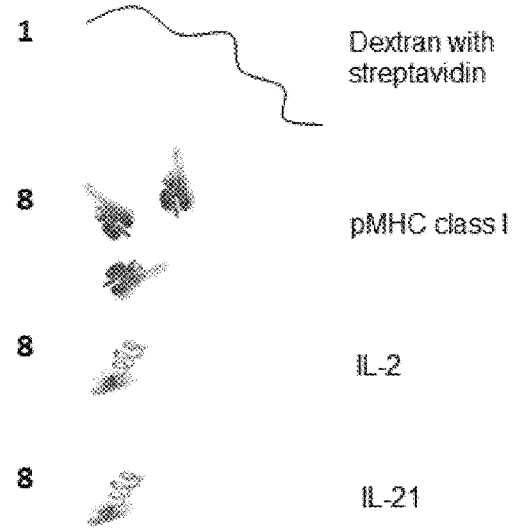
Fig. 1A

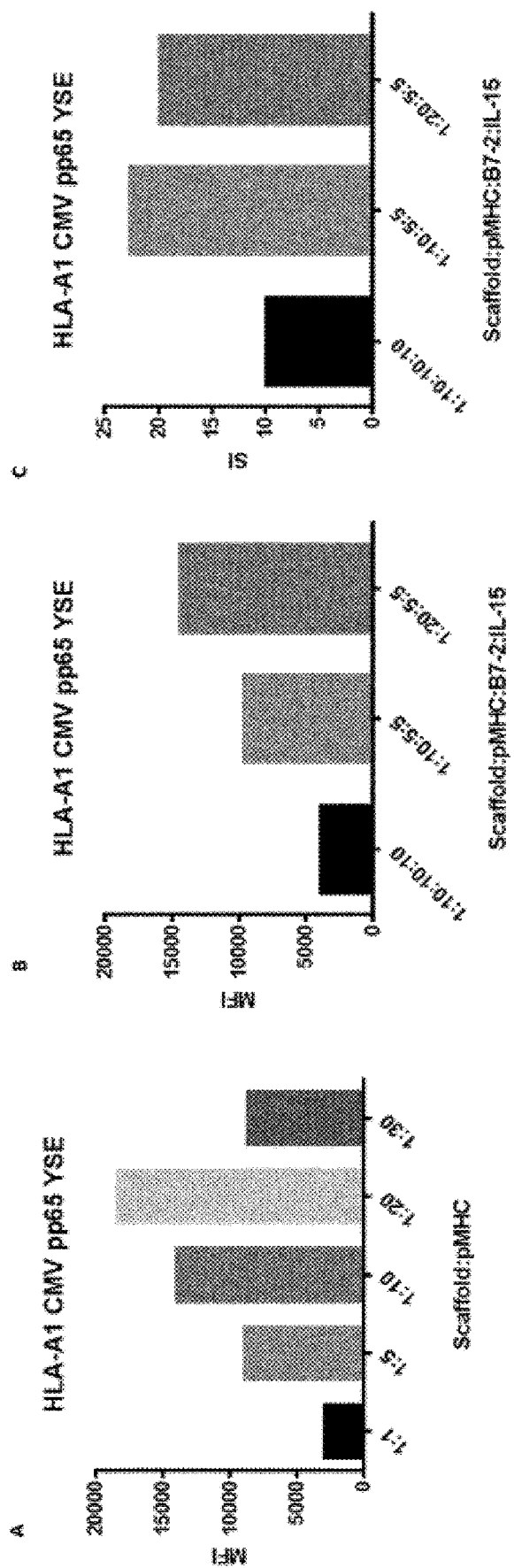
Fig. 2A-C

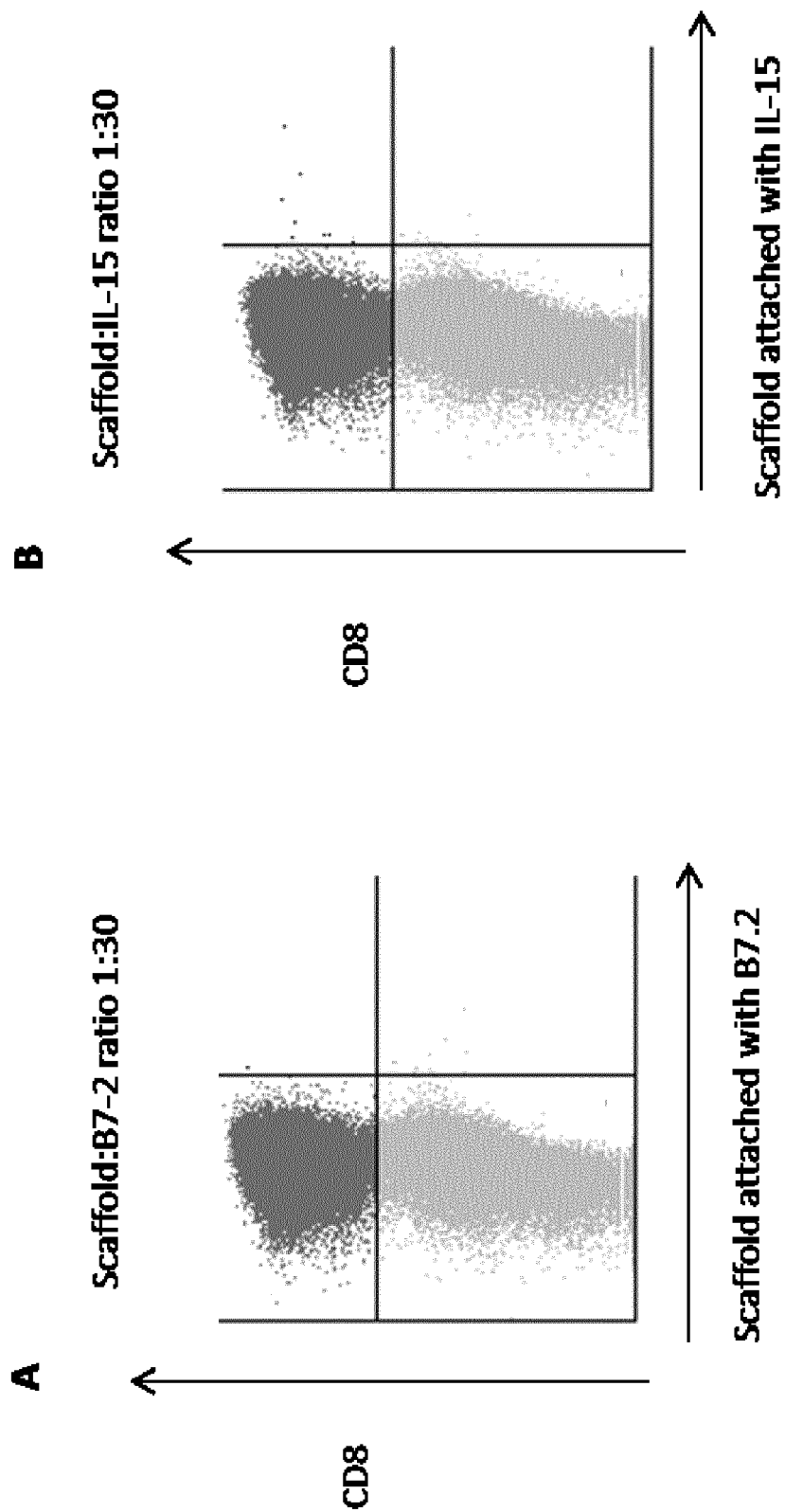
Fig. 3A-B

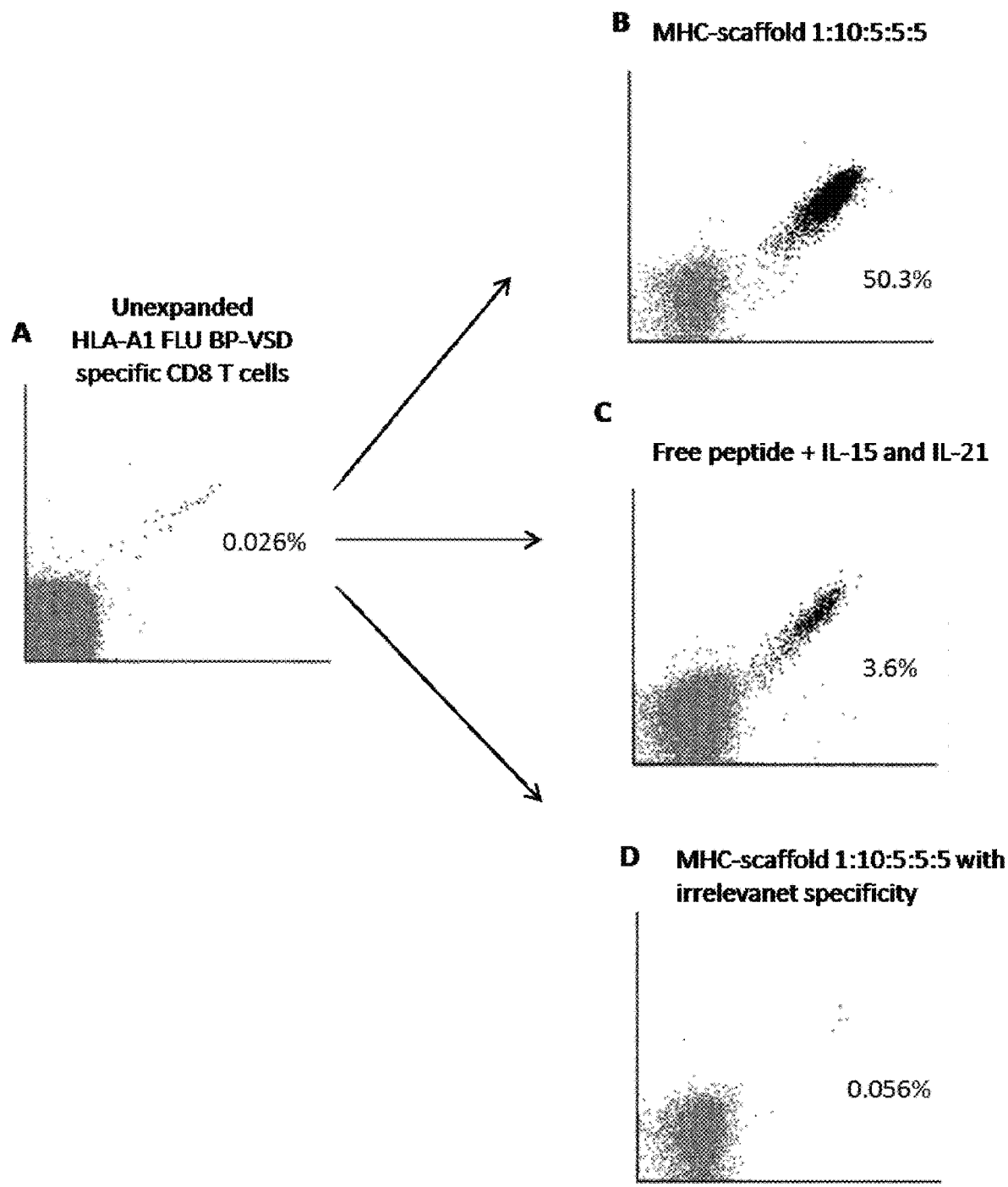
Fig. 4A-D

E
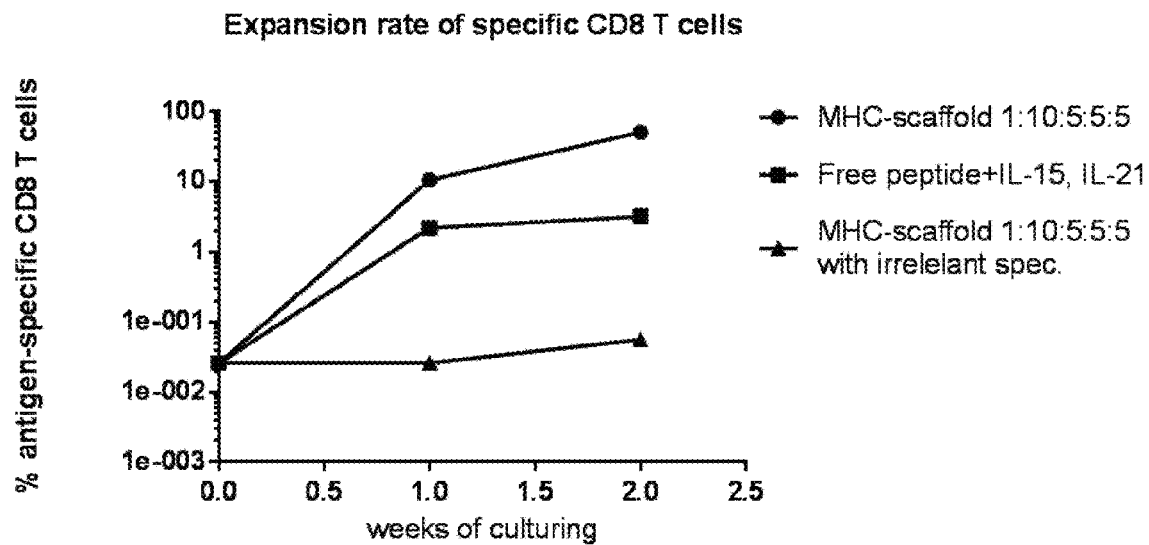
F
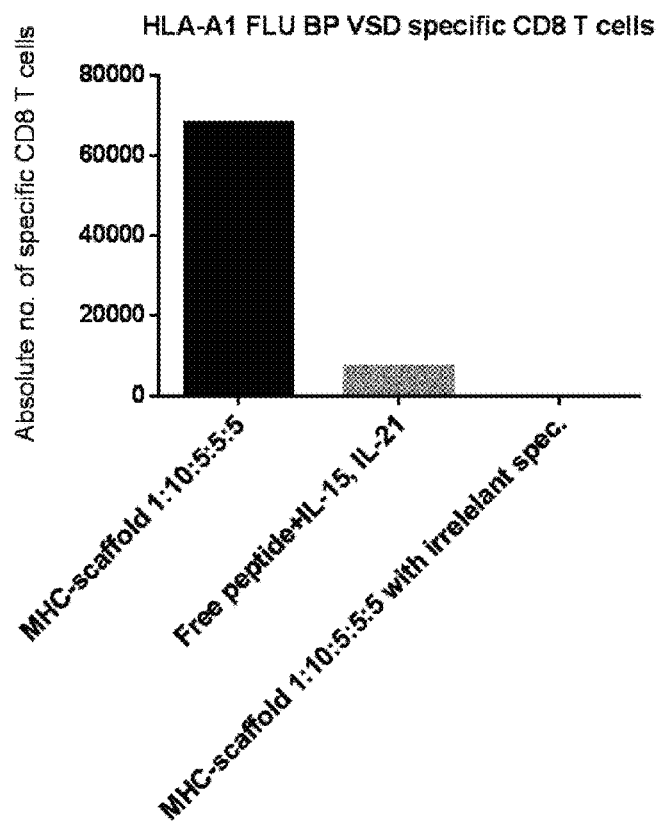
Fig. 4E-F

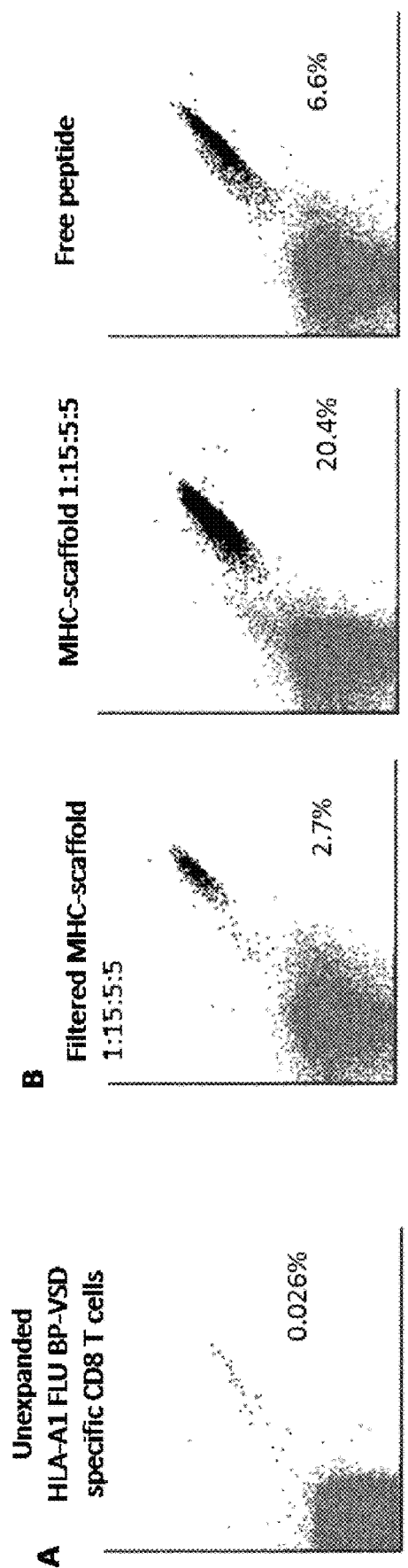
Fig. 5A-B

C
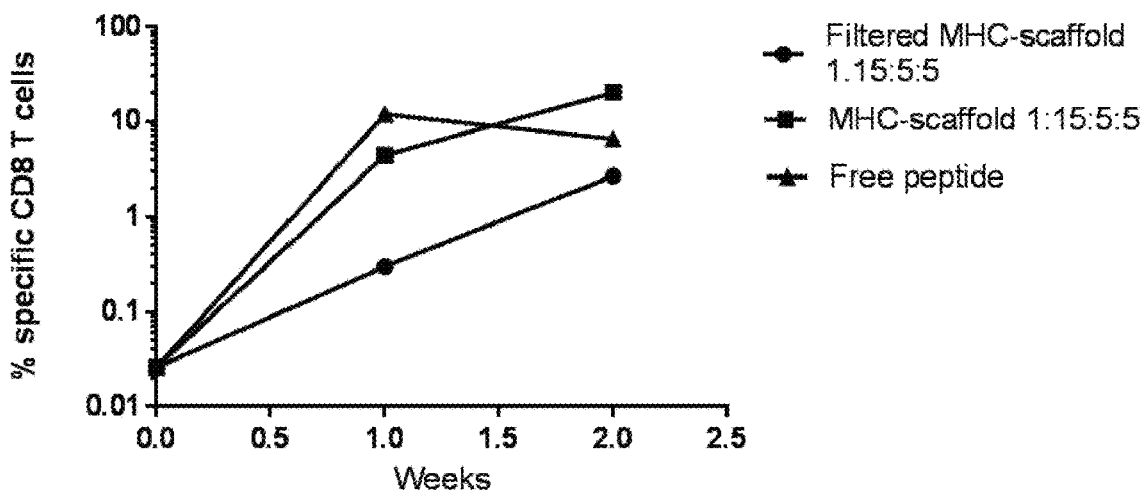
D
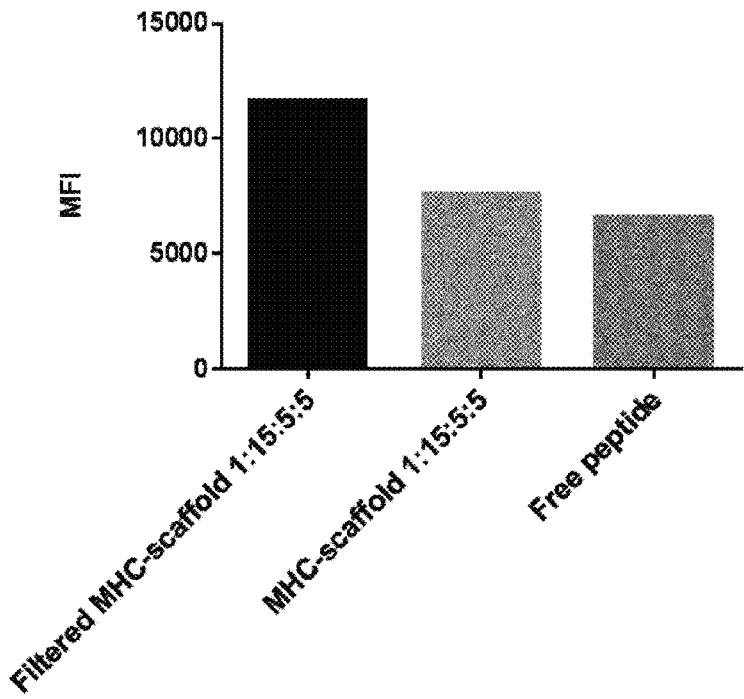
Fig. 5C-D

A
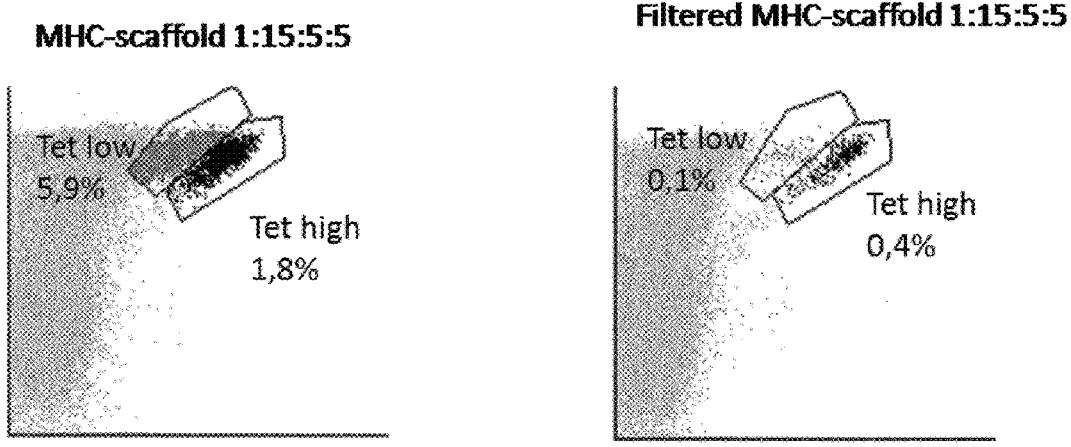
B
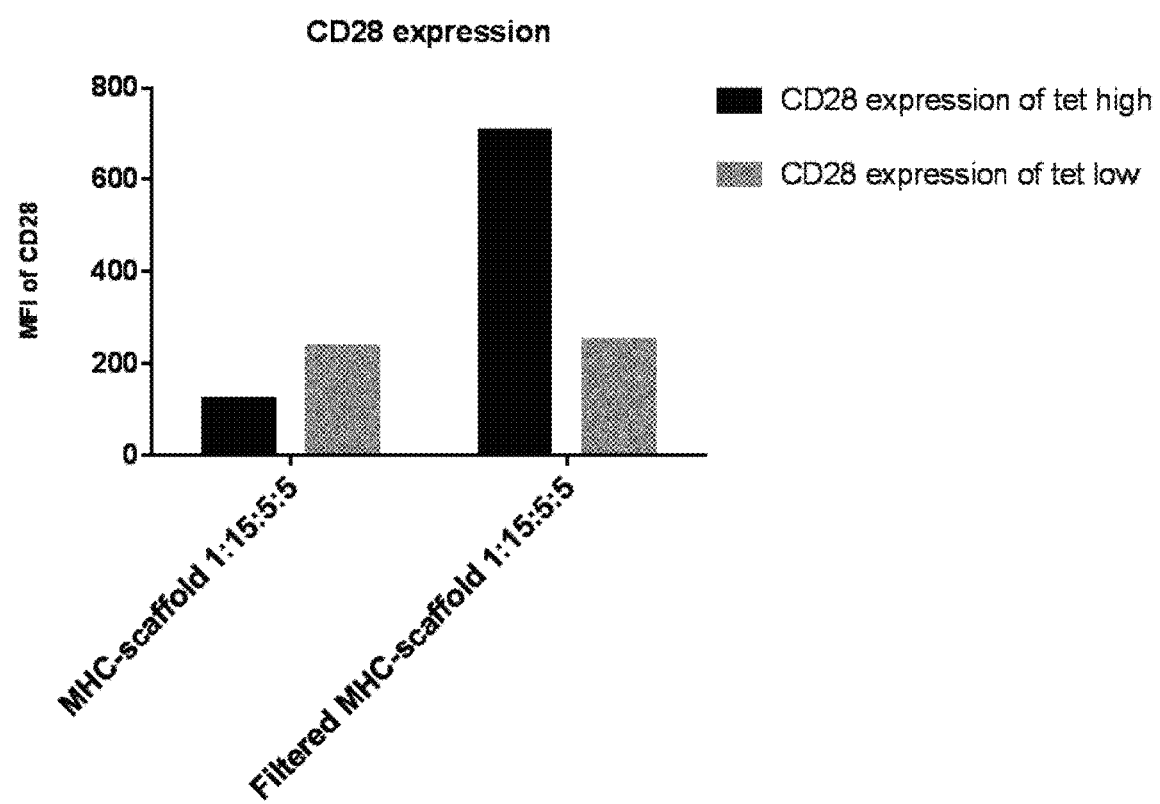
Fig. 6A-B

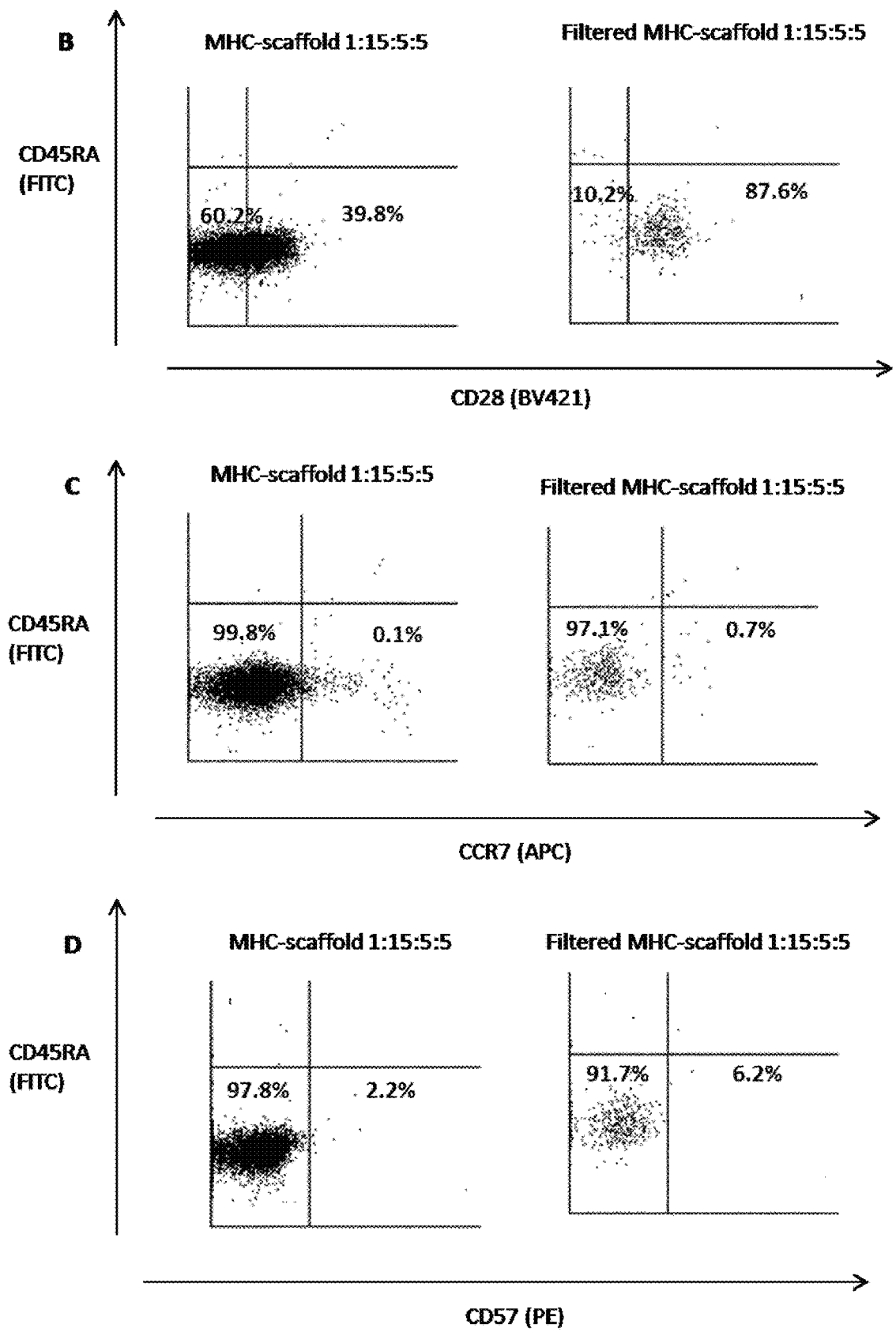
Fig. 7B-D

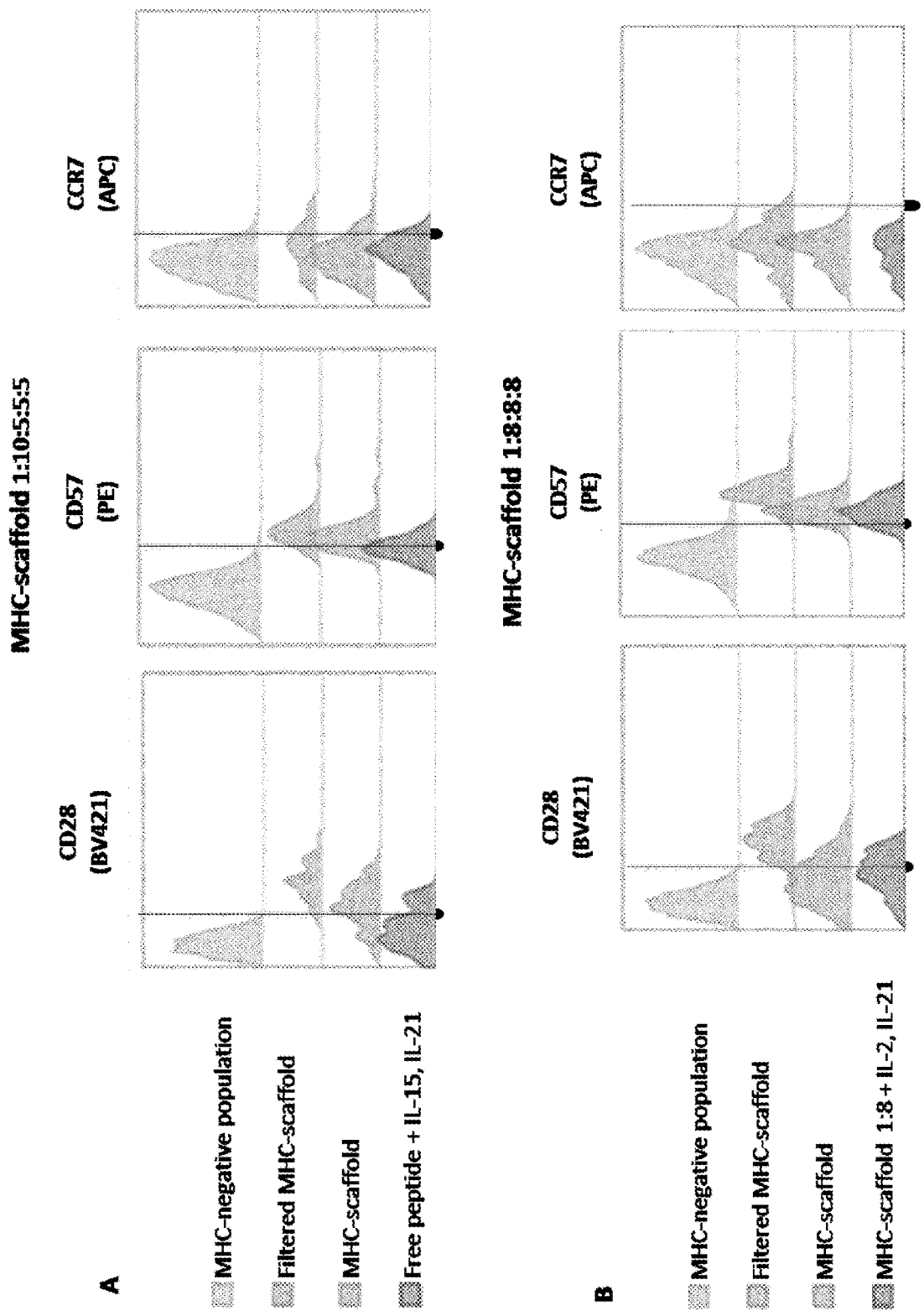
Fig. 8A-B

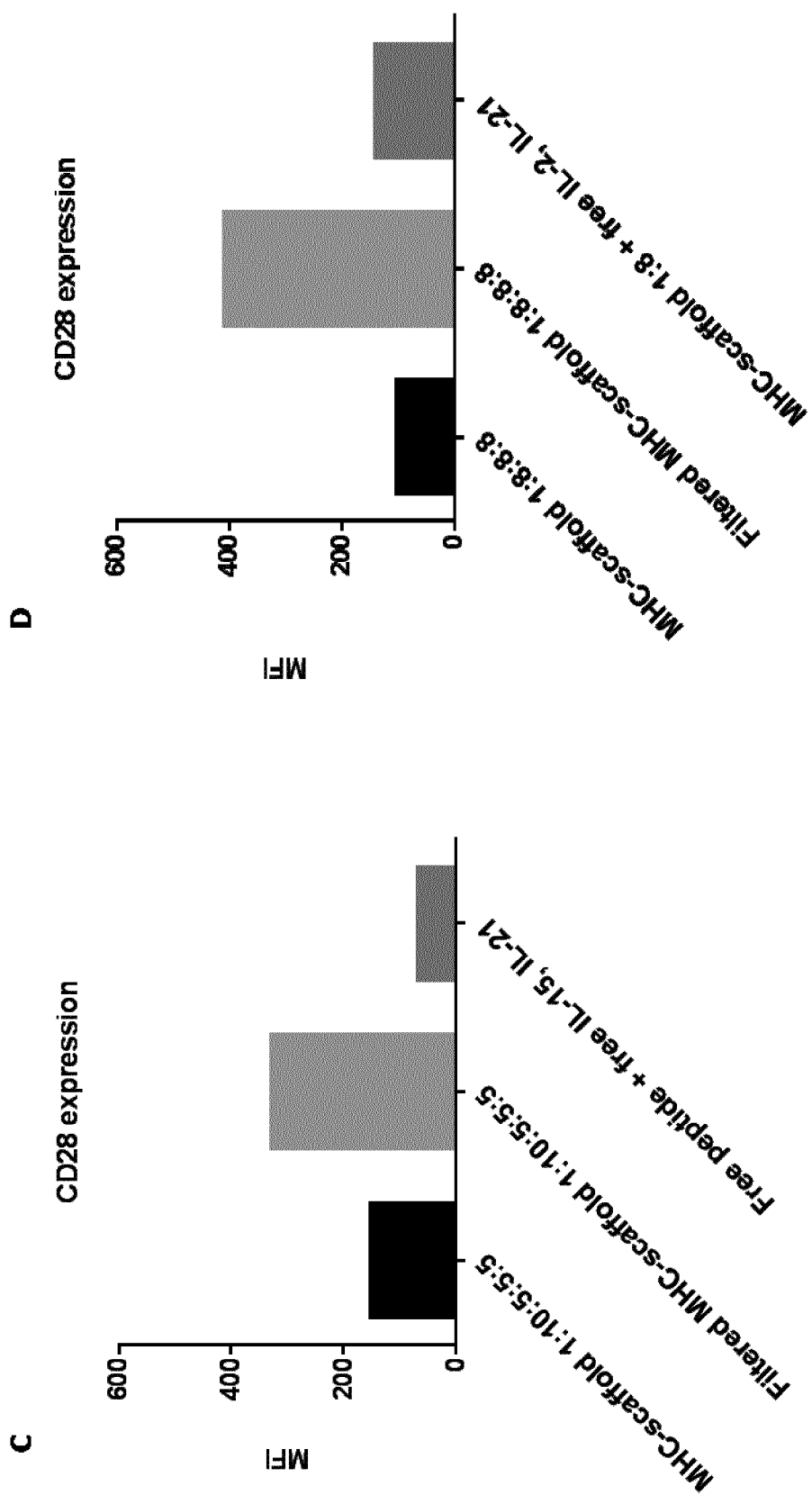
Fig. 8C-D

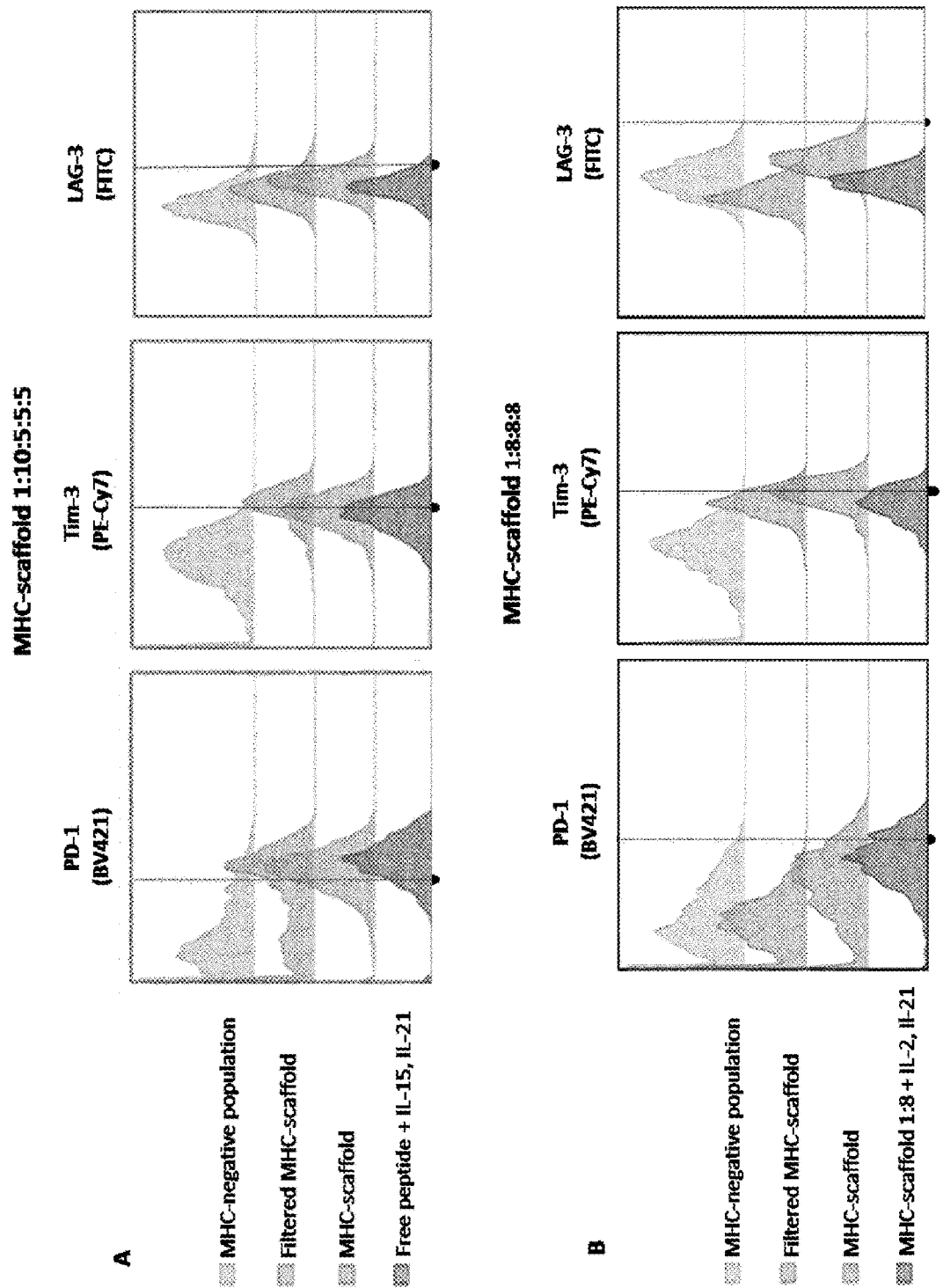
Fig. 9A-B

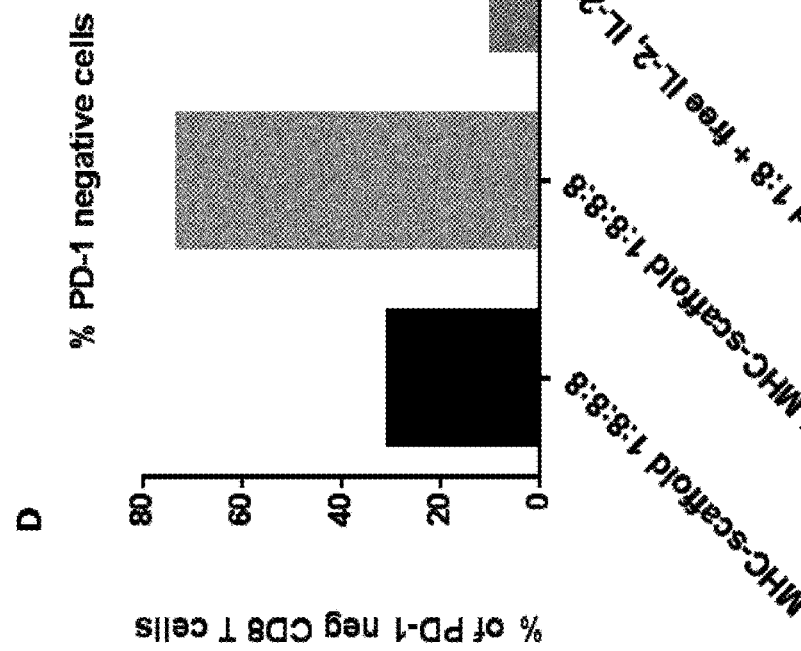
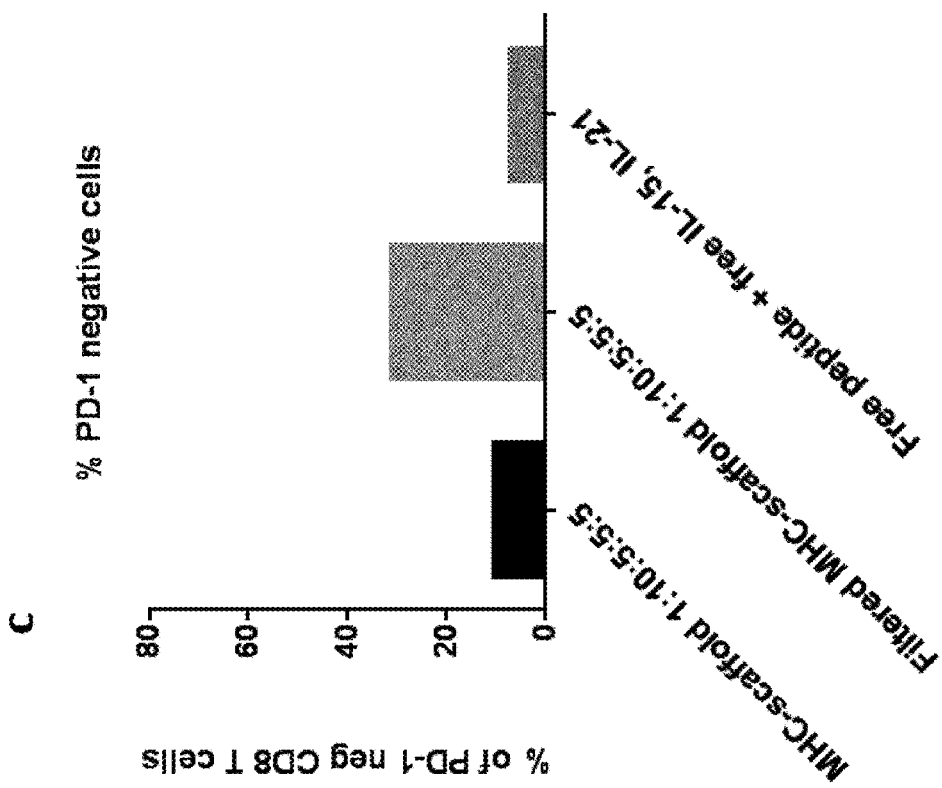
Fig. 9C-D

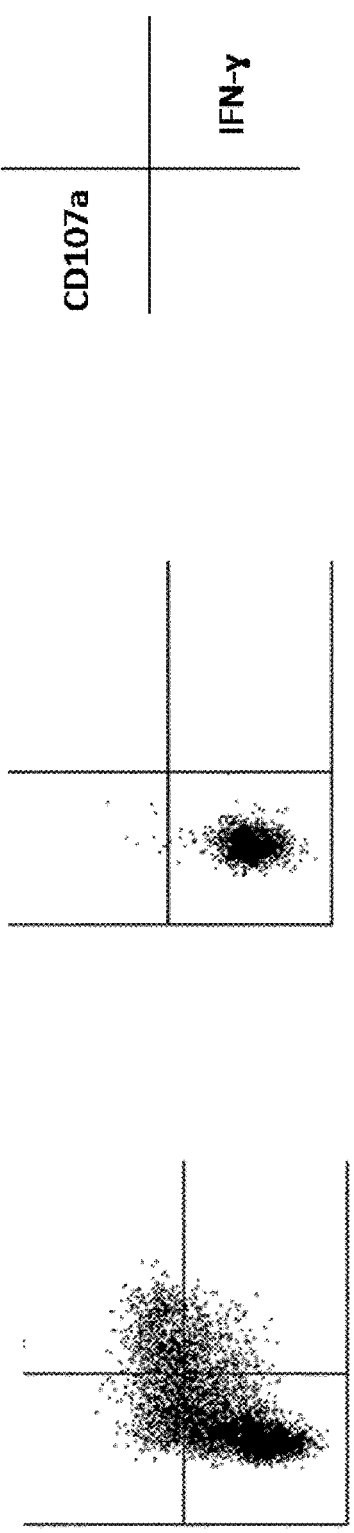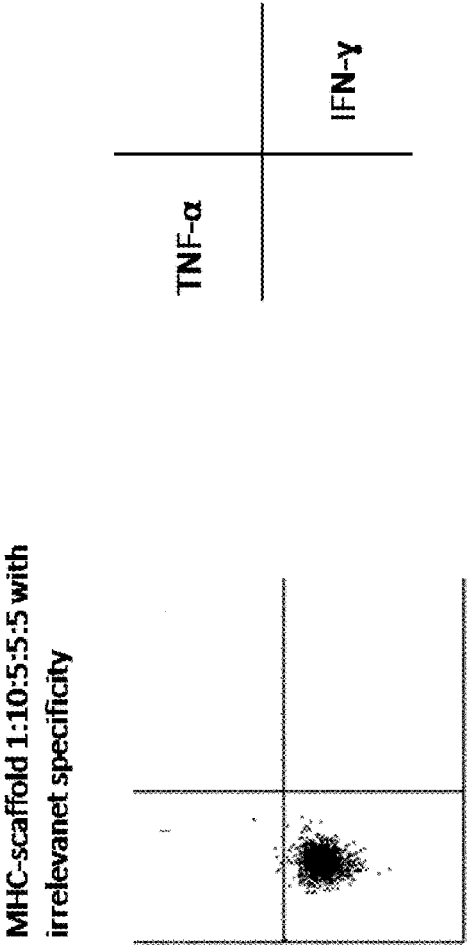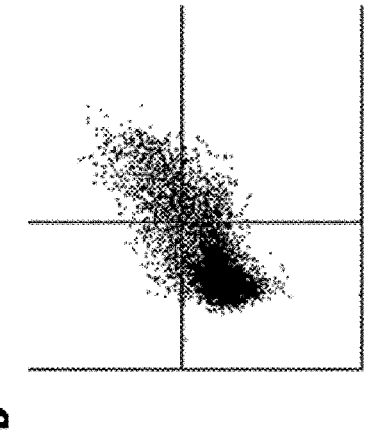
Fig. 11A-B

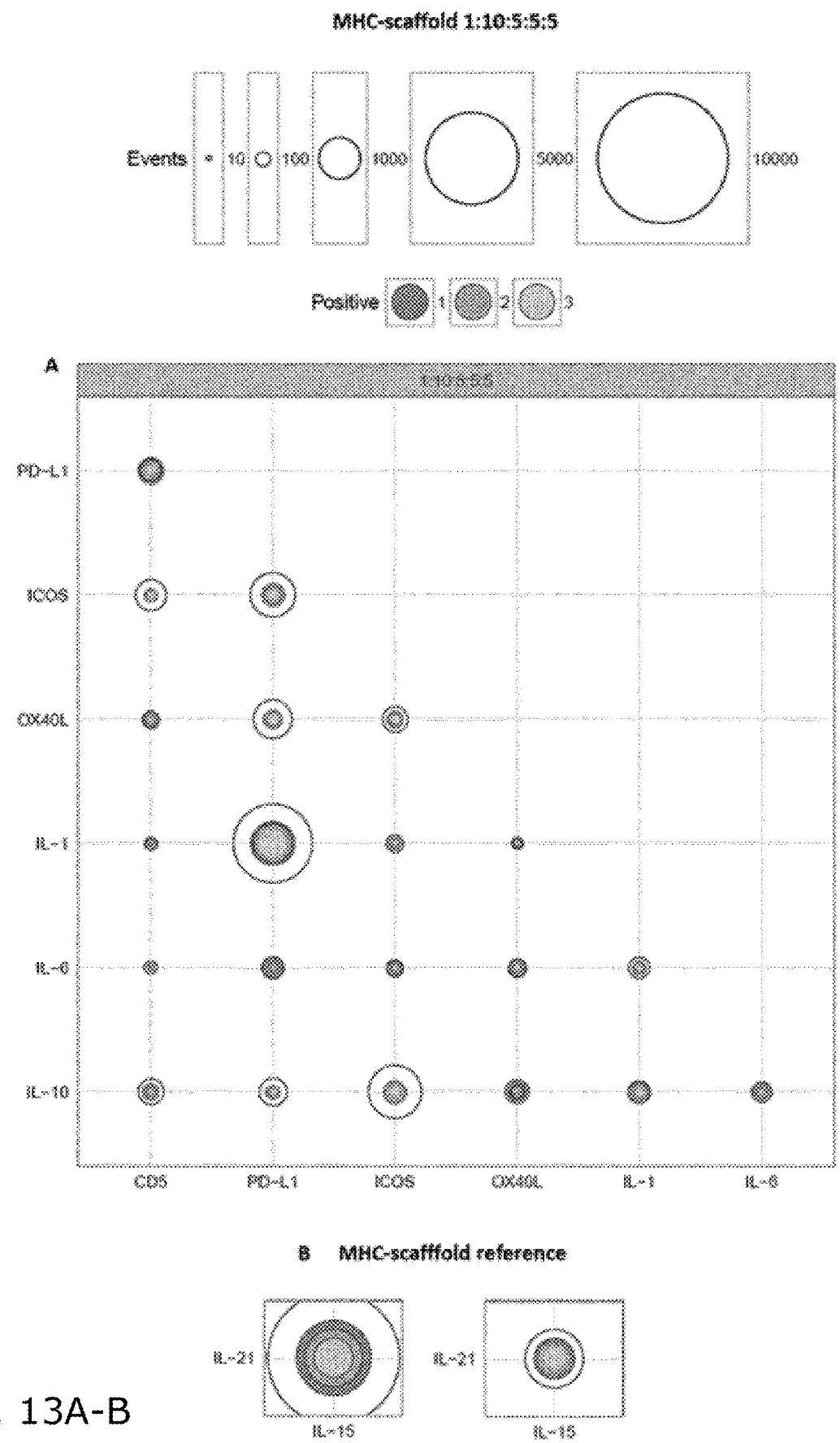
Fig. 13A-B

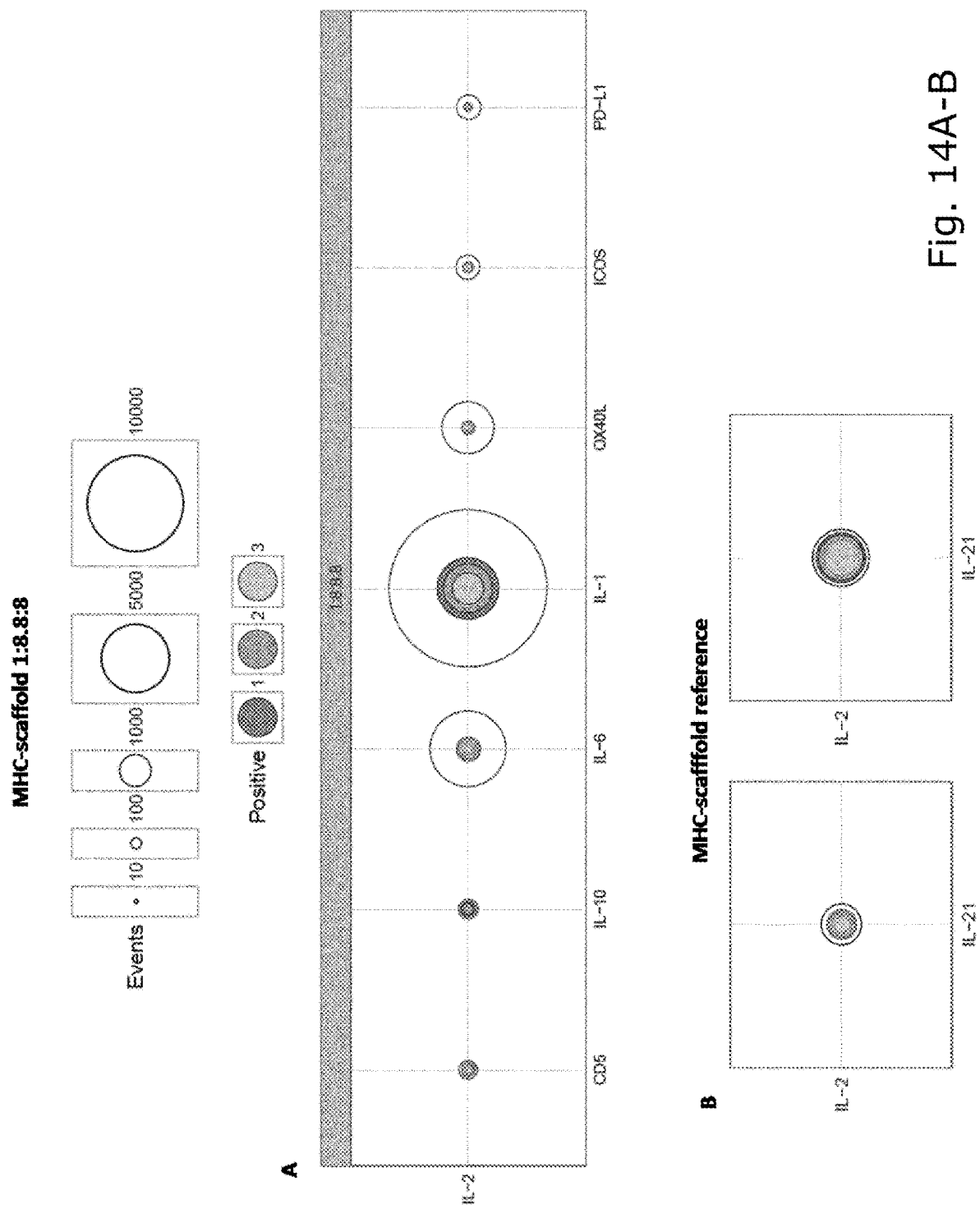
Fig. 14A-B

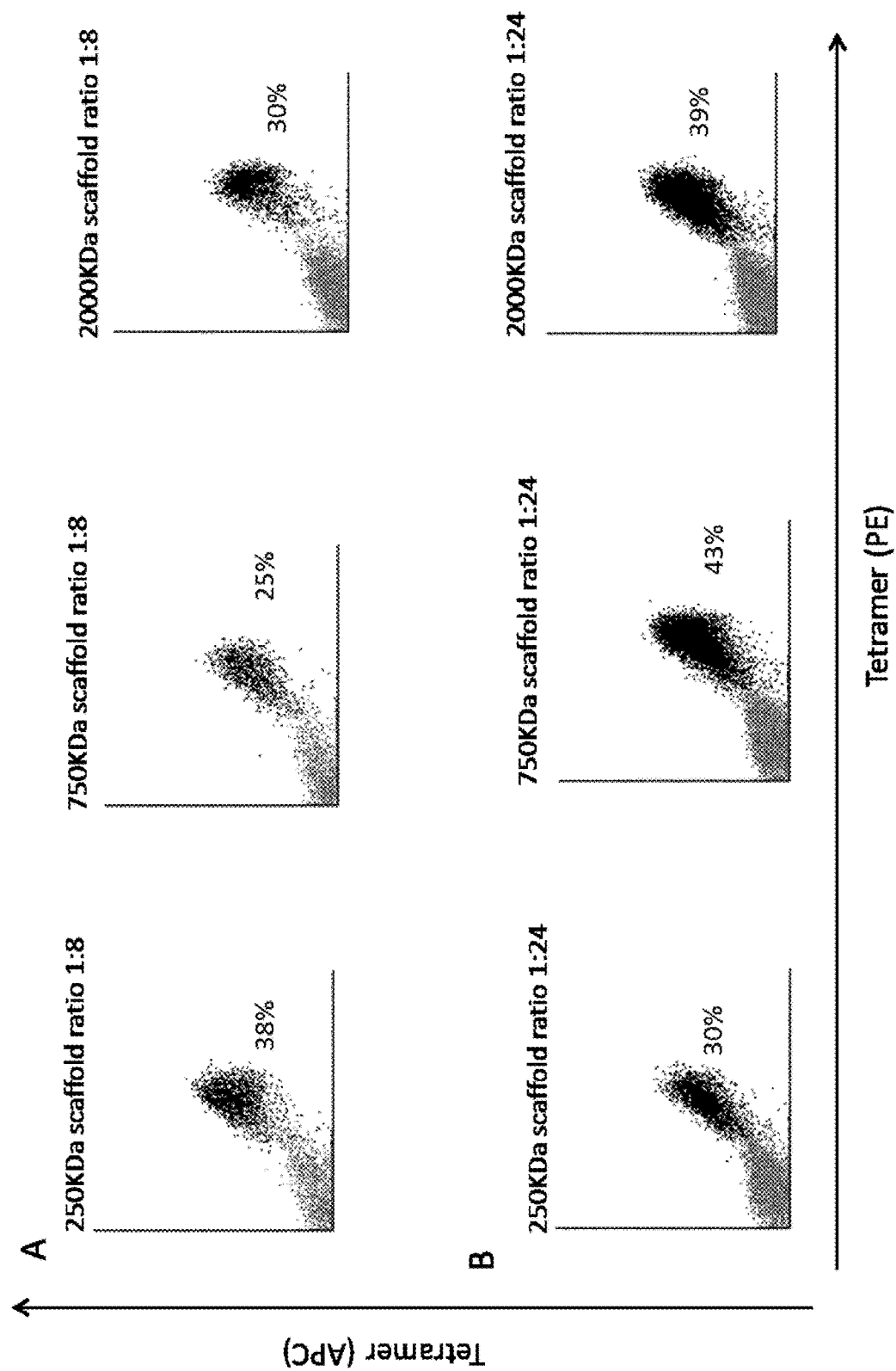
Fig. 18A-B

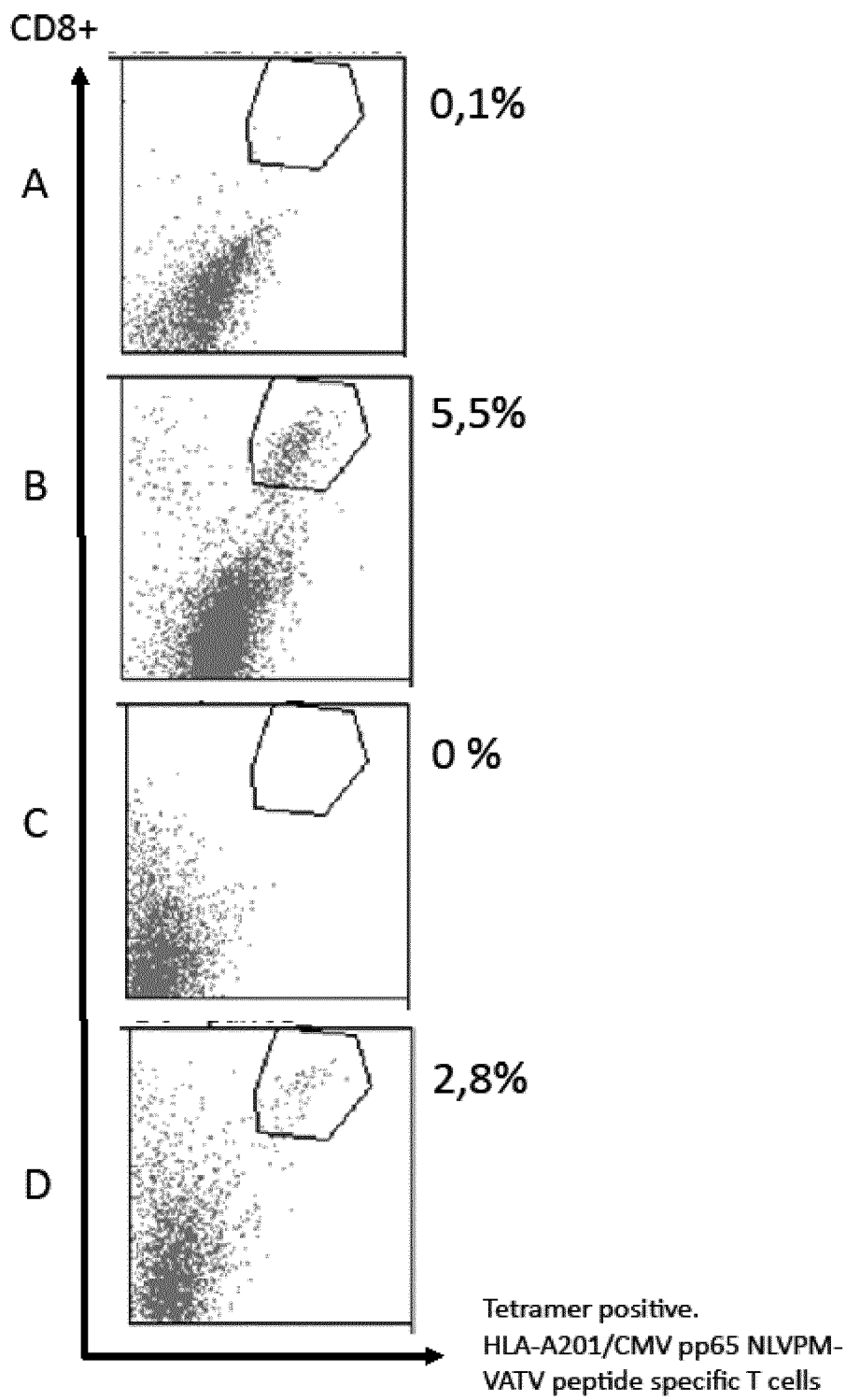
Fig. 20A-D

ANTIGEN PRESENTING SCAFFOLDS FOR IMMUNE-CELL MANIPULATION

CROSS REFERENCE TO RELATED APPLICATIONS

This application is a U.S. National Phase Application of PCT International Application Number PCT/EP2017/083862, filed on Dec. 20, 2017, designating the United States of America and published in the English language, which is an International Application of and claims the benefit of priority to European Patent Application No. 16205918.2, filed on Dec. 21, 2016. The disclosures of the above-referenced applications are hereby expressly incorporated by reference in their entireties.

REFERENCE TO SEQUENCE LISTING

A Sequence Listing submitted as an ASCII text file via EFS-Web is hereby incorporated by reference in accordance with 35 U.S.C. § 1.52(e). The name of the ASCII text file for the Sequence Listing is SeqList-PLOUG39-082APC.txt, the date of creation of the ASCII text file is Jun. 14, 2019, and the size of the ASCII text file is 1 KB.

TECHNICAL FIELD OF THE INVENTION

The present invention relates to artificial antigen presenting cell (aAPC) scaffolds to provide cells with specific functional stimulation to obtain phenotypic and functional properties ideal to mediate tumor regression or viral clearance. In particular, the scaffolds of the present invention comprise antigens, such as peptide-MHC (pMHC) class I molecules, and specific combinations of cytokines and co-stimulatory molecules to allow effective expansion and functional stimulation of specific T cells.

BACKGROUND OF THE INVENTION

The immunotherapeutic approach adoptive cell transfer (ACT), in which tumor-reactive T cells from peripheral blood (PBMC) or tumor infiltrating lymphocytes (TILs) are extracted from a patient, activated and expanded ex vivo, and subsequently given back to the patient, has in malignant melanoma studies showed clinical durable responses in more than 50% of patients. However, the expansion of tumor-reactive T cells from PBMCs or TILs requires extensive ex vivo culturing often at the cost of T cell differentiation and functional capacity. As a result, the transferred T cell product may not contain a sufficient frequency of tumor-reactive CD8 T cells with the appropriate phenotypic and functional characteristics to mediate tumor regression. Furthermore, the majority of such tumor infiltrating T cells may not be tumor specific but rather bystander infiltration of T cells from the periphery, with a T cell receptor (TCR) recognition not matching any tumor antigens. Finally, the fraction of tumor-reactive T cells may have a reduced growth potential due to the suppressive environment present at the tumor site.

Attempts have been made to utilize artificial antigen presenting cells (aAPCs) to overcome the problem of insufficient differentiation and functional capacity of the expanded T cells. The simple concept behind aAPCs is that they mimic the natural interaction between the TCR and the specific peptide antigen presented by the major histocompatibility complex (MHC). This interaction is the core step in generation of immunity through activation, expansion and differentiation of T cells that are capable of eliciting an efficient immune response. The natural generation of a T cell response is further aided by cytokines and co-stimulatory molecules, which serves to induce T cell activation and function. Thus, incorporation of all the necessary molecules into a single aAPC scaffold is a promising tool to overcome some of the challenges of expansion of T cells. The aAPCs form the ideal immunological synapse for T cell activation and differentiation. However, a crucial challenge is the uncovering of combinations of molecules enabling the aAPCs to efficiently expand the extracted TILs while also maintaining a functional phenotype.

In WO2002072631 are disclosed many concepts of utilizing MHC platforms, wherein one of them is a MHC construct comprising a carrier molecule having attached thereto one or more MHC molecules. The construct may also contain biologically active molecules such as co-stimulatory molecules or cell modulating molecules. The MHC construct is envisioned amongst others to be used for expansion of cells recognizing the construct and used to generate a therapeutic composition for use in treatment of disease, such as cancer and others. WO2002072631 discloses many co-stimulatory molecules and cytokines that may be suitable for T cell expansion, but fails to identify any specific combinations particularly suitable and effective for the purpose of expansion of T cells.

US 2011/318380 disclose application of the MHC construct described in WO2002072631 for cancer vaccines and immune monitoring. However, US 2011/318380 do not exemplify any specific combinations of co-stimulatory molecules and cytokines particularly suitable and effective for the purpose of expansion of T cells.

WO2009003492 is mainly focused on detection of antigen specific T cells, but also discloses the expansion of antigen specific T cells. Described therein are MHC multimers with and without complexed peptides, methods for their preparation and methods for their use in analysis and therapy, including isolation of antigen specific T-cells capable of inactivation or elimination of undesirable target T-cells. The MHC multimers according to WO2009003492 may comprise a dextran scaffold and co-stimulatory- and cell modulating molecules. However, the disclosure fails to pinpoint specific combinations of molecules especially effective for the purpose of expansion of T cells.

In WO2009094273 is disclosed an aAPC composition comprising nanoparticles, cytokines, coupling agents, T cell receptor activators and co-stimulatory molecules for use to expand antigen-specific T cells. The T cell receptor activator may be an MHC molecule bound to a peptide antigen. Furthermore, the use of the expanded T cells in adoptive immunotherapy is described. However, only the suitability of a single cytokine on an aAPC, namely IL-2, is explored and only in comparison with the exogenous cytokine.

Thus, common for the previous disclosures of aAPC scaffolds is that they only describe the concept in a largely generic manner. Since the success criteria for T cell expansion, i.e. high ratio of active T cells, high antigen specificity of the T cells and high functionality of the T cells, is only met when specific combinations of stimulatory molecules are combined, a great need for well-defined and effective aAPC scaffolds exists. Only when all of the three success criteria for T cell expansion is fulfilled will the resulting population of T cells be optimally prepared to apply their antitumor or antiviral functions.

Hence, improved aAPC scaffolds would be advantageous. In particular, the provision of more efficient aAPC scaffolds with high ratio of active T cells, high antigen specificity of the T cells and high functionality of the T cells would be in demand.

SUMMARY OF THE INVENTION

Thus, an object of the present invention relates to the provision of artificial antigen presenting cell (aAPC) scaffolds with improved capabilities for expansion of tumor-reactive T cells extracted from peripheral blood (PBMC) or tumor infiltrating lymphocytes (TILs).

In particular, it is an object of the present invention to provide an aAPC scaffold that solves the above mentioned problems of the prior art of insufficient T cell differentiation and functional capacities of the expanded T cell population.

Another object of the present invention is to utilize the obtained expanded T cell populations with optimized phenotypic and functional properties to mediate tumor regression or viral clearance.

Thus, one aspect of the invention relates to an artificial antigen presenting cell (aAPC) scaffold comprising a polymeric backbone to which are attached the following template molecules:
 i. at least one major histocompatibility complex molecule comprising an antigenic peptide (pMHC),
 ii. at least one cytokine selected from the group consisting of IL-21, IL-2, IL-15, IL-1, IL-6, IL-10 and IL-7,
 iii. optionally, at least one co-stimulatory molecule selected from the group consisting of B7.2 (CD86), B7.1 (CD80), CD40, ICOS and PD-L1, and
 iv. optionally, at least one CD47 molecule.

A preferred aspect of the invention relates to an artificial antigen presenting cell (aAPC) scaffold comprising a polymeric backbone to which are attached the following template molecules:
 i. at least two different gamma-chain receptor cytokines, such as at least two different gamma-chain receptor cytokines selected from the group consisting of IL-21, IL-2, IL-15, IL-4, IL-9 and IL-7,
 ii. at least one antigen,
 iii. optionally, at least one co-stimulatory molecule selected from the group consisting of B7.2 (CD86), B7.1 (CD80), CD40, ICOS and PD-L1, and
 iv. optionally, at least one CD47 molecule.

Another aspect of the present invention relates to a method for simultaneous in vitro stimulation and expansion of T cells, comprising the following steps:
 i. providing a sample comprising T cells,
 ii. contacting said sample with a solution comprising an aAPC scaffold according to the present invention,
 iii. stimulating and expanding T cells with specificity for said aAPC scaffold in culture, and
 iv. harvesting the T cells of step iii) from the culture to obtain an expanded antigen-specific population of T cells.

A further aspect of the present invention is to provide an expanded T cell population obtained by the method according to the present invention.

Yet another aspect of the present invention relates to an expanded T-cell population obtained by the method according to present invention for use as a medicament.

Still another aspect of the present invention is to provide an expanded T-cell population obtained by the method according to the present invention for use in the treatment of a cancer or viral condition.

BRIEF DESCRIPTION OF THE FIGURES

FIG. 2 shows (A) Mean fluorescent intensity (MFI) values for T cells stained using different antigen presenting scaffolds assembled in scaffold:pMHC ratios of 1:1, 1:5, 1:10, 1:20, 1:30 and applied in staining of PBMCs from a healthy donor with response against CMV pp65 YSE peptide. (B) MFI value and (C) SI values for T cell samples stained using different antigen presenting scaffolds assembled in scaffold:pMHC ratios of 1:10 or 1:20 and co-attached with B7-2 and IL-15 as co-stimulatory molecules in a ratio of 5:5.

FIG. 3 shows scaffolds assembled with either (A) B7-2 or (B) IL-15 in ratio 1:30 and applied in staining of healthy donor PBMCs. Fluorochrome on Y-axis is PE-Cy7 and flourochrome on X-axis is FITC.

FIG. 4 shows (A) Frequency of HLA-A1 FLU BP-VSD specific CD8 T cells from a healthy donor detected directly ex vivo with PE (X-axis) and APC (Y-axis) labeled tetramers. (B) Frequency of HLA-A1 FLU BP-VSD specific CD8 T cells after two weeks culturing with antigen presenting scaffolds with either the ratio 1:10:5:5 (scaffold:pMHC:B7-2:IL-15:IL-21), plus 20 IU/ml IL-2 added in the culture media, (C) free FLU BP-VSD peptide, IL-15, and IL-21, or (D) Antigen presenting scaffold with the ratio 1:10:5:5 carrying an irrelevant peptide specificity. (E) Expansion rate based on frequency of HLA-A1 FLU BP-VSD specific CD8 T cells, detected by tetramer staining from baseline, 1 week and 2 weeks after expansion. (F) Absolute number of HLA-A1 FLU BP-VSD specific CD8 T cells after 2 weeks expansion.

FIG. 5 shows (A) Frequency of HLA-A1 FLU BP-VSD specific CD8 T cells from a healthy donor detected directly ex vivo with PE (X-axis) and APC (Y-axis) labeled tetramers. (B) Frequency of HLA-A1 FLU BP-VSD specific CD8 T cells after two weeks culturing with either filtered antigen presenting-scaffolds with the ratio 1:15:5:5 (scaffold:pMHC:B7-2:IL-15), unfiltered antigen presenting scaffolds or free FLU BP-VSD peptide in the culture media, plus 20 IU/ml IL-2 was added to all cultures. The frequencies were detected with APC and PE labeled tetramers. (C) Expansion rate based on frequency of HLA-A1 FLU BP-VSD specific CD8 T cells, detected by tetramer staining from baseline, 1 week and 2 weeks after expansion. (D) MFI values from tetramer positive CD3/CD8 T cells after 2 weeks expansion with either filtered antigen presenting scaffolds with the ratio 1:15:5:5 (scaffold:pMHC:B7-2:IL-15), unfiltered antigen presenting scaffolds or free FLU BP-VSD peptide.

FIG. 6 shows (A) Frequencies of HLA-A3 FLU NP LIR specific CD8 T cells from a healthy donor after 2 weeks expansion with either unfiltered or filtered antigen presenting scaffold with the ratio 1:15:5:5 (scaffold:pMHC:B7-2:IL-15). The dot plots show two populations of antigen-specific CD8 T cells, one binding with high affinity (black population) and another binding with lower affinity (dark grey population) to PE-Cy7 labeled tetramers (X-axis), while equal staining intensity is obtained from the CD8 antibody, PerCP labeled (Y-axis). (B) Bar chart of CD28 expression of HLA-A3 FLU NP LIR specific CD8 T cells with high and low binding affinity to tetramers after 2 weeks expansion with either unfiltered or filtered antigen presenting scaffold with the ratio 1:15:5:5.

FIG. 8 shows expression of CD28, CD57 and CCR7 of HLA-A1 FLU BP-VSD specific CD8 T cells after 2 weeks expansion with (A) filtered and unfiltered antigen presenting scaffold with ratio 1:10:5:5:5 (scaffold:pMHC:B7-2:IL-15:IL-21) compared with free peptide IL-15 and IL-21, all these cultures had 20 IU/ML IL-2 in the culture media. (B) Filtered and unfiltered antigen presenting scaffold with ratio 1:8:8:8 (scaffold:pMHC:IL-2:IL-21) compared with antigen presenting scaffold 1:8 (scaffold:pMHC) with free IL-2 and IL21. (C) MFI value of CD28 expression from HLA-A1 FLU BP-VSD specific CD8 T cells after 2 weeks expansion with filtered and unfiltered antigen presenting scaffold with ratio 1:10:5:5:5 (scaffold:pMHC:B7-2:IL-15:IL-21) or free peptide, IL-15 and IL-21. (D) MFI value of CD28 expression from HLA-A1 FLU BP-VSD specific CD8 T cells after 2 weeks expansion with filtered and unfiltered antigen presenting scaffold with ratio 1:8:8:8 (scaffold:pMHC:IL-2:IL-21) or antigen presenting scaffold 1:8 (scaffold:pMHC) with free IL-2 and IL21.

FIG. 9 shows expression of PD-1, Tim-3, and LAG-3 of HLA-A1 FLU BP-VSD specific CD8 T cells after 2 weeks expansion with (A) filtered and unfiltered antigen presenting scaffold with ratio 1:10:5:5:5 (scaffold:pMHC:B7-2:IL-15:IL-21) compared with free peptide, IL-15 and IL-21, all these cultures had 20 IU/ML IL-2 in the culture media. (B) Filtered and unfiltered antigen presenting scaffold with ratio 1:8:8:8 (scaffold:pMHC:IL-2:IL-21) compared with antigen presenting scaffold 1:8 (scaffold:pMHC) with free IL-2 and IL21. (C) Frequency of PD-1 negative HLA-A1 FLU BP-VSD specific CD8 T cells after 2 weeks expansion with filtered and unfiltered antigen presenting scaffold with ratio 1:10:5:5:5 (scaffold:pMHC:B7-2:IL-15:IL-21) or free peptide, IL-15 and IL-21. (D) Frequency of PD-1 negative HLA-A1 FLU BP-VSD specific CD8 T cells after 2 weeks expansion with filtered and unfiltered antigen presenting scaffold with ratio 1:8:8:8 (scaffold:pMHC:IL-2:IL-21) or antigen presenting scaffold 1:8 (scaffold:pMHC) with free IL-2 and IL21.

FIG. 11 shows dot plots showing the expression of (A) CD107a and IFN-γ, and (B) TNF-α and IFN-γ among CD8 T cells following stimulation with HLA-A1 FLU BP-VSD peptide. Cultures were stimulated for 2 weeks with antigen presenting scaffolds with ratio 1:10:5:5:5 (scaffold:pMHC:B7-2:IL-15:IL-21) carrying either relevant (left plots) or irrelevant peptide specificity (right plots) in the MHC complex. In (A) the CD107a antibody is PE labeled (Y-axis) and the IFN-γ antibody is APC labeled (X-axis), in (B) the TNF-α antibody is PE-Cy7 labeled (Y-axis) and the IFN-γ antibody is APC labeled (X-axis). These stainings were made in duplicate, only one of each staining is shown.

Figure 1B:
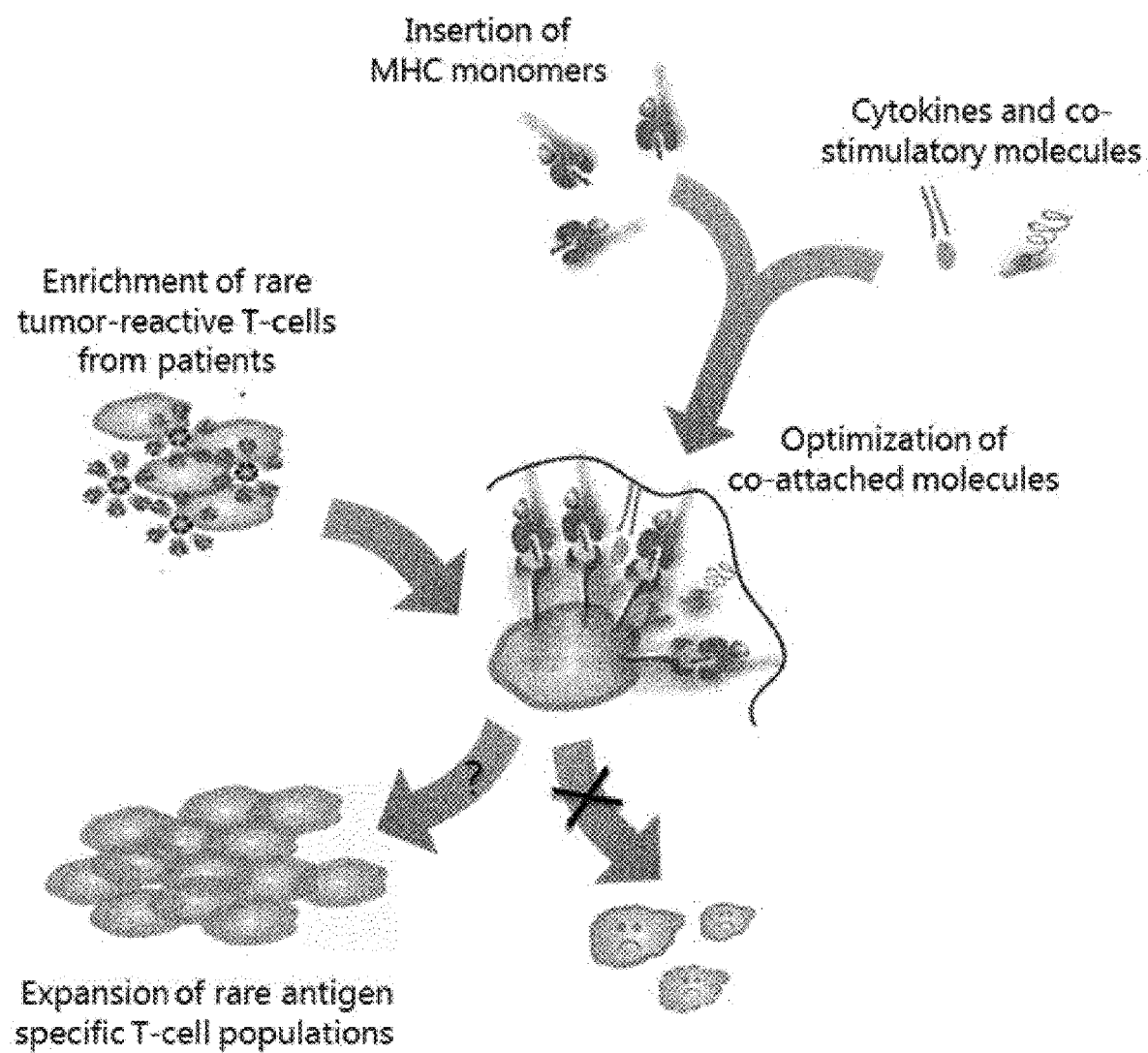
FIG. 1 shows (A) a schematic overview over an exemplary artificial antigen presenting cell (aAPC) scaffold. The aAPC scaffold is comprised of a backbone to which are attached template molecules such as peptide-MHC (pMHC) molecules, cytokines and optionally co-stimulatory molecules. Furthermore, CD47 molecules may be attached to the aAPC scaffold. Examples are given of aAPC scaffolds, wherein different ratios of the backbone and template molecules are assembled into aAPC scaffolds. (B) Illustration of how carefully selected combinations of template molecules may be combined in an aAPC scaffold and utilized to expand specific T cell populations extracted from patients.

1-4. 4 virus responses were expanded in individual cultures (one per culture)

5. The 4 virus responses were expanded simultaneously (4 per culture)

The specificity of the 4 evaluated peptide-MHC responses were: HLA-A2 FLU MP 58-66 GIL, HLA-A2 EBV LMP2 FLY, HLA-A2 CMV pp65 NLV and HLA-A2 EBV BRLF1 YVL.

FIG. 13 shows (A) Expression of TNF-α, IFN-γ and CD107a within T cell cultures stimulated with the respective antigen presenting scaffolds for 2 weeks, and thereafter exposed to the specific peptide (HLA-A2 EBV LMP2 CLG) for 4 hours. 21 different antigen presenting scaffolds with ratio 1:10:5:5:5 (scaffold:pMHC:B7-2:molecule 1:molecule 2) were used. The outermost black circle represents the absolute number of antigen-specific CD8 T cells (events) detected with tetramer staining, circle 1 refers to expression of one of the three markers (TNF-α, IFN-γ and CD107a), circle 2 refers to expression of the two of the three markers, and circle 3 refers to expression of all three markers. (B) Reference antigen presenting scaffold with the ratio 1:10:5:5:5 (scaffold:pMHC:B7-2:IL-15:IL-21).

FIG. 14 shows (A) Expression of TNF-α, IFN-γ and CD107a within T cell cultures stimulated with the respective antigen presenting scaffolds for 2 weeks, and thereafter exposed to the specific peptide (HLA-A2 EBV LMP2 CLG) for 4 hours. 7 different antigen presenting scaffolds with ratio 1:8:8:8 (scaffold:pMHC:IL-2:molecules 1) were used. Molecule 1 varied between PD-L1, ICOS, OX40L, CD5, IL-1 IL-6, IL-10. The outermost black circle represents the absolute number of antigen-specific CD8 T cells (events) detected with tetramer staining, circle 1 refers to expression of one of the three markers (TNF-α, IFN-γ and CD107a), circle 2 refers to expression of the two of the three markers, and circle 3 refers to expression of all three markers. (B) Reference antigen presenting scaffold with the ratio 1:8:8:8 (scaffold:pMHC:IL-2:IL-21).

Figure 15A:
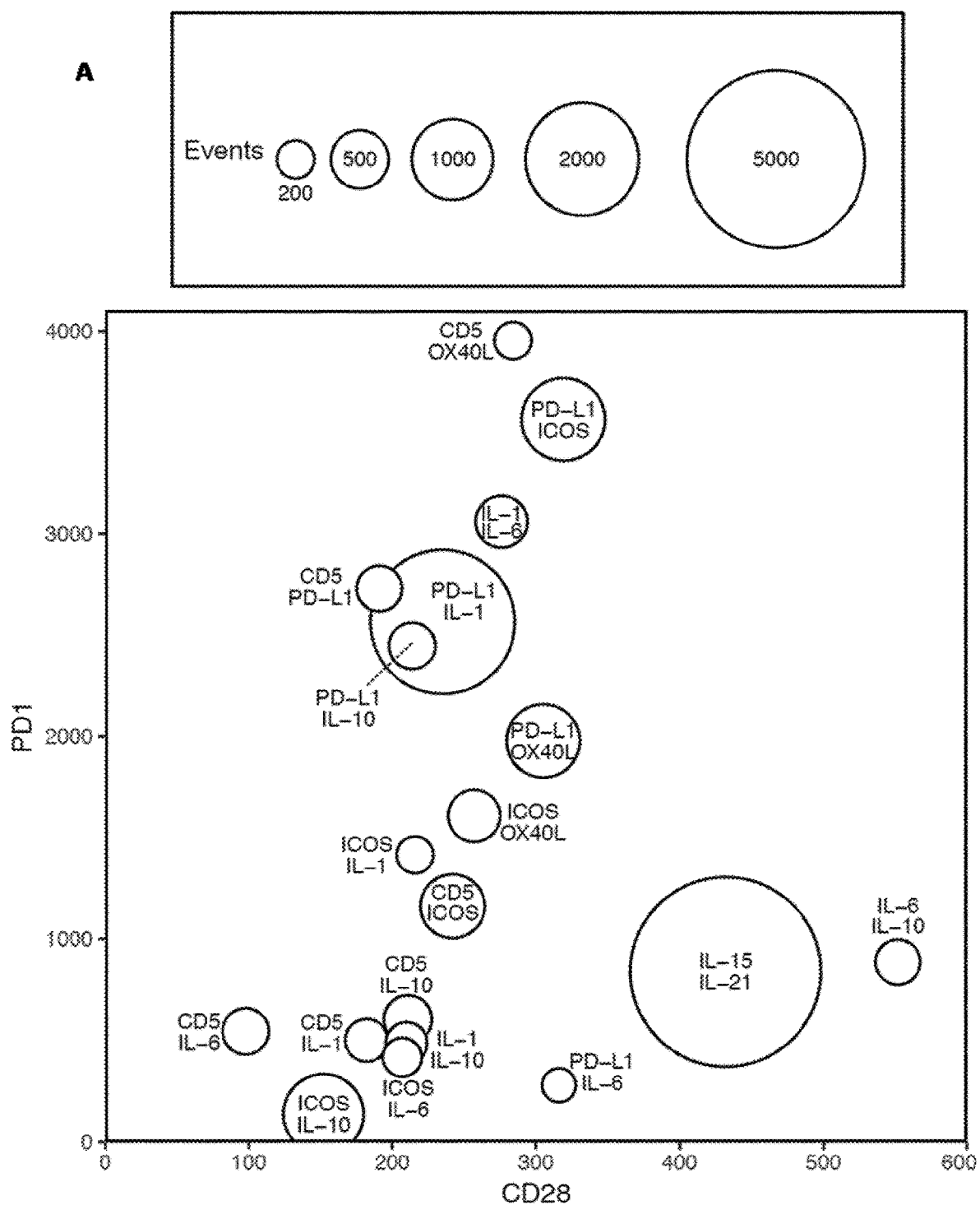
Figure 15B:
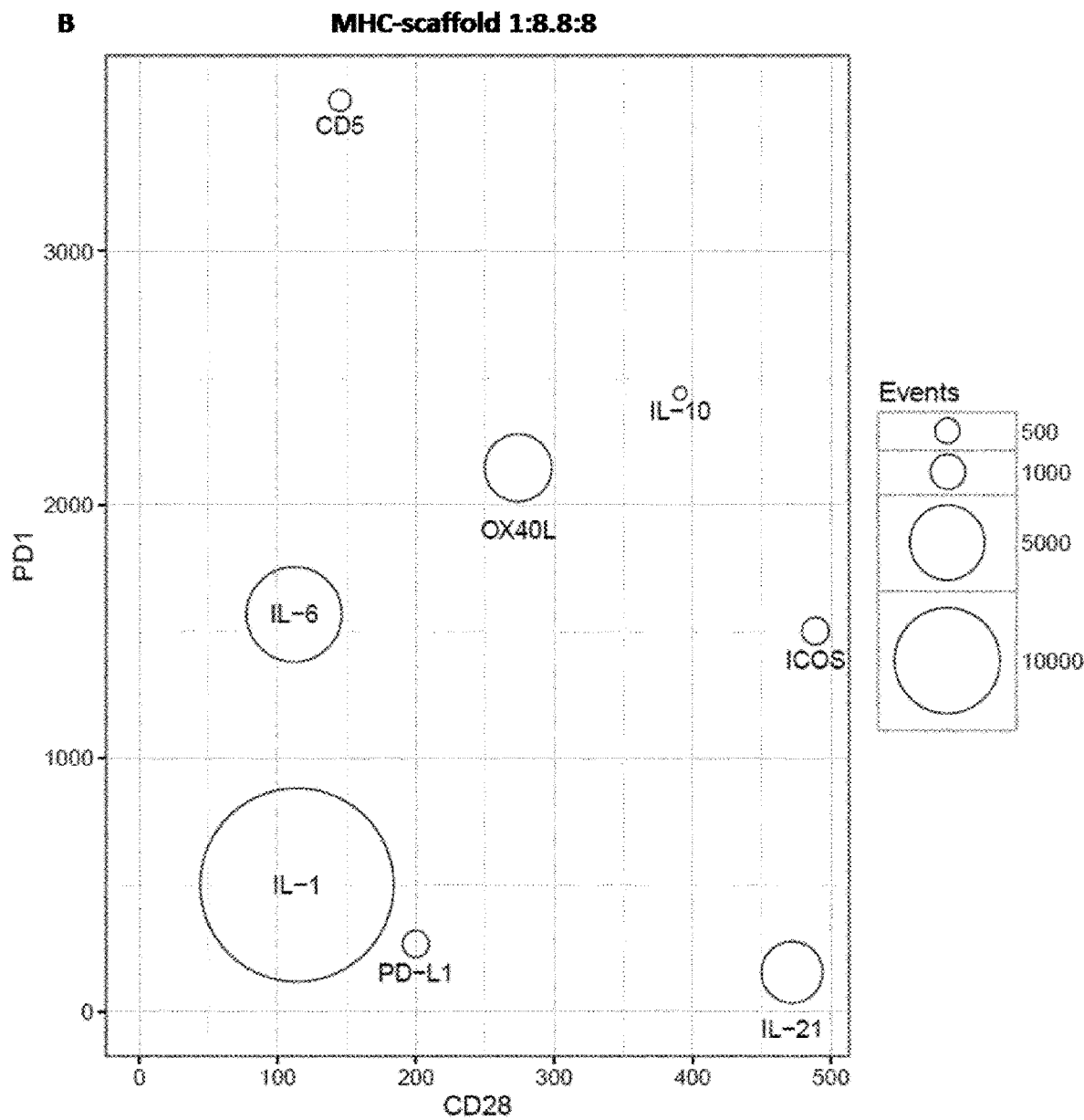

FIG. 15 shows CD28 and PD-1 expression of HLA-A2 EBV LMP2 CLG specific CD8 T cells after 2 weeks expansion with (A) 19 different antigen presenting scaffolds with ratio 1:10:5:5:5 (scaffold:pMHC:B7-2:molecule 1:molecule 2) and a reference antigen presenting scaffold (scaffold:pMHC:B7-2:IL-15:IL-21), and (B) seven antigen presenting scaffold with ratio 1:8:8:8 (scaffold:pMHC:IL-2:molecules 1) and a reference antigen presenting scaffold (scaffold:pMHC:IL-2:IL-21) without IL-2 in the culture media. The black circle represents the absolute number of antigen-specific CD8 T cells (events) detected with tetramer staining, the relative distribution on the x- and y-axes represents their expression of the two molecules, PD-1 and CD28. PD-1 and CD28 antibodies were both BV-421 labeled.

Figure 16:
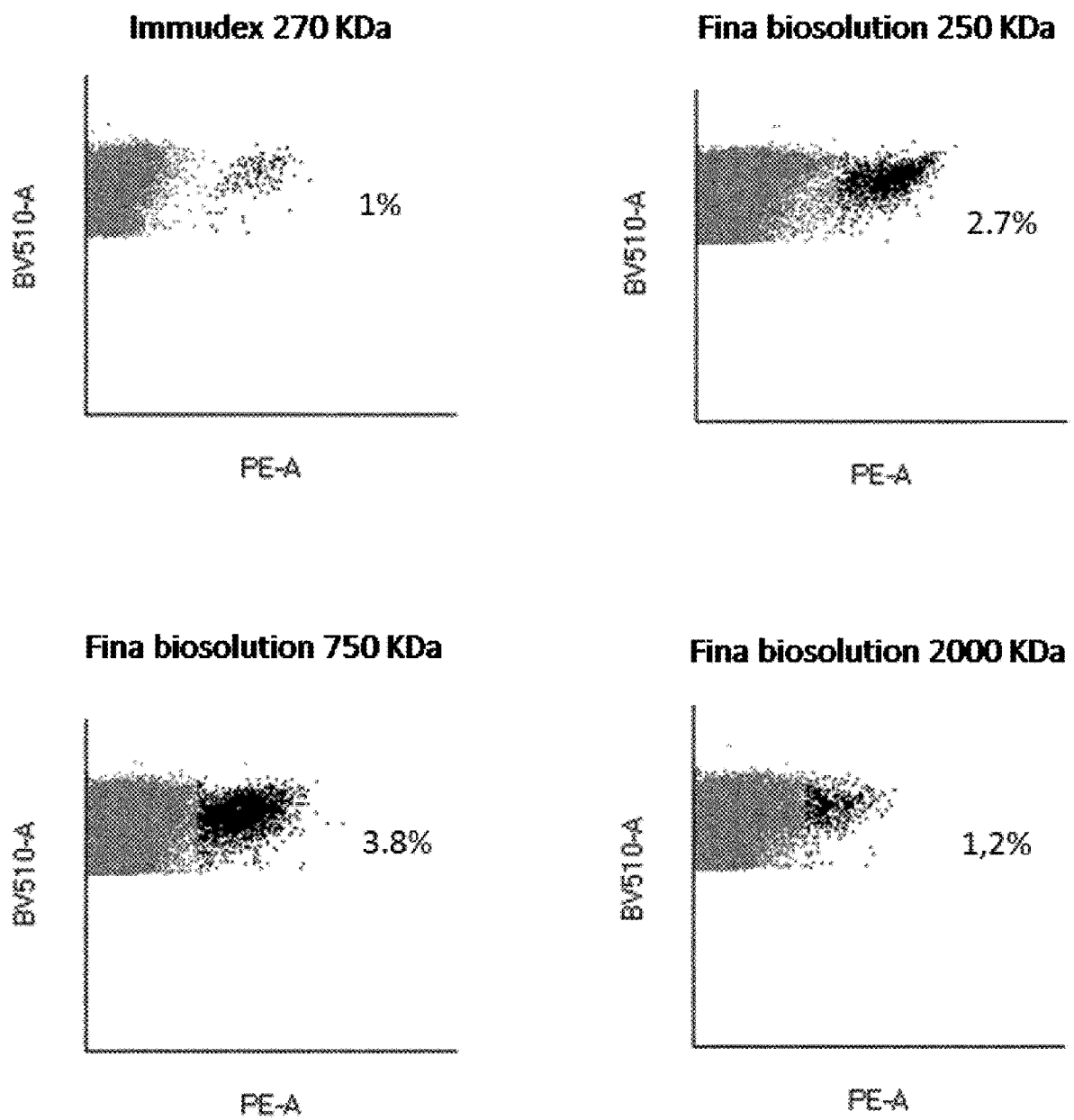

FIG. 16 shows frequency of HLA-A2 EBV LMP2 CLG specific CD8 T cells from a healthy donor detected by tetramer staining after two weeks stimulation with antigen presenting scaffolds, assembled with different scaffold length of 270 kDa from Immudex, and 250 kDa, 750 kDa, and 2000 kDa from Fina Biosolutions. The scaffolds were assembled with the ratio 1:10:5:5:5 (scaffold:pMHC:B7-2:IL-15:IL-21). CD8 antibody is BV510 labeled (Y-axis) and the tetramer is PE labeled (X-axis). The baseline response of the HLA-A2 EBV LMP2 CLG specific CD8 T cells was 0.01%.

FIG. 17 shows parallel expansion of antigen specific CD8 T cells from a healthy donor, with five different known virus responses using aAPC scaffold 1:8:8:8 (scaffold:pMHC:IL-2:IL-21). (A) Two of the five different virus responses (HLA-A2 EBV LMP2 FLY and HLA-A2 CMV pp65 NLV specific CD8 T cells) were respectively expanded either individually or as a mixture of $\frac{1}{10}$ the specific aAPC scaffold plus $\frac{9}{10}$ of aAPC scaffold with irrelevant non-matching HLA-types. (B) All five virus responses were expanded simultaneously in the same culture, using $\frac{1}{10}$ of the normal aAPC scaffold concentration for each specificity, plus $\frac{5}{10}$ of aAPC scaffolds with non-matching HLA-type. The specificity of the five virus responses are respectively, HLA-A2 FLU MP 58-66 GIL, HLA-A2 EBV LMP2 FLY, HLA-A2 CMV pp65 NLV, HLA-A2 EBV BRLF1 YVL, and HLA-A2 CMV IE1 VLE.

FIG. 18 shows the frequency of antigen-specific CD8 T cells from a healthy donor after 2 weeks expansion with aAPC scaffolds of 250 KDa, 750 KDa, and 2000 KDa. Two different scaffold to molecule ratios were used for all three scaffolds, (A) aAPC scaffold 1:8:8:8 (scaffold:pMHC:IL-2:IL-21), and (B) aAPC scaffold 1:24:24:24 (scaffold:pMHC:IL-2:IL-21).

Figure 19:
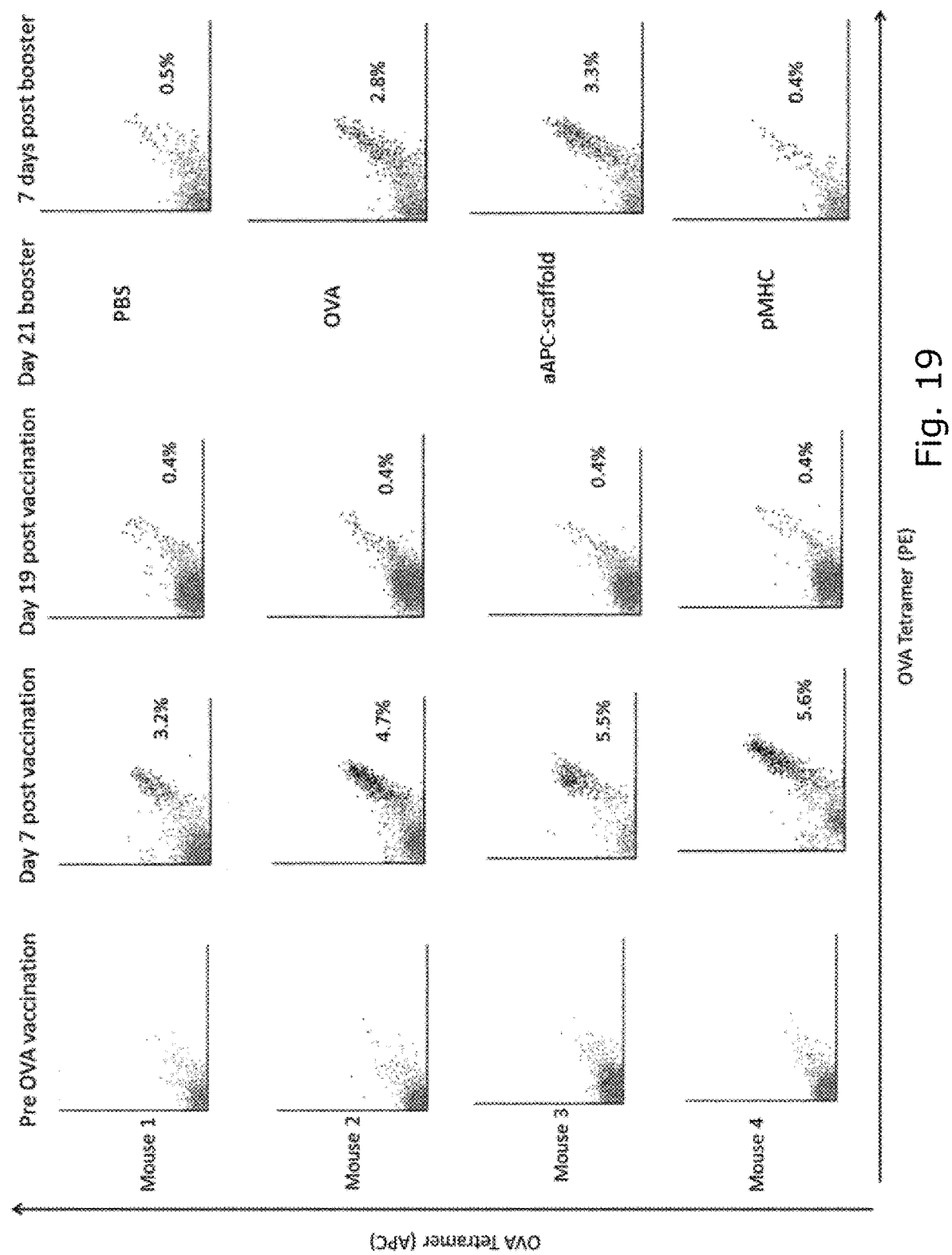

FIG. 19 shows aAPC scaffold-mediated in vivo expansion of OVA-specific CD8 T cells in C57BL/6 mice. Frequency of OVA-specific CD8 T cells were measured pre vaccination, on day 7 and day 19 after i.p. vaccination with OVA+poly IC and day 7 after booster. Four different boosters were administrated on day 21 post vaccination. Mouse 1 had PBS i.v., mouse 2 had OVA i.p., mouse 3 had aAPC scaffold 1:8:8:8 with the H2-Kb/SIINFEKL (scaffold:pMHC:IL-2:IL21) i.v., and mouse 4 had H2-Kb/SIINFEKL in the same concentration as assembled on the aAPC scaffold 1:8:8:8 i.v. (i.e. the booster for mouse 3). I.e. in mouse 4, the antigenic peptide was given as part of a pMHC complex, but without the aAPC scaffold.

FIG. 20 shows a comparison of aAPC scaffold-mediated expansion versus monocyte-derived dendritic cells (moDC)-mediated expansion of antigen-specific T cells. Antigen-specific T cells were expanded from a healthy donor with initially 0.01% antigen-specific T cells. The expansion was done under four conditions in parallel in the presence of either (A) free pMHC complex and IL2 and IL21 (i.e. without the aAPC scaffold), (B) aAPC scaffold ratio 1:8:8:8 (scaffold:pMHC:IL-2:IL-21), (C) unpulsed moDC's or (D) peptide pulsed moDC's derived from the same. Antigen-specific T cells subjected to either of the four conditions were cultured for 2 weeks, stimulated as indicated twice a week. The expansion of antigen-specific T cells was traced by MHC tetramer staining after two weeks. Representative dot plots are shown in FIG. 20.

The present invention will now be described in more detail in the following.

DETAILED DESCRIPTION OF THE INVENTION

Definitions

Prior to discussing the present invention in further detail, the following terms and conventions will first be defined:

Artificial Antigen Presenting Cell (aAPC) Scaffold

In the present context, the term "artificial antigen presenting cell (aAPC) scaffold" means an assembly of the necessary molecules as defined herein to function similar to an antigen presenting cell.

Polymeric Backbone

In the present context, the term "polymeric backbone" means the part of the aAPC scaffold onto which the individual template molecules are fixed. The template molecules are attached by means of an interaction between a coupling agent located on or as an integrated part of the polymeric backbone and an affinity tag placed on the template molecule. Alternatively, the coupling agent may be on the template molecule, with the corresponding affinity tag being on the polymeric backbone.

The polymeric backbone may be of a material selected from polysaccharides, vinyl polymers, poly ethylene glycol, poly propylene glycol, strep-tactin, poly-streptavidin, biotin-binding proteins and polyhistidine-binding polymers.

Template Molecules

In the present context, the term "template molecule" refers to any molecule attached onto the polymeric backbone of the aAPC scaffold. They may be selected from pMHC molecules, cytokines, co-stimulatory molecules and CD47. Template molecules comprise an affinity tag.

Non-Covalent Interaction

In the present context, the term "non-covalent interaction" means any bonding via other interactions than a covalent bond. A non-covalent bond may be formed by e.g. hydrophobic interactions, hydrophilic interactions, ionic interactions, van der walls forces, hydrogen bonding, and combinations thereof.

Coupling Agent

In the present context, the term "coupling agent" refers to a molecular entity positioned on the polymeric backbone of the aAPC. A coupling agent can be non-covalently bound to an affinity tag. Examples of coupling agents include streptavidin, avidin, strep-tactin, antibodies, poly His-tags, metal ion chelates etc.

Alternatively, the coupling agent may be on the template molecule, with the corresponding affinity tag being on the polymeric backbone.

Affinity Tag

In the present context, the term "affinity tag" refers to a molecular species located on a template molecule. An affinity tag binds highly specifically to a coupling agent by non-covalent interaction. Examples of coupling agents include biotin, antibody epitopes, His-tags, streptavidin, strep-tactin, polyhistidine, peptides, metal ion chelates etc.

Alternatively, the affinity tag may be on the polymeric backbone, with the corresponding coupling agent being on backbone the template molecule.

Antigen

In the present context, the term "antigen" refers to a molecule that is capable of inducing an immune response, either by itself or in co-operation with other molecules.

The aAPC as defined herein comprises at least one antigen. The antigen(s) are part of the aAPC, either as i) independent molecules or ii) as part of a complex of molecules. In the case of i), the antigen may be a protein, such as a cluster of differentiation (CD) protein. In the case of ii), the antigen may be a protein or in the form of an antigenic peptide. Such antigenic peptide may be part of a complex with the major histocompatibility complex (MHC), namely a pMHC complex.

The antigen may be a MHC presented antigenic peptide or an antigen that is recognized without being bound to the MHC complex (i.e. non-MHC presented molecule). Examples of antigens not presented in complex with MHC include, but are not limited to, CD proteins, such as CD19, CD20 and CD22.

Haptens

In the present context, the term "haptens" refers to small molecules that can elicit an immune response only when attached to a large carrier, such as a protein or a scaffold. Thus, haptens are low molecular weight and non-immunogenic compounds that may be bound by antibodies, but do not elicit an immune response on its own. Haptens may be conjugated to a disease-targeted antibody.

Examples of haptens include, but are not limited to, biotin, fluorescein, digoxigenin, dinitrophenol, cotinine, hydralazine and urushiol.

MHC and pMHC

In the present context, the terms "MHC" and "pMHC" are used interchangeably and refer to major histocompatibility complex (MHC) molecules with an antigenic peptide complexed.

In humans, the MHC complex is encoded by the human leukocyte antigen (HLA) gene complex. Thus, in the present context, the term "MHC" encompass also "HLA".

Cytokine

In the present context, the term "cytokine" means an immune-regulatory molecule that affects expansion, survival and effector function of stimulated T cells. Cytokines include chemokines, interferons, interleukins, lymphokines, and tumor necrosis factors.

Gamma-Chain Receptor Cytokines

In the present context, the term "gamma-chain receptor cytokines" refers to the group of cytokines that bind to a corresponding cytokine receptor comprising the common gamma-chain subunit. The common gamma-chain ($\gamma_c$) receptor is also known as CD132 or interleukin-2 receptor subunit gamma (IL-2RG). One common denominator for the gamma-chain receptor cytokines is that they all deliver their intracellular signal through the shared gamma-chain receptor and influence T-cell activation and differentiation.

The $\gamma_c$ glycoprotein is a transmembrane protein, which comprises extracellular, transmembrane and intracellular domains and is typically expressed on lymphocytes. The $\gamma_c$ subunit is part of the receptor complexes of at least six different cytokine receptors, namely the IL-2, IL-4, IL-7, IL-9, IL-15 and IL-21 receptors. Therefore, the group of gamma-chain receptor cytokines comprises at least IL-2, IL-4, IL-7, IL-9, IL-15 and IL-21.

Co-Stimulatory Molecule

In the present context, the term "co-stimulatory molecule" means a molecule that upon interaction with T cells enhances T cell response, proliferation, production and/or secretion of cytokines, stimulates differentiation and effector functions of T cells or promotes survival of T cells relative to T cells not contacted with a co-stimulatory molecule. Examples of co-stimulatory molecules include 67.1, B7.2, ICOS, PD-L1, a-galactosylceramide etc.

Epitope

In the present context, the term "epitope" means the antigenic determinant recognized by the TCR of the T cell. The epitope presented by the pMHC is highly specific for any foreign substance and the interaction with the TCR ensures effective expansion and functional stimulation of the specific T cells in a peptide-MHC-directed fashion.

Pharmaceutical Composition

In the present context, the term "pharmaceutical composition" refers to a composition comprising an expanded T cell population obtained according to the invention, suspended in a suitable amount of a pharmaceutical acceptable diluent or excipient and/or a pharmaceutically acceptable carrier.

Pharmaceutically Acceptable

In the present context, the term "pharmaceutically acceptable" refers to molecular entities and compositions that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopoeia or other generally recognized pharmacopoeia for use in animals, and more particularly in humans.

Adjuvant

In the present context, the term "adjuvant" refers to a compound or mixture that enhances the immune response to an antigen. An adjuvant can serve as a tissue depot that slowly releases the antigen and as a lymphoid system activator, which non-specifically enhances the immune response. Often, a primary challenge with an antigen alone, in the absence of an adjuvant, will fail to elicit a humoral or cellular immune response. Adjuvants include, but are not limited to, complete Freund's adjuvant, incomplete Freund's adjuvant, saponin, mineral gels such as aluminum hydroxide, surface active substances such as lysolecithin, pluronic polyols, polyanions, peptides, oil or hydrocarbon emulsions, keyhole limpet hemocyanins, dinitrophenol, and potentially useful human adjuvants such as BCG (bacille Calmette-Guerin) and *Corynebacterium parvum*. Preferably, the adjuvant is pharmaceutically acceptable.

Excipient

In the present context, the term "excipient" refers to a diluent, adjuvant, carrier, or vehicle with which the composition of the invention is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin.

Artificial Antigen Presenting Cell (aAPC) Scaffold

T cells play a crucial role in the immune response, where they recognize and respond to foreign substances by interacting with antigen presenting cells (APC), displaying antigenic peptides of the foreign substance in complex with MHC molecules (pMHC). The T cells are very specific and express only a single specificity of T cell receptor (TCR), thereby allowing the T cell only to recognize and respond to a single specific pMHC molecule. When the T cells are first primed to develop receptors of a specific combination of antigen and MHC molecule, they will not subsequently be able to recognize other specificities. This specialization of the T cell is called MHC restriction and can be utilized to expand T cells of a single specificity without any irrelevant specificities "polluting" the expanded T cell population.

Some gene-modified immune cells, such as CAR T cells, recognize antigens that are not presented by MHC molecules. The present invention may be utilized for expansion of cells recognizing any type of antigen.

Thus, the aAPC may comprise any antigen that is capable of inducing an immune response, either by itself or in co-operation with other molecules. Such an antigen may be a protein, such as a cluster of differentiation (CD) protein.

MHC molecules exist in several variants, of which MHC class I and MHC class II molecules may be regarded as the most important. The MHC class I molecules interact with CD8 positive cytotoxic T cells (CD8+ T cells) and MHC class II molecules interact with CD4 positive helper T cells (CD4+ T cells). Once activated CD8+ T cells generally seek to kill cancer cells, cells that are infected (particularly with viruses), or cells that are damaged in other ways. CD4+ T cells on the other hand mainly function by assisting the immune system, e.g. by releasing cytokines and potentiate the CD8 T cells. Although not limited to a single type of T cell, the present invention is mainly concerned with the activation, stimulation and expansion of CD8+ T cells. This is particularly true since the utilization of an aAPC scaffold, to some extent, fulfills the role of the CD4+ T cells. However, the aAPC scaffolds as described herein may be utilized to expand both CD4+ T cells and CD8+ T cells.

Although the TCR-pMHC interaction is the main driver for the activation of T cells, several other stimuli are required to prepare the T cells for an effective immune response. Overall, the activation of CD8+ T cells requires two signals; 1) the interaction between the TCR and the pMHC class I molecule and 2) a co-stimulatory interaction between CD28, a membrane receptor on T-cells, and CD28 ligands located on the APC, such as B7.1 (CD80) or B7.2 (CD86). The second signal serves to enhance proliferation, cytokine production and cell survival.

In addition to the stimulatory signals, T cell response is also regulated by inhibitory signals. Tim-3, LAG-3 and PD-1 are examples of mediators of inhibitory signals. They serve as a natural mechanism to avoid excessive T cell activation and prevent the immune system from running rampant across the organism.

The secondary signal may be assisted, or in some cases replaced, by stimulation of the CD8+ T cell with cytokines released by CD4+ T cells. Thus, cytokines constitute another important group of molecules involved in the modulation of the immune response. Cytokines generally include interleukins, interferons, chemokines, lymphokines, and tumor necrosis factors. They act through receptors and amongst others regulate the maturation, growth, and responsiveness of T cell populations. Together, interleukin-2 (IL-2) and the co-stimulatory signals are the most crucial factors for preservation of continuous cell division. The delicate interplay between co-stimulatory molecules and cytokines is complex and one of the key factors of efficient and specific T cell expansion.

Another molecule that plays a key role in immune responses as well as in cellular processes, such as apoptosis, proliferation, adhesion, and migration, is CD47. This transmembrane protein is ubiquitously expressed in human cells, but is also overexpressed in many different tumor cells, with high levels of CD47 allowing the cancer cells to avoid phagocytosis. However, CD47 is also widely expressed in immune cells, functioning as a "don't eat me" signal that prolongs the circulation time of the immune cells. Expansion of T cells that express CD47 may be preferable as these cells are forecasted to have an increased half-life when used therapeutically.

Therefore, an embodiment of the present invention relates to the aAPC scaffold as described herein, wherein the template molecules comprise a ligand capable of stimulating CD47 expression in a T cell population.

CD47 may also infer beneficial properties to the aAPC itself, e.g. as a "don't eat me" signal that prolongs the half-life of the aAPC scaffold in culture or in circulation.

Thus, an embodiment of the present invention relates to the aAPC scaffold as described herein, wherein the template molecules comprise at least one CD47 molecule.

As exemplified by the above description, there are many factors involved in the activation and proliferation of T cells. However, for the purpose of immune therapy and/or expansion of a specific T cell population, it is possible to set some conditions that should ideally be fulfilled for the ability to provide a T cell population with high activity and functionality suited for these purposes. Thus, preferable characteristics of the expanded T cells include:

a. high expression of activators (such as CD28)
b. low expression of inhibitors (such as PD1)
c. a multifunctional cytokine response The cluster of different molecules required for efficient activation and stimulation has to be present simultaneously to provide the optimal capacity for T cell function and expansion. The use of an aAPC scaffold collects the combination of required molecules in a defined proximity to each other and thus constitutes a suitable platform for efficient expansion of the specific T cells.

Thus, the present invention demonstrates specific conditions required to expand tumor-reactive T cells, through use of MHC-loaded aAPC scaffolds to provide the cells with specific functional stimulation to obtain phenotypic and functional properties ideal to mediate tumor regression or viral clearance. These aAPC scaffolds are constructed from a polymeric backbone conjugated with coupling agents to which affinity tagged peptide-MHC (pMHC) molecules are attached to govern the specific interaction with a specific T cell, and a combination of likewise affinity tagged cytokines and co-stimulatory molecules are co-attached to provide stimulation of the specific T cells to achieve increased functional properties. The aAPC scaffolds will specifically interact with T cells based on recognition of the pMHC molecule, and can through this specific interaction effectively expand and functionally stimulate specific T cells in a peptide-MHC-directed fashion.

The aAPC scaffolds may be assembled by combinations of a large variety of different template molecules (i.e. pMHC molecules, cytokines and co-stimulatory molecules). The aAPC scaffolds described herein may comprise one or more co-stimulatory molecules including, but not limited to, CD2, CD3, CD4, CD5, CD7, CD8, CD9, CD27, CD28, CD30, CD40, CD48, CD58, CD69, CD70, CD72, B7.1 (CD80), CD83, B7.2 (CD86), Fas (CD95), OX40 (CD134), CD137 (4-1BB), CD147, SLAM (CDw150), CTLA-4 (CD152), CD153 (CD30L), CD40L (CD154), inducible T-cell co-stimulator (ICOS, CD278), CD134L, CD137L, OX40L, NKG2D, HVEM, PD-1, B7RP-1, PD-L1, PD-L2, intercellular adhesion molecule (ICAM) and ICOSL.

Furthermore, the aAPC scaffolds described herein may comprise one or more cytokines including, but not limited to interleukin-1 (IL-1), interleukin-2 (IL-2), interleukin-3 (IL-3), interleukin-4 (IL-4), interleukin-5 (IL-5), interleukin-6 (IL-6), interleukin-7 (IL-7), interleukin-8 (IL-8), interleukin-10 (IL-10), interleukin-12 (IL-12), interleukin-15 (IL-15), interleukin-21 (IL-21), interferon alpha (IFN-α), interferon beta (IFN-β), interferon gamma (IFN-γ), IGIF, granulocyte macrophage colony stimulating factor (GM-CSF), tumor necrosis factor alpha (TNF-α), tumor necrosis factor beta (TNF-β) and macrophage colony stimulating factor (M-CSF), and variants and fragments thereof.

Herein are described aAPC scaffolds suitable for T cell expansion, ensuring a high ratio of active T cells, high antigen specificity of the T cells and high functionality of the T cells. Consequently, a first aspect of the present invention relates to an artificial antigen presenting cell (aAPC) scaffold comprising a polymeric backbone to which are attached the following template molecules:
  i. at least one major histocompatibility complex molecule comprising an antigenic peptide (pMHC),
  ii. at least one cytokine selected from the group consisting of IL-21, IL-2, IL-15, IL-1, IL-6, IL-10 and IL-7,
  iii. optionally, at least one co-stimulatory molecule selected from the group consisting of B7.2 (CD86), B7.1 (CD80), CD40, ICOS and PD-L1, and
  iv. optionally, at least one CD47 molecule.

The expansion of some T cells may be enhanced when several cytokines are present simultaneously. Thus, an embodiment of the present invention relates to the aAPC scaffold as described herein, wherein the template molecules comprise at least two different cytokines selected from the group consisting of IL-21, IL-2, IL-15, IL-1, IL-6, IL-10 and IL-7.

The aAPC according to the present invention may also comprise antigens that are recognized without being bound to the MHC complex. Such antigens may be, but are not limited to, proteins belonging to the cluster of differentiation (CD) classification.

Different groups of cytokines have been identified to produce especially favorable aAPC scaffolds. Without being bound by theory, one efficient group of cytokines are cytokines that deliver their intracellular signal through the shared gamma-chain receptor and influence T-cell activation and differentiation. In the present context, these cytokines are termed "gamma-chain receptor cytokines". Therefore, a preferred aspect of the invention relates to an artificial antigen presenting cell (aAPC) scaffold comprising a polymeric backbone to which are attached the following template molecules:
  i. at least two different gamma-chain receptor cytokines, such as at least two different gamma-chain receptor cytokines selected from the group consisting of IL-21, IL-2, IL-15, IL-4, IL-9 and IL-7,
  ii. at least one antigen,
  iii. optionally, at least one co-stimulatory molecule selected from the group consisting of B7.2 (CD86), B7.1 (CD80), CD40, ICOS and PD-L1, and
  iv. optionally, at least one CD47 molecule.

Another embodiment of the present invention relates to the aAPC scaffold as described herein, wherein the group of gamma-chain receptor cytokines consist of IL-2, IL-4, IL-7, IL-9, IL-15 and IL-21.

Yet another embodiment of the present invention relates to the aAPC scaffold as described herein, wherein the gamma-chain receptor cytokines are selected from the group consisting of IL-21, IL-2, IL-15, IL-4, IL-9 and IL-7.

The inventors have identified preferred combinations of stimulatory molecules within the gamma-chain receptor cytokine family.

Thus, an embodiment of the present invention relates to the aAPC scaffold as described herein, wherein the gamma-chain receptor cytokines are selected from the group consisting of IL-21, IL-2 and IL-15.

Another embodiment of the present invention relates to the aAPC scaffold as described herein, wherein the gamma-chain receptor cytokines comprise at least IL-21.

Yet another embodiment of the present invention relates to the aAPC scaffold as described herein, wherein the gamma-chain receptor cytokines comprise:
  i. at least IL-2 and IL-21, or
  ii. at least IL-15 and IL-21.

A further embodiment of the present invention relates to the aAPC scaffold as described herein, wherein the gamma-chain receptor cytokines are:
  i. IL-2 and IL-21, or
  ii. IL-15 and IL-21.

Another embodiment of the present invention relates to the aAPC scaffold as described herein, wherein the gamma-chain receptor cytokines comprise:
  i. at least IL-4 and IL-21,
  ii. at least IL-7 and IL-21, or
  iii. at least IL-9 and IL-21.

Yet another embodiment of the present invention relates to the aAPC scaffold as described herein, wherein the gamma-chain receptor cytokines are:
  i. IL-4 and IL-21,
  ii. IL-7 and IL-21, or
  iii. IL-9 and IL-21.

The antigen may be a MHC presented antigenic peptide or an antigen that is recognized without being bound to the MHC complex (i.e. non-MHC presented molecule). Antigens that are not bound to a MHC complex may be any type of protein that is capable of inducing an immune response.

Thus, an embodiment of the present invention relates to the aAPC scaffold as described herein, wherein the at least one antigen is a non-MHC presented molecule.

A relevant class of non-MHC presented antigens are cluster of differentiation (CD) proteins. CD proteins are a group of cell surface molecules commonly recognized as targets for cellular immunophenotyping and may act as receptor or ligands in signal cascades of importance to cell signaling. CD proteins may be included in aAPCs specifically designed to stimulate and expand chimeric antigen receptor (CAR) T cells. Examples of relevant CD proteins include, but is not limited to, CD19, CD20, CD22 and CD269.

Another relevant class of antigens are haptens or organic small molecules, such as, but not limited to, biotin, fluorescein, digoxigenin, dinitrophenol, cotinine, hydralazine and urushiol. The hapten may be conjugated to a disease targeted antibody. CAR T platforms using anti-hapten CAR T cells in combination with hapten-conjugated anti-cancer antibodies has been proposed as a novel way to target multiple cancer-antigens using single CAR T cells.

An embodiment of the present invention relates to the aAPC scaffold as described herein, wherein the antigen is a non-MHC presented molecule selected from the group consisting of CD19, CD20, CD22, CD269, haptens, BCMA, epidermal growth factor receptor (EGFR), mesothelin (MSLN), variant III of the epidermal growth factor receptor (EGFRvIII), human epidermal growth factor receptor-2 (HER2), carcinoembryonic antigen (CEA), and prostate-specific membrane antigen (PSMA).

A further embodiment of the present invention relates to the aAPC scaffold as described herein, wherein the non-MHC presented molecule is a CD protein.

CD proteins may be included in aAPCs specifically designed to stimulate and expand chimeric antigen receptor (CAR) T cells. Examples of relevant CD proteins include, but is not limited to, CD19, CD20, CD22 and CD269.

Therefore, an embodiment of the present invention relates to the aAPC scaffold as described herein, wherein the CD protein is selected from the group consisting of CD19, CD20, CD22 and CD269.

Another embodiment of the present invention relates to the aAPC scaffold as described herein, wherein the non-MHC presented molecule is a hapten.

A further embodiment of the present invention relates to the aAPC scaffold as described herein, wherein the hapten is attached to an antibody.

Another embodiment of the present invention relates to the aAPC scaffold as described herein, wherein the antigen is a major histocompatibility complex molecule comprising an antigenic peptide (pMHC).

The template molecules may be attached to the polymeric backbone via the interaction between coupling agents and affinity tags. Coupling agents are located on the polymeric backbone of the aAPC scaffold and may be attached to the backbone by, but not limited to, hydrophobic interactions, electrostatic interactions or covalent bonding. When positioned on the polymeric backbone, the coupling agents provide a flexible template to which affinity-tagged template molecules may be fixed in a modular fashion. Affinity tags are molecular species that bind specifically to the coupling agent through, but not limited to, non-covalent interactions. By attaching an affinity tag to each template molecule, it is therefore easy to assemble a custom-built aAPC scaffold.

Thus, an embodiment of the present invention relates to the aAPC scaffold as described herein, wherein the template molecules are attached to the polymeric backbone via non-covalent interactions between a coupling agent located on the polymeric backbone and an affinity tag on the template molecule.

Many known compatible pairs of affinity tags and couplings agents may be used with the present invention and include, but are not limited to, biotin/streptavidin, biotin/avidin, biotin/neutravidin, biotin/strep-tactin, poly-His/metal ion chelate, peptide/antibody, glutathione-S-transferase/glutathione, epitope/antibody, maltose binding protein/amylase and maltose binding protein/maltose. Other known compatible pairs of affinity tags and couplings agents may also be used with the present invention.

Thus, an embodiment of the present invention relates to the aAPC scaffold as described herein, wherein the coupling agent/affinity tag is selected from the group consisting of biotin/streptavidin, biotin/avidin, biotin/neutravidin, biotin/strep-tactin, poly-His/metal ion chelate, peptide/antibody, glutathione-S-transferase/glutathione, epitope/antibody, maltose binding protein/amylase and maltose binding protein/maltose.

Another preferred embodiment of the present invention relates to the aAPC scaffold as described herein, wherein the coupling agent is streptavidin and the affinity tag is biotin.

The polymeric backbone of the aAPC scaffold to which the template molecules are attached may also be based on a variety of different materials. Thus, several types of types of backbones may be used with the present invention, including, but not limited to, polysaccharides, synthetic polysaccharides, vinyl polymers, poly ethylene glycol, poly propylene glycol, derivatised cellulosics, strep-tactin and poly-streptavidin. Polysaccharides may be dextran or different variants of dextrans, such as carboxy methyl dextran, dextran polyaldehyde, and cyclodextrins. An example of a synthetic polysaccharide is e.g. ficoll. Vinyl polymers include, but are not limited to, poly(acrylic acid), poly (acrylamides), poly(acrylic esters), poly(methyl methacrylate), poly(maleic acid), poly(acrylamide), poly(methacrylic acid) and poly(vinylalcohol). Polymeric backbones consisting of derivatised cellulosics include, but are not limited to, derivatised cellulosics including carboxymethyl cellulose, carboxymethyl hydroxyethyl cellulose and hydroxy-ethyl cellulose.

Additionally, there exist commercially available polymeric backbones that can serve as the basis for forming self-assembling aAPC scaffolds according to the present invention. These polymeric backbones include, but are not limited to, the Streptamers from IBA GmbH and Beckman Coulter, which are based on the Strep-tactin protein that oligomerizes to form a multimer capable of binding several biotinylated molecules such as biotinylated pMHC complexes, cytokines and co-stimulatory molecules.

Thus, an embodiment of the present invention relates to the aAPC scaffold as described herein, wherein the polymeric backbone is selected from the group consisting of polysaccharides, vinyl polymers, poly ethylene glycol, poly propylene glycol, strep-tactin and poly-streptavidin.

Another embodiment of the present invention relates to the aAPC scaffold as described herein, wherein the polymeric backbone is a polysaccharide.

A further and preferred embodiment of the present invention relates to the aAPC scaffold as described herein, wherein the polysaccharide is dextran.

The size of the polymeric backbone sets the physical limits to how many template molecules that can be attached to each aAPC scaffold. The size of the polymeric backbone is given by its molecular weight.

Therefore, an embodiment of the present invention relates to the aAPC scaffold as described herein, wherein the dextran has a molecular weight in the range of 50-3000 kDa, such as 100-2500 kDa, such as 250-2500 kDa.

Another embodiment of the present invention relates to the aAPC scaffold as described herein, wherein the dextran has a molecular weight selected from the group of consisting of 250 kDa, 270 kDa, 750 kDa, and 2000 kDa.

In addition to the number of molecules attached to each aAPC scaffold, another important parameter is the density with which the template molecules are distributed on the polymeric backbone. The density may be varied by adjusting the ratio between all molecules comprised by the aAPC scaffold. Thus, an embodiment of the present invention relates to the aAPC scaffold as described herein, wherein the ratio between polymeric backbone:pMHC molecule:co-stimulatory molecule:cytokine is selected from the group consisting of 1:1:1:1, 1:2:1:1, 1:4:1:1, 1:4:2:1, 1:4:2:2, 1:10:5:5, 1:4:4:4, 1:8:8:8, 1:10:10:10, 1:20:20:20, 1:30:30:30, 1:40:40:40, 1:50:50:50, 1:50:10:10 or 1:50:20:20. Another embodiment of the present invention relates to the aAPC scaffold as described herein, wherein the ratio between polymeric backbone:pMHC molecule:cytokine 1:cytokine 2 is selected from the group consisting of 1:1:1:1, 1:2:1:1, 1:4:1:1, 1:4:2:1, 1:4:2:2, 1:10:5:5, 1:4:4:4, 1:8:8:8, 1:10:10:10, 1:20:20:20, 1:30:30:30, 1:40:40:40, 1:50:50:50, 1:50:10:10 or 1:50:20:20.

Still another embodiment of the present invention relates to the aAPC scaffold as described herein, wherein the ratio between polymeric backbone:pMHC molecule:co-stimulatory molecule:cytokine 1:cytokine 2 is selected from the group consisting of 1:1:1:1:1, 1:2:1:1:1, 1:4:1:1:1, 1:4:2:1:1, 1:4:2:2:2, 1:10:5:5:5, 1:4:4:4:4, 1:8:8:8:8, 1:10:10:10:10, 1:20:20:20:20, 1:30:30:30:30, 1:40:40:40:40, 1:50:50:50:50, 1:50:10:10:10 or 1:50:20:20:20.

The present invention may be suitable for expansion of T cells from a variety of subjects. Thus, an embodiment of the present invention relates to the aAPC scaffold as described herein, wherein the at least one pMHC molecule is a vertebrate MHC molecule, such as a human, murine, rat, porcine, bovine or avian molecule.

Another preferred embodiment of the present invention relates to the aAPC scaffold as described herein, wherein the vertebrate MHC molecule is a human molecule.

As described above, MHC molecules exist in several variants. MHC molecules include, but are not limited to, MHC class I molecules, MHC class II molecules, MHC class III molecules, MHC class I like molecules and MHC class II like molecules. MHC class I like molecules include, but are not limited to, CD1a, CD1b, CD1c, CD1d, MICA, MICB, MR1, ULBP-I, ULBP-2, and ULBP-3. MHC class II like molecules include, but are not limited to, HLA-DM, HLA-DO, I-A beta2, and I-E beta2.

Thus, an embodiment of the present invention relates to the aAPC scaffold as described herein, wherein the at least one pMHC molecule is selected from the group consisting of MHC class I molecules, MHC class II molecules, MHC class III molecules, CD1a, CD1b, CD1c, CD1d and MR1.

Another preferred embodiment of the present invention relates to the aAPC scaffold as described herein, wherein the at least one pMHC molecule is a MHC class I molecule.

A further preferred embodiment of the present invention relates to the aAPC scaffold as described herein, wherein the at least one pMHC molecule is a human MHC class I molecule. In humans, the major histocompatibility complex (MHC) is encoded by a gene complex called the human leukocyte antigen (HLA) complex. The HLAs corresponding to MHC class I are called HLA-A, HLA-B and HLA-C.

The antigenic peptide presented by the pMHC molecule ultimately decides which type of T cells will be expanded by the aAPC scaffold—the concept previously referred to as MHC restriction. The antigens used with the present invention may essentially come from any source. The antigenic source may include, but is not limited to, a human, a virus, a bacterium, a parasite, a plant, a fungus, or a tumor. Thus, an embodiment of the present invention relates to the aAPC scaffold as described herein, wherein the antigenic peptide of the pMHC is derived from a source selected from the group consisting of a human, a virus, a bacterium, a parasite, a plant, a fungus, and a tumor.

One use of the aAPC scaffold of the present invention is in the expansion of tumor-reactive T cells for use in adoptive cell transfer (ACT). The strength of the ACT strategy is that T cells are present ex vivo in an environment that, contrary to the local tumor environment, is optimal for efficient expansion of an antigen specific T cell population.

Another potential use of the aAPC scaffold of the present invention is for expansion of a T cell population specific for fighting certain infections that typically arise in the wake of transplantation. Patients receiving transplants are typically subject to immunosuppressive treatment to avoid graft rejection. In many cases, such treatment leaves the patient vulnerable to aggressive viral strains causing severe infections of the already weakened patient. The aAPC scaffold of the present invention is perfectly suited for efficient expansion of T cells extracted from transplantation patients, with the aim of treating any severe infections by the ACT strategy.

Thus, an embodiment of the present invention relates to the aAPC scaffold as described herein, wherein the antigenic peptide of the pMHC is a cancer-associated epitope or virus epitope.

Another embodiment of the present invention relates to the aAPC scaffold as described herein, wherein the antigen comprises a cancer-associated epitope or virus epitope.

An alternative embodiment of the present invention relates to the aAPC scaffold as described herein, wherein the antigenic peptide of the pMHC is a neoepitope, such as a cancer neoepitope.

Another embodiment of the present invention relates to the aAPC scaffold as described herein, wherein the cancer-associated epitope is a virus epitope associated with a virus-induced cancer.

The aAPC scaffold of the present invention functions with any antigenic peptide that may be presented by the pMHC molecules attached to the polymeric backbone. Some indications are preferred in the present invention.

Thus, a preferred embodiment of the present invention relates to the aAPC scaffold as described herein, wherein the virus epitope is from a virus selected from the group consisting of human papillomavirus (HPV), Merkel cell polyomavirus (MCV), cytomegalovirus (CMV), Epstein-Barr virus (EBV), human T-lymphotropic virus (HTLV), hepatitis B virus (HBV), hepatitis C virus (HCV) and influenza virus.

To optimize the efficiency of each aAPC scaffold with regard to the accuracy with which the aAPC scaffold is capable of expanding a single T cell specificity, in one version of the present invention, each aAPC scaffold is only harbouring a single variant of pMHC molecule, i.e. only one peptide antigen is presented for each type of aAPC scaffold.

Therefore, an embodiment of the present invention relates to the aAPC scaffold as described herein, wherein the pMHC molecules are identical and present only a single variant of an antigenic peptide.

By displaying only a single antigenic peptide for each aAPC scaffold, competition between T cells of different specificities is limited to a minimum. If desired, several different scaffolds presenting different peptides may be pooled together and expanded simultaneously. The simultaneous expansion of T cells with a variety of different specificities is possible because competition between T cell is kept at a minimum due to the aAPC scaffold clustering all the template molecules (i.e. the pMHC, co-stimulatory molecules and cytokines) in close proximity to each other. Consequently, the T cell population expanded by use of the aAPC scaffolds of the present invention retain specificity and the pool of different specificities ensures the breadth of any immune response if re-introduced into a subject. This latter characteristic is clinically important to avoid immune escape variants. The breadth of the response may be tuned by deciding how many different aAPC scaffolds are pooled together in a single expansion.

The polymeric backbone may comprise any number of pMHc molecules that is reasonable according to the size of the polymeric backbone. Therefore, an embodiment of the present invention relates to the aAPC scaffold as described herein, wherein each polymeric backbone comprises at least 5 pMHC molecules, such as at least 8, such as at least 10, such as at least 20, such as at least 30, such as at least 40, such as at least 50 or such as at least 100.

An alternative embodiment of the present invention relates to the aAPC scaffold as described herein, wherein each polymeric backbone comprises at least 2 pMHC molecules, such as at least 3 or such as at least 4.

For some applications it may be practical to immobilized the aAPC scaffolds on a solid support, e.g. for certain types of analytics or for separation of the aAPC scaffolds from the expanded T cell population. Thus, an embodiment of the present invention relates to the aAPC scaffold as described herein, wherein said aAPC scaffold is immobilized on a solid support.

Many variants of solid supports exist and may be selected according to the application of the aAPC scaffold. Variants of solid support include, but are not limited to, beads, well plates, particles, micro arrays, membranes, filters, gels and chips. Thus, an embodiment of the present invention relates to the aAPC scaffold as described herein, wherein the solid support is selected from the group consisting of beads, well plates, particles, micro arrays and membranes.

The aAPC scaffold may be attached to the solid support by any conventional means, such as by linkers, antibodies or the like.

A plethora of different template molecules exist and therefore a multiplicity of different aAPC scaffold can be assembled. The inventors have found that certain combinations of template molecules yield especially efficient and preferred aAPC scaffolds.

Thus, an embodiment of the present invention relates to the aAPC scaffold as described herein, wherein the template molecules comprise at least IL-21.

Another embodiment of the present invention relates to the aAPC scaffold as described herein, wherein the template molecules comprise at least IL-15 and IL-21.

Yet another embodiment of the present invention relates to the aAPC scaffold as described herein, wherein the template molecules comprise at least B7.2 (CD86).

Still another embodiment of the present invention relates to the aAPC scaffold as described herein, wherein
i. the polymeric backbone is dextran,
ii. the co-stimulatory molecule is B7.2 (CD86), and
iii. the cytokines are IL-15 and IL-21.

A further embodiment of the present invention relates to the aAPC scaffold as described herein, wherein
i. the polymeric backbone is dextran,
ii. the gamma-chain receptor cytokines are IL-15 and IL-21, and
iii. the co-stimulatory molecule is B7.2 (CD86).

An even further embodiment of the present invention relates to the aAPC scaffold as described herein, wherein
i. the polymeric backbone is dextran,
ii. the gamma-chain receptor cytokines are IL-15 and IL-21,
iii. the antigen is a major histocompatibility complex molecule comprising an antigenic peptide (pMHC), and
iv. the co-stimulatory molecule is B7.2 (CD86).

Another embodiment of the present invention relates to the aAPC scaffold as described herein, wherein the ratio between pMHC, IL-15, IL-21 and B7.2 (CD86) on the dextran backbone is 2:1:1:1.

Yet another embodiment of the present invention relates to the aAPC scaffold as described herein, wherein the ratio between dextran backbone, pMHC, IL-15, IL-21 and B7.2 (CD86) is 1:10:5:5:5.

A further embodiment of the present invention relates to the aAPC scaffold as described herein, wherein the gamma-chain receptor cytokines are IL-2, IL-15 and IL-21.

An even further embodiment of the present invention relates to the aAPC scaffold as described herein, wherein
i. the polymeric backbone is dextran,
ii. the gamma-chain receptor cytokines are IL-2, IL-15 and IL-21, and
iii. the antigen is a major histocompatibility complex molecule comprising an antigenic peptide (pMHC).

An embodiment of the present invention relates to the aAPC scaffold as described herein, wherein the ratio between dextran backbone, pMHC, IL-2, IL-15 and IL-21 is 1:10:5:5:5.

Yet another embodiment of the present invention relates to the aAPC scaffold as described herein, wherein
i. the polymeric backbone is dextran,
ii. the gamma-chain receptor cytokines are IL-2, IL-15 and IL-21,
iii. the antigen is a major histocompatibility complex molecule comprising an antigenic peptide (pMHC), and
iv. the co-stimulatory molecule is B7.2 (CD86).

Another embodiment of the present invention relates to the aAPC scaffold as described herein, wherein the ratio between dextran backbone, pMHC, IL-2, IL-15, IL-21 and B7.2 (CD86) is 1:10:5:5:5.

Still another embodiment of the present invention relates to the aAPC scaffold as described herein, wherein the template molecules comprise at least IL-6 and IL-10.

A further embodiment of the present invention relates to the aAPC scaffold as described herein, wherein
i. the polymeric backbone is dextran,
ii. the co-stimulatory molecule is B7.2 (CD86), and
iii. the cytokines are IL-6 and IL-10.

A still further embodiment of the present invention relates to the aAPC scaffold as described herein, wherein the ratio between pMHC, IL-6, IL-10 and B7.2 (CD86) on the dextran backbone is 2:1:1:1.

An even further embodiment of the present invention relates to the aAPC scaffold as described herein, wherein the ratio between dextran backbone, pMHC, IL-6, IL-10 and B7.2 (CD86) is 1:10:5:5:5.

An embodiment of the present invention relates to the aAPC scaffold as described herein, wherein the gamma-chain receptor cytokines comprise at least IL-2 and IL-21.

Another embodiment of the present invention relates to the aAPC scaffold as described herein, wherein
i. the polymeric backbone is dextran, and
ii. the cytokines are IL-2 and IL-21.

A further embodiment of the present invention relates to the aAPC scaffold as described herein, wherein
i. the polymeric backbone is dextran, and
ii. the gamma-chain receptor cytokines are IL-2 and IL-21.

An even further embodiment of the present invention relates to the aAPC scaffold as described herein, wherein
i. the polymeric backbone is dextran,
ii. the gamma-chain receptor cytokines are IL-2 and IL-21, and
iii. the antigen is a major histocompatibility complex molecule comprising an antigenic peptide (pMHC).

Yet another embodiment of the present invention relates to the aAPC scaffold as described herein, wherein the ratio between pMHC, IL-2 and IL-21 on the dextran backbone is 1:1:1.

Another embodiment of the present invention relates to the aAPC scaffold as described herein, wherein the co-stimulatory molecules comprise at least B7.2 (CD86).

Still another embodiment of the present invention relates to the aAPC scaffold as described herein, wherein the ratio between dextran backbone, pMHC, IL-2 and IL-21 is 1:8:8:8.

A further embodiment of the present invention relates to the aAPC scaffold as described herein, wherein the polymeric backbone comprises at least IL-1 and PD-L1.

A still further embodiment of the present invention relates to the aAPC scaffold as described herein, wherein
i. the polymeric backbone is dextran,
ii. the co-stimulatory molecules are B7.2 (CD86) and PD-L1, and iii. the cytokine is IL-1.

An even further embodiment of the present invention relates to the aAPC scaffold as described herein, wherein the ratio between pMHC, IL-1, B7.2 (CD86) and PD-L1 on the dextran backbone is 2:1:1:1.

Another embodiment of the present invention relates to the aAPC scaffold as described herein, wherein the ratio between dextran backbone, pMHC, IL-1, B7.2 (CD86) and PD-L1 is 1:10:5:5:5.

Yet another embodiment of the present invention relates to the aAPC scaffold as described herein, wherein
i. the polymeric backbone is dextran,
ii. the co-stimulatory molecules are B7.2 (CD86) and ICOS, and
iii. the cytokine is IL-10.

Still another embodiment of the present invention relates to the aAPC scaffold as described herein, wherein
i. the polymeric backbone is dextran, and
ii. the cytokines are IL-1 and IL-2.

A further embodiment of the present invention relates to the aAPC scaffold as described herein, wherein
i. the polymeric backbone is dextran, and
ii. the cytokines are IL-2 and IL-15.

A further embodiment of the present invention relates to an artificial antigen presenting cell (aAPC) scaffold comprising a polymeric backbone to which are attached the following template molecules:
i. at least one major histocompatibility complex molecule comprising an antigenic peptide (pMHC), and
ii. B7.2 (CD86), ICOS and PD-L1.

The aAPC scaffolds of the present invention may be part of a kit suitable for use by hospitals and laboratories. Such a kit may comprise one or more different aAPC scaffolds suitable for expanding T cells with different specificities, as well as medium suitable for expanding T cells extracted from a sample. The kit may also hold other compounds or molecules necessary for the expansion of a T cell-containing sample.

The aAPC scaffolds of the present invention may be used as an immunotherapy for direct administration into a subject to aid the immune system of the subject. The aAPC may be administered either locally or systemically via any route, such as intravenous, intraperitoneal, intramuscular, subcutaneous, transdermal or oral.

Method of T-Cell Expansion

By extracting immune-reactive T cells from a unhealthy subject, expanding the T cells ex vivo and re-introducing the expanded T cell population into the subject, it is possible to overcome some of the challenges of immune suppressive diseases that otherwise render the immune system paralysed. However, although the extraction of T cells from e.g. peripheral blood by apheresis procedures and subsequent re-introduction into the patient is unproblematic, the activation and expansion of T cells of a given specificity remains a great challenge with the resulting T cell population often lacking sufficient differentiation and functional capacity.

The aAPC scaffold of the present invention is suitable for simultaneous in vitro stimulation and expansion of T cells and yields T cell populations with a high ratio of active T cells, high antigen specificity of the T cells and high functionality of the T cells. Thus, a second aspect of the present invention relates to a method for simultaneous in vitro stimulation and expansion of T cells, comprising the following steps:
i. providing a sample comprising T cells,
ii. contacting said sample with a solution comprising an aAPC scaffold as described herein,
iii. stimulating and expanding T cells with specificity for said aAPC scaffold in culture, and
iv. harvesting the T cells of step iii) from the culture to obtain an expanded antigen-specific population of T cells.

The sample comprising the T cells is extracted from a subject and subsequently put into a culture comprising the aAPC scaffold under conditions that allow growth of the T cells. Thus, it is to be understood that the expansion of the T cells is to be carried out in a solution or medium that in addition to the aAPC scaffold contains all the necessary compounds and factors for cell proliferation. Thus, the culture in which the T cell expansion is carried out may contain compounds that inhibit growth of irrelevant cells or promote growth of the T cells, e.g. IL-2.

To enhance the quality of the expanded T cell population, the aAPC scaffold may be filtered by centrifugation through a molecular weight cut-off filter in order to remove all non-bound pMHC molecules prior to mixing of the aAPC with the sample. This is to avoid stimulation from pMHC molecules not conjugated to scaffolds, and to remove excess peptide, cytokines, and co-stimulatory molecules to limit the stimulation of irrelevant T cell subsets. The same applies to antigens not complexed to MHC molecules, which can also be removed by centrifugation through a molecular weight cut-off filter.

Thus, an embodiment of the present invention relates to the method as described herein, wherein the solution comprising an aAPC scaffold of step ii) has been filtered before contact with the sample.

Another embodiment of the present invention relates to the method as described herein, wherein the solution comprising an aAPC scaffold is filtered by centrifugation through molecular weight cut-off filters.

An advantage of the aAPC scaffolds of the present invention is that they allow simultaneous expansion of different T cell specificities because the cross-reactivity when using multiple different aAPC scaffolds is reduced to a minimum as explained above. The method of the present invention is therefore also effective for samples containing a variety of T cells with different specificities.

Therefore, an embodiment of the present invention relates to the method as described herein, wherein said sample of step i) comprises T-cells of at least 2 different specificities, such as at least 5 different specificities, such as at least 10 different specificities, such as at least 15 different specificities, such as at least 20 different specificities, or such as at least 50 different specificities.

Another embodiment of the present invention relates to the method as described herein, wherein said solution comprising an aAPC scaffold comprises at least 2 different aAPC scaffolds, such as at least 5 different aAPC scaffolds, such as at least 10 different aAPC scaffolds, such as at least 15 different aAPC scaffolds, such as at least 20 different aAPC scaffolds, or such as at least 20 different aAPC scaffolds.

Yet another embodiment of the present invention relates to the method as described herein, wherein T-cells of at least 2 different specificities are stimulated and expanded in parallel in the same sample, such as at least 5 different specificities, such as at least 10 different specificities, such as at least 15 different specificities, or such as at least 20 different specificities.

A further embodiment of the present invention relates to the method as described herein, wherein the method comprises the following steps:
i. providing a sample comprising T cells with at least 5 different specificities, ii. contacting said sample with a solution comprising at least 5 different aAPC scaffolds,
iii. parallel stimulation and expansion of said T cells with at least 5 different specificities for said at least 5 different aAPC scaffolds in culture, and
iv. harvesting the T cells of step iii) from the culture to obtain an expanded antigen-specific population of T cells with at least 5 different specificities.

The sample comprising the T cells to be expanded may originate from any source, but is typically extracted from blood, a tissue or a body fluid. Thus, an embodiment of the present invention relates to the method as described herein, wherein the sample is selected from the group consisting of peripheral blood mononuclear cells, tumors, tissue, bone marrow, biopsies, serum, blood, plasma, saliva, lymph fluid, pleura fluid, cerospinal fluid and synovial fluid.

The sample comprising the T cells to be expanded according to the method described herein may also be selected from stem cells, TCR modified/transfected cells, chimeric antigen receptor (CAR) T cells.

Thus, an embodiment of the present invention relates to the method as described herein, wherein the sample comprises CAR T cells and the at least one antigen is not presented by a MHC molecule.

Thus, an embodiment of the present invention relates to the method as described herein, wherein the sample comprises CAR T cells and the at least one antigen of the aAPC scaffold is a CD protein.

Another embodiment of the present invention relates to the method as described herein, wherein the sample comprises CAR T cells and the at least one antigen is selected from the group consisting of CD19, CD20 and CD22.

The method of the present invention may be used to expand any T cell expressing the TCR necessary for interaction with the pMHC molecule on the aAPC scaffold. The T cells suitable for expansion by the method of the present invention therefore include, but are not limited to, CD8 T cells, CD4 T cells, regulatory T cells, natural killer T (NKT) cells, alpha-beta T cells, gamma-delta T cells, innate mucosal-associated invariant T (MAIT) cells, and lymphokine-activated killer (LAK) cells.

Thus, an embodiment of the present invention relates to the method as described herein, wherein the T cells are selected from the group consisting of CD8 T cells, CD4 T cells, regulatory T cells, natural killer T (NKT) cells, gamma-delta T cells and innate mucosal-associated invariant T (MAIT) cells.

Another embodiment of the present invention relates to the method as described herein, wherein the T cells are selected from the group consisting of CAR T cells, CD8 T cells, CD4 T cells, regulatory T cells, natural killer T (NKT) cells, gamma-delta T cells and innate mucosal-associated invariant T (MAIT) cells A preferred embodiment of the present invention relates to the method as described herein, wherein the T cells are CD8 T cells.

Yet another embodiment of the present invention relates to the method as described herein, wherein the T cells are CAR T cells For the re-introduction of an expanded T cell population into a patient to be meaningful from a therapeutic perspective, it is necessary that the extracted T cells are expanded to a clinically relevant number. Expansion of T cells by the method of the present invention is on the order of 100-3000 fold. The number of cells available before re-introduction into a patient is feasible is in the range of $10^9$-$10^9$ cells per administration. Cells are administered in a volume of 20 mL to 1 L depending on the route of administration.

Therefore, an embodiment of the present invention relates to the method as described herein, wherein the T cells are expanded to a clinically relevant number.

As described above for the aAPC scaffold, the pMHC molecules may present a variety of antigenic peptides. The same considerations regarding the choice of antigenic peptides apply for the method. Thus, an embodiment of the present invention relates to the method as described herein, wherein the antigenic peptide of the pMHC is a cancer-associated epitope or virus epitope.

Another embodiment of the present invention relates to the method as described herein, wherein the antigen comprises a cancer-associated epitope or virus epitope.

Another embodiment of the present invention relates to the method as described herein, wherein the cancer-associated epitope is a virus epitope associated with a virus-induced cancer.

Yet another embodiment of the present invention relates the method as described, wherein the virus epitope is from a virus selected from the group consisting of human papillomavirus (HPV), Merkel cell polyomavirus (MCV), cytomegalovirus (CMV), Epstein-Barr virus (EBV), human T-lymphotropic virus (HTLV), hepatitis B virus (HBV), hepatitis C virus (HCV) and influenza virus.

Use of the Expanded T-Cell Population

It is envisioned that the expanded T cell population obtained by the method of the present invention can be used effectively in a treatment regimen focusing on adoptive immunotherapy (or adoptive cell transfer). In such a treatment regimen, immune-reactive T cells from a subject in need of treatment are extracted. The subject may be any mammal, such as humans, cows, pigs, birds, dogs, cats, mice, rats and the like. The source of the T cells may for example be peripheral blood mononuclear cells, tumors, tissue, bone marrow, biopsies, serum, blood, plasma, saliva, lymph fluid, pleura fluid, cerospinal fluid or synovial fluid.

Once extracted from the subject, the sample containing the T cells of the desired specificity or specificities is expanded using an aAPC scaffold customized to the subject and the condition or the disease to be treated. This expansion is conducted in accordance with the method of the present invention as described above. When the T cell population has been expanded to a clinically relevant number, it is administered to the subject to induce an immune response and treat the disease.

Consequently, a third aspect of the present invention relates to an expanded T cell population obtained by the method as described herein.

A fourth aspect of the present invention relates to an expanded T-cell population obtained by the method as described herein for use as a medicament.

More specifically, an embodiment of the of the present invention relates to a method for adoptive immunotherapy of a disease or disorder comprising
i. extracting a sample comprising T cells from a subject,
ii. contacting said sample with a solution comprising an aAPC scaffold as described herein,
iii. stimulating and expanding T cells with specificity for said aAPC scaffold in culture,
iv. harvesting the T cells of step iii) from the culture to obtain an expanded antigen-specific population of T cells, and
v. administering the expanded antigen-specific population of T cells to the subject in an amount effective to induce an immune response.

As described above for the aAPC scaffold, the pMHC molecules may present a variety of antigenic peptides. The same considerations regarding the choice of antigenic peptides apply for the use of the expanded T-cell population obtained by the method of the present invention.

Thus, a fifth aspect of the present invention relates to an expanded T-cell population obtained by the method as described herein for use in the treatment of a cancer or viral condition.

An embodiment of the present invention relates to the expanded T-cell population for use as described herein, wherein the cancer is associated with a viral condition.

Another embodiment of the present invention relates to the expanded T-cell population for use as described herein, wherein the viral condition is associated with a virus selected from the group consisting of human papillomavirus (HPV), Merkel cell polyomavirus (MCV), cytomegalovirus (CMV), Epstein-Barr virus (EBV), human T-lymphotropic virus (HTLV), hepatitis B virus (HBV), hepatitis C virus (HCV) and influenza virus.

The expanded T cell population obtained by the method as described herein may be formulated in a pharmaceutical composition further comprising one or more adjuvants and/or excipients and/or a pharmaceutically acceptable carriers. The excipients may include, but are not limited to, buffers, suspending agents, dispersing agents, solubilising agents, pH-adjusting agents and/or preserving agents.

The pharmaceutical composition may be used in adoptive immunotherapy (or adoptive cell transfer) for administration either locally or systemically via any route, such as intravenous, intraperitoneal, intramuscular, subcutaneous, transdermal or oral.

It should be noted that embodiments and features described in the context of one of the aspects of the present invention also apply to the other aspects of the invention.

All patent and non-patent references cited in the present application, are hereby incorporated by reference in their entirety.

The invention will now be described in further details in the following non-limiting examples.

EXAMPLES

Example 1: Assembly of Artificial Antigen Presenting (aAPC) Scaffolds and Specific T Cell Expansion Using the aAPC (FIG. 1)

Here is described how aAPC scaffolds can be made by coupling pMHC complexes, cytokines and stimulatory molecules to dextran via a streptavidin-biotin interaction. In principle, biotin-streptavidin can be replaced by any dimerization domain, where one half of the dimerization domain is coupled to the pMHC complex, cytokine or co-stimulatory molecule and the other half is coupled to dextran or similar scaffold backbone (see FIG. 1A).

Streptavidin modified dextran is commercially available in various sizes of dextran such as MW 250 KDa, 750 KDa, 2000 KDa from Fina Biosolutions and from Immudex with dextran of approximately 270 KDa. The pMHC monomers can be produced by classical *E. coli* expression methods or it can be bought commercially from suppliers such as BioLegend. pMHC, cytokines and co-stimulatory molecules can be biotinylated by both standard chemical and enzymatic protocols. For example, pMHC can be enzymatically biotinylated by including a biotinylation consensus peptide sequence in the MHC heavy chain allowing site-specific biotinylation using BirA enzyme and free biotin. Cytokines and co-stimulatory molecules are commercially available from suppliers such as BioLegend and PreProtech. These proteins are readily biotinylated by using commercially available biotinylation reagents such as EZ-Link Sulfo-NHS-LC-Biotin from ThermoFisher Scientific and reacting according to supplier's protocol.

All the above given components were assembled to aAPC scaffolds via the streptavidin-biotin interaction. Briefly, molecules were combined in aqueous buffer, such as PBS, in relative stoichiometry according to the examples described below to give a final concentration of 60 nM assembled aAPC scaffold. The aAPC scaffold was allowed to assemble at 4° C. for one hour and was thereafter kept at 4° C. until addition to the cell culture. Assembled scaffolds can be stored at 4° C. for at least one month. Assembled aAPC scaffold can be purified and separated from unbound peptide, pMHC, cytokines and co-stimulatory molecules by centrifuging unbound molecules through a MW cut-off filter such as an Amicon Ultra centrifugal filter units Ultra-4, MWCO 100 kDa.

The T cell cultures were established from human PBMCs or TILs and initiated with $2 \times 10^6$ cells/ml in a 48 well flat bottom culture plates and cultured for 2 weeks at 37° C. and 5% $CO_2$. The cells were stimulated twice a week by adding 0.2 nM final aAPC scaffold in 1 mL fresh X-VIVO 15 media supplemented with 5% heat inactivated human serum and 20 IU/ml recombinant human IL-2. After 1 week of culturing, the cells were transferred to a 24 well flat bottom culture plates, and once a week a sample was taken from the cultures for MHC tetramer staining to track the expansion of antigen-specific CD8 T cells by flow cytometry.

Assembled aAPC may be utilized to expand specific T cell populations extracted from patients (see FIG. 1B). The T cells may for instance be CD8 T cells, CD4 T cells, regulatory T cells or natural killer T (NKT) cells that can be expanded to a clinically relevant number and reintroduced into the patient for treatment of disease. The use of aAPC scaffolds for expansion of T cells ensures a high ratio of active T cells, high antigen specificity of the T cells and high functionality of the T cells. By using several different aAPC scaffolds in a single sample, it is possible to simultaneously expand different antigen-specific T cells without competition between specificities, thereby retaining T cell specificity and a pool of different specificities ensuring a broad immune response.

Example 2: Determination of Scaffold to Molecule Ratio (FIGS. 2 and 3)

It is important that the interaction between the antigen presenting scaffold, referred to as MHC-scaffold in figure legends, and T cell receptors (TCRs) is directed by the pMHC molecules, and not by the cytokines or co-stimulatory molecules, since all T cells have receptors for binding these molecules. It is therefore fundamental to have an optimal number and density of pMHC molecules attached to the antigen presenting scaffold to ensure that the interaction is governed by the specific interaction between pMHC and TCR. To determine the most optimal composition of the antigen presenting scaffolds and the number of pMHC molecules required for a TCR-pMHC driven interaction, different ratios of pMHC, cytokines, and co-stimulatory molecules were conjugated to scaffold backbones and applied in staining of healthy donor peripheral blood mononuclear cells (PBMCs) and analysed by flow cytometry.

Antigen presenting scaffolds carrying virus peptide HLA-A1 CMV pp65 YSE were assembled in different scaffold:

pMHC ratios and co-attached with co-stimulation, and were applied in staining of PBMCs of one healthy donor with response against the CMV pp65 YSE peptide. The mean fluorescence intensity (MFI) of each staining was used to determine the optimal number of pMHC to be conjugated to the scaffolds, and staining index (SI) was used as a measure of separation between positive and negative events. MFI and SI values of antigen-specific CD8 T cells detected for each staining are shown in FIG. 2.

Conclusion:

(FIG. 2A) The ratios 1:10 and 1:20 (scaffold:pMHC) were found to be optimal as these show the highest MFI values, but TCR-pMHC interactions are retained even at 1:5 ratio. (FIGS. 2B-C) From these stainings it could be concluded that the antigen presenting scaffold compositions 1:10:5:5 and 1:20:5:5 (scaffold:pMHC:B7-2:IL-15) were optimal, since these show the highest MFI and SI values compared to ratio of 1:10:10:10.

Antigen presenting scaffold ratios of 1:15:5:5 (scaffold:pMHC:B7-2:IL-15), 1:10:5:5:5 (scaffold:pMHC:B7-2:IL-15:IL-21) and 1:8:8:8 (scaffold:pMHC:IL-2:IL-21) were used in further expansion experiments of virus-specific CD8 T cells from healthy donor PBMCs.

Two control stainings were conducted with scaffolds not carrying any pMHC molecules, but with either B7-2 or IL-15 in ratios of 1:30 (scaffold:B7-2) and (scaffold:IL-15) respectively. This was carried out to investigate the level of B7-2 and/or IL-15 mediated binding of the antigen presenting scaffolds to T cells. Representative dot plots are shown for the two control stainings in FIG. 3.

Conclusion:

(FIGS. 3A-B) Based on the two control stainings, the interaction between scaffolds and unspecific T cells populations is very limited, as no significant binding was observed for any of the two scaffolds.

Example 3: Expansion of Antigen-Specific CD8 T Cells Using Antigen Presenting Scaffold (FIG. 4)

HLA-A1 FLU BP-VSD specific CD8 T cells from a healthy donor were expanded in parallel in the presence of either antigen presenting scaffold with the ratio 1:10:5:5:5 (scaffold:pMHC:B7-2:IL-15:IL-21), free FLU BP-VSD peptide, IL-15, and IL-21 cytokines, or antigen presenting scaffold with the ratio 1:10:5:5:5 carrying an irrelevant peptide specificity in the MHC complex. All cultures were supplemented with 20 IU/ML IL-2 and cultured for 2 weeks. The expansion of the HLA-A1 FLU BP-VSD specific CD8 T cells were traced by tetramer staining once a week. Representative dot plots are shown in FIG. 4.

Conclusion:

(FIGS. 4A-D) This experiment demonstrates that it is feasible to expand antigen-specific CD8 T cells with low frequent baseline responses in a pMHC directed manner, using antigen presenting scaffolds. When comparing of expansion of cells stimulated with peptide, IL-15 and IL-21 added freely in the culture media, and cells stimulated with antigen presenting scaffolds, it is clear that cells stimulated with antigen presenting scaffolds have expanded the most both in frequency and in absolute number of specific CD8 T cell (see FIGS. 4E-F). Furthermore, antigen presenting scaffolds carrying irrelevant peptide MHC specificity were not able to stimulate A1 FLU BP-VSD specific CD8 T cell expansion, demonstrating that the cells cannot benefit from the co-attached cytokines and co-stimulatory molecules, without established pMHC directed interaction.

Figure 7A:
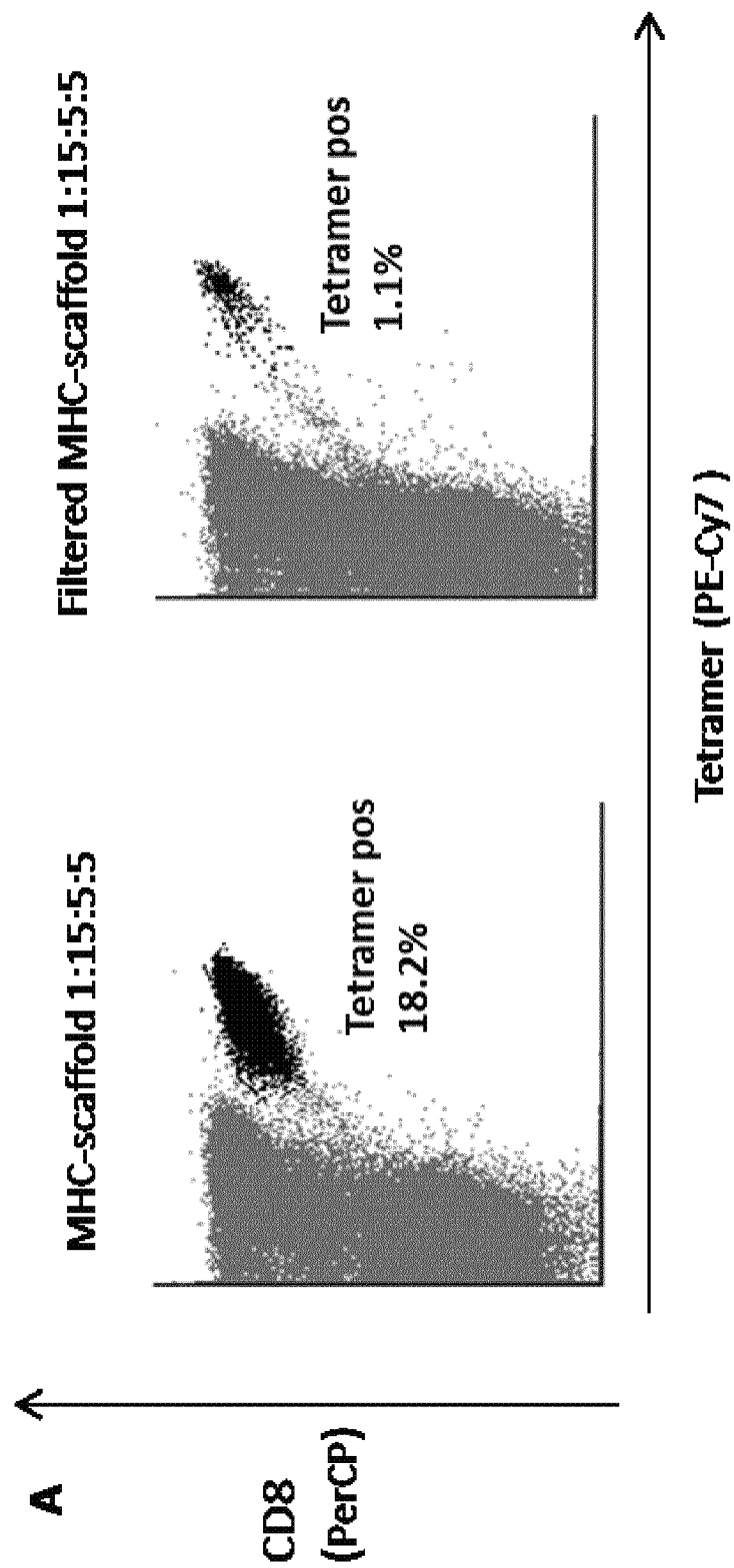
FIG. 7 shows (A) Frequency of HLA-A1 FLU BP-VSD specific CD8 T cells from a healthy donor detected by tetramer staining after 2 weeks stimulation either with unfiltered or filtered antigen presenting scaffold with the ratio 1:15:5:5 (scaffold:pMHC:B7-2:IL-15). CD8 antibody is PerCP labeled (Y-axis) and the tetramer is PE-Cy7 labeled (X-axis). (B) Dot plots showing frequency of CD45RA and CD28 expression, (C) CD45RA and CCR7 expression, and (D) CD45RA and CD57 expression of HLA-A1 FLU BP-VSD specific CD8 T cells after 2 weeks expansion with either unfiltered or filtered antigen presenting scaffold with the ratio 1:15:5:5.

Example 4: Filtering of Antigen Presenting Scaffolds Prior to Expansion of Antigen-Specific CD8 T Cells (FIGS. 5-7)

After assembly of the antigen presenting scaffolds, these were filtered using centrifugation through a molecular weight cut-off filter in order to remove all non-bound pMHC molecules to avoid stimulation from pMHC not conjugated to scaffolds, and to remove excess peptide, cytokines, and co-stimulatory molecules to limit the stimulation of irrelevant T cell subsets. A number of experiments were carried out in parallel, in order to investigate and compare the effect of filtering the antigen presenting scaffolds vs. not filtering the antigen presenting scaffolds prior to use in stimulation of antigen-specific CD8 T cells. Expansion levels of various differentiation markers were investigated for the expanded CD8 T cells in order to determine their phenotype. In these experiments antigen presenting scaffolds with the ratio 1:15:5:5 (scaffold:pMHC:B7-2:IL-15) were used. See FIGS. 5-7.

Conclusion:

(FIGS. 5 A-D) Cells stimulated with the filtered antigen presenting scaffolds show highest MFI, compared to cells stimulated with the unfiltered antigen presenting scaffold and free peptide, indicating that the filtered antigen presenting scaffold preferentially stimulates T cells with high affinity TCRs or initiates an up-regulation of TCR expression on the population of T cells expanded. However, the expansion rate of filtered MHC scaffolds was slightly compromised compared to unfiltered MHC scaffolds. The use of filtered reagents provides optimal functional characteristics (as shown later). Using both filtered and unfiltered scaffolds provides better T expansion and superior functional characteristics compared to stimulation with free peptide-cytokines.

(FIGS. 6A-B) The highest expression of CD28 was detected for the high affinity binding population (black population) stimulated with the filtered antigen presenting scaffolds compared to stimulation with the unfiltered antigen presenting scaffold (dark grey population).

(FIGS. 7A-D) Cells stimulated with filtered antigen presenting scaffold clearly obtain a higher CD28 expression compared to cells stimulated with unfiltered antigen presenting scaffold, meaning that filtration of antigen presenting scaffolds prior to T cell stimulation cultures can provide a more robust phenotype for adoptive transfer purposes— with high level of CD28 expression being associated with enhanced survival and expansion in vivo. There was no significant difference in CCR7 and CD57 expression between filtered and unfiltered antigen presenting scaffolds.

Example 5: Expression of Differentiation and Co-Inhibitory Markers on Antigen-Specific CD8 T Cells Expanded with Antigen Presenting Scaffolds (FIGS. 8 and 9)

T cells are characterized by different surface molecules that determine their differential and functional status. The differentiation status can be defined by the T cell phenotype. T cells are dynamically evolving over time of a given antigen exposure, but may roughly be categorized into four different group. Naïve T cell, Effector T cell (TEM), late-stage effector T cells (TEMRA), and central memory T cells. The naïve pool is responsible for mounting a T cell response to previously unexperienced pathogens, whereas reinfection is often cleared by mounting a strong and fast T cell response among T CM or certain groups for TEM. These T cells are highly proliferative and very responsive to antigen stimulation. For adoptive transfer purposes, such a phenotype is preferable. Thus, we aim for high CD28 expression and low CD57 expression. Some level of CCR7 expression is preferable due to their homing capabilities.

Tim-3, LAG-3 and PD-1 are exhaustion/activation markers on T cells. These molecules function to regulate immune responses following T cell activation. They serve as a natural mechanism to avoid excessive T cell activation, but in the context of immune therapy, ideally these molecules should be minimally expressed on T cells to provide the optimal capacity for T cell function and expansion in vivo. PD-1 seems to be the most critical and dynamic marker among these. Blocking of PD-1 signaling has been shown to provide dramatic T cell activation, and consequently cancer rejection in patients.

The expression of differentiation and co-inhibitory markers of the expanded CD8 T cells was investigated for cultures expanded with filtered and unfiltered antigen presenting scaffold with ratio 1:10:5:5:5 (scaffold:pMHC:B7-2:IL-15:IL-21) and compared with cells expanded with free peptide and cytokines. Likewise, cultures expanded with filtered and unfiltered antigen presenting scaffold with ratio 1:8:8:8 (scaffold:pMHC:IL-2:IL-21) was compared with antigen presenting scaffold 1:8 (scaffold:pMHC) plus free cytokines in the culture media. See FIGS. 8-9.

Conclusion:

(FIGS. 8A-D) These stainings show that the A1 FLU BP-VSD specific CD8 T cells, stimulated with the filtered antigen presenting scaffolds with ratio 1:10:5:5:5 and 1:8:8:8 generated cells with higher CD28 expression, compared to all other stimulations. No particular difference in CCR7 and CD57 expression was observed for cells stimulated with the two different antigen presenting scaffold including the ratios 1:10:5:5:5 and 1:8:8:8.

(FIGS. 9A-D) These stainings show that cells stimulated with filtered and unfiltered antigen presenting scaffolds with composition 1:10:5:5:5 and 1:8:8:8:8 had the lowest positive expression of PD-1, compared to cells stimulated with free peptide and cytokines, and 1:8 antigen presenting scaffold and free cytokines. No particular difference in Tim-3 or LAG-3 expression was observed for any of the stimulations. Furthermore, the filtered antigen presenting scaffolds were able to stimulate the highest frequency of PD-1 negative A1 FLU BP-VSD specific CD8 T cells, compared to cells stimulated with unfiltered antigen presenting scaffolds or free peptide and cytokines.

Figure 10A:
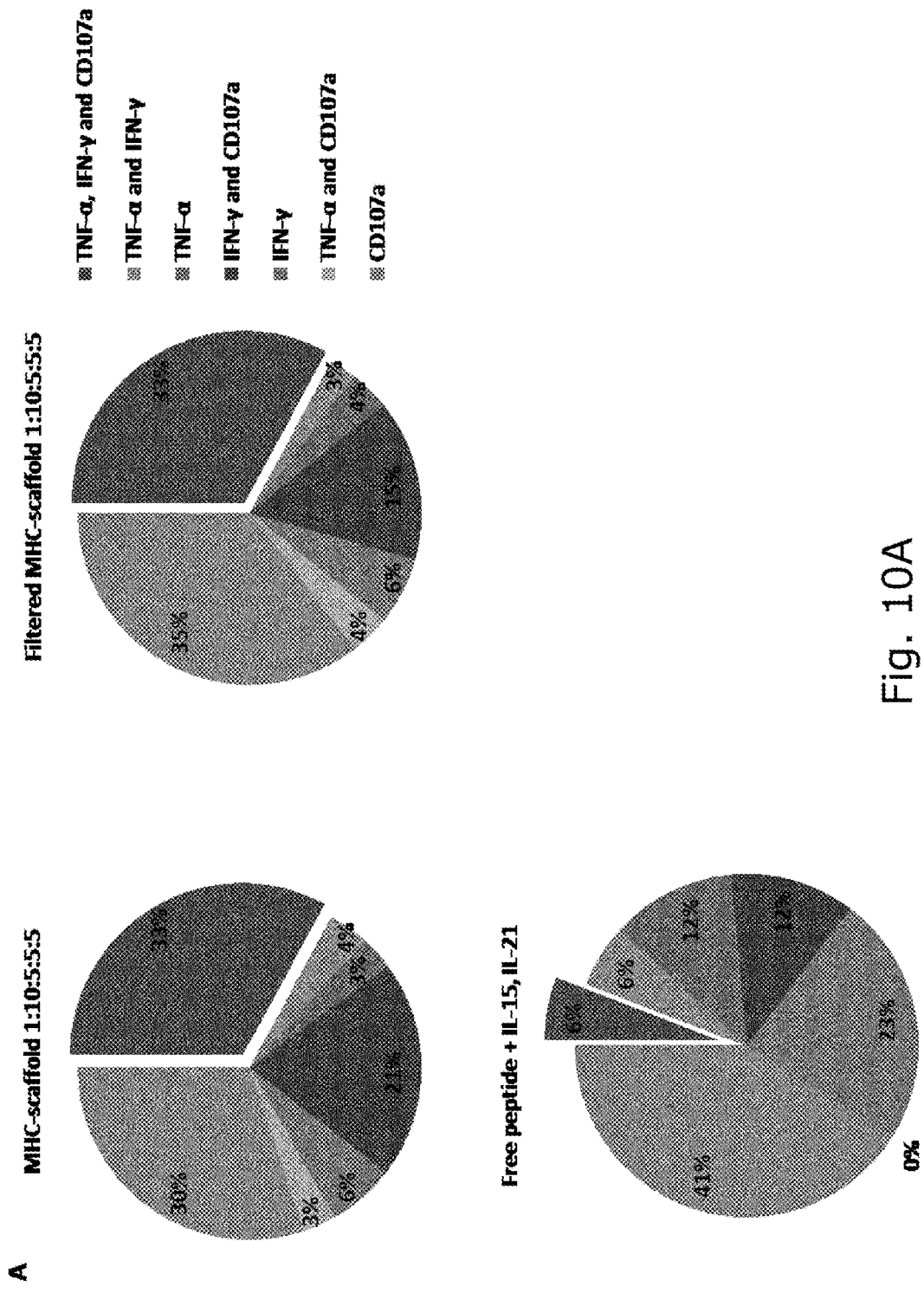
FIG. 10 shows frequency of TNF-α, IFN-γ and CD107a expression after in vitro peptide stimulation using HLA-A1 FLU BP-VSD peptide. Cytokine secretion in peptide responsive CD8 T cells was measured by intracellular cytokine staining. The tested cell cultures were obtained after 2 weeks expansion with either (A) filtered and unfiltered antigen presenting scaffolds of ratio 1:10:5:5:5 (scaffold:pMHC:B7-2:IL-15:IL-21) compared with free peptide and IL-15, IL-21 stimulation, or (B) filtered and unfiltered antigen presenting scaffolds of ratio 1:8:8:8 (scaffold:pMHC:IL-2:IL-21) with no IL-2 in the culture media, compared with antigen presenting scaffold 1:8 (scaffold:pMHC) with free IL-2 and IL-21. The diagrams show the frequency of triple, double and single positive HLA-A1 FLU BP-VSD specific CD8 T cells. The triple positive fraction is highlighted (through elevation) in each diagram.
Figure 10B:
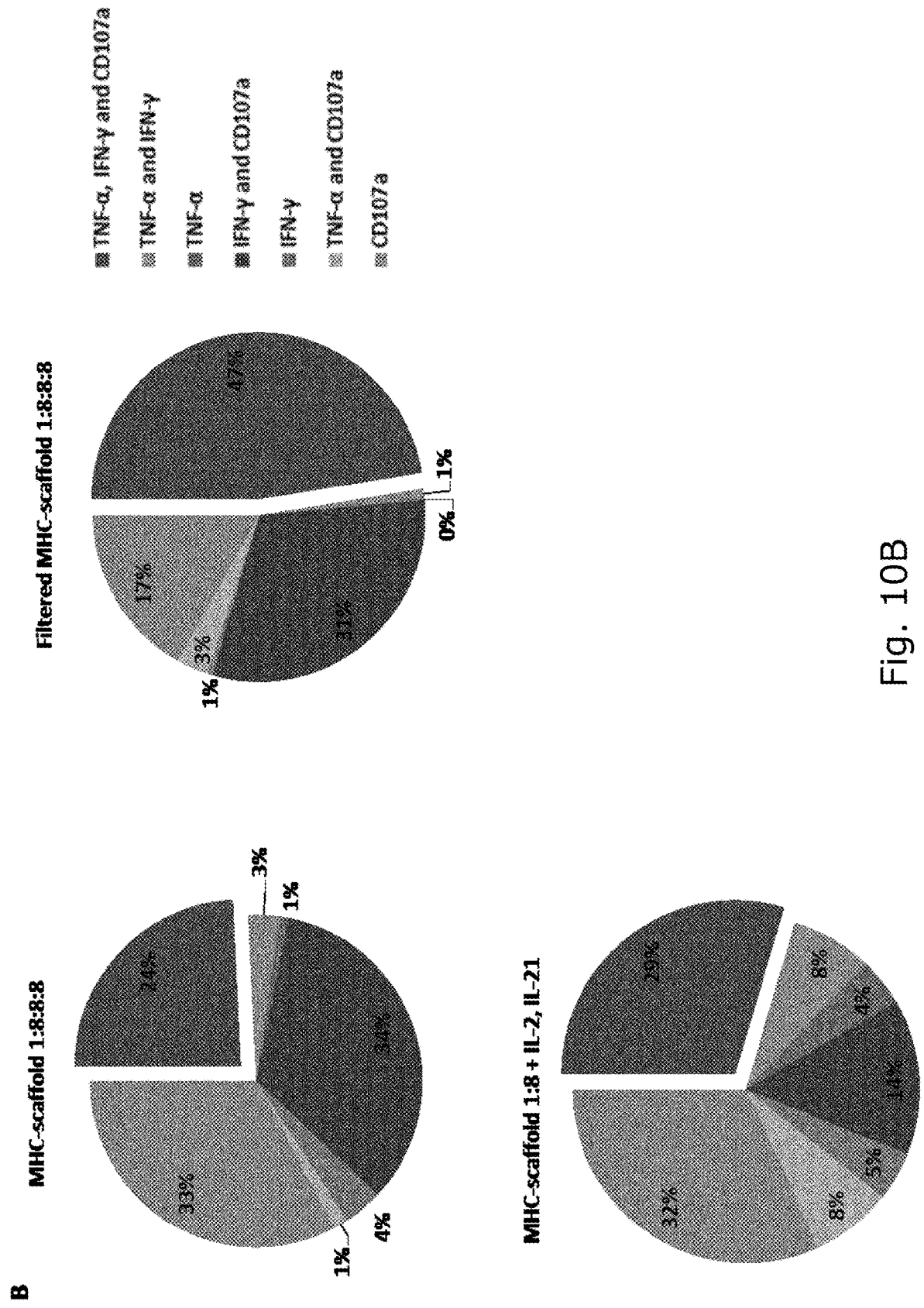

Example 6: Functionality of Expanded Antigen-Specific CD8 T Cells (FIG. 10)

In order to characterize the functional capacity of expanded antigen-specific CD8 T cells after antigen presenting scaffold stimulation, cells were challenged with antigen, and stained with intracellular cytokine antibodies to detect the production of TNF-α, and IFN-γ, and surface expression of degranulation marker CD107a. The expression of CD107a is associated with cytotoxic activity and ability to induce apoptosis in target cells. The production of TNF-α and IFN-γ in response to antigen recognition is important for indirect cytotoxic killing. CD8 T cells that express all three markers simultaneously are interpreted as having high killing capacity.

The functionality results shown in FIG. 10 represent T cell cultures expanded with filtered and unfiltered antigen presenting scaffold with ratio 1:10:5:5:5 (scaffold:pMHC:B7-2:IL-15:IL-21) and compared with cells expanded with free peptide and cytokines. Likewise, cultures expanded with filtered and unfiltered antigen presenting scaffold with ratio 1:8:8:8 (scaffold:pMHC:IL-2:IL-21) were compared with cells expanded with antigen presenting scaffold 1:8 (scaffold:pMHC) plus free cytokines in the culture media. Furthermore, it was investigated whether IL-2 as a supplement in the culture media was essential to stimulate CD8 T cells for expansion, or whether it could be excluded from the media, and attached onto the scaffold, in a ratio 1:8:8:8.

Conclusion:

(FIG. 10A) The frequency of triple positive CD8 T cells was higher for cultures stimulated with either filtered or unfiltered antigen presenting scaffolds when compared to cells stimulated with free peptide and cytokines. This implies that the scaffold-based interaction is required to provide efficient T cells stimulation and activation of multifunctional T cells.

(FIG. 10B) These results showed that it was possible to exclude IL-2 from the culture media and instead attached it onto the antigen presenting scaffold, and still obtain multifunctional CD8 T cells (triple positive). Moreover, cells stimulated with filtered antigen presenting scaffolds obtain the highest frequency of multifunctional (triple positive) CD8 T cells, when compared to cells stimulated with unfiltered antigen presenting scaffolds.

Example 7: pMHC Directed Stimulation (FIG. 11)

It was investigated whether the antigen presenting scaffolds direct their stimulatory signals in a pMHC dependent manner or whether antigen-specific CD8 T cells could also benefit from stimulation solely based on interaction with the co-attached cytokines and co-stimulatory molecules on the antigen presenting scaffold, without relevant peptide specificity in the MHC molecules. To investigate this HLA-A1 FLU BP-VSD specific CD8 T cells from a healthy donor were stimulated for 2 weeks with either antigen presenting scaffolds with the 1:10:5:5:5 (scaffold:pMHC:B7-2:IL-15:IL-21) carrying HLA-A3 LTA ASF in the MHC complex as an irrelevant peptide specificity, or HLA-A1 FLU BP-VSD as a relevant peptide specificity. The CD8 T cells were then compared in their ability to express CD107a and produce TNF-α and IFN-γ, upon challenge with HLA-A1 FLU BP-VSD peptide. The experiment was carried out in duplicate. Representative dot plots are shown in FIG. 11.

Conclusion:

(FIGS. 11A-B) From these analyses it was evident that antigen presenting scaffold stimulation is exclusively directed by the specificity of the pMHC molecules attached, and cells cannot benefit from stimulation of the co-attached cytokines and co-stimulatory molecules without specific recognition and interaction with pMHC molecules.

Figure 12:
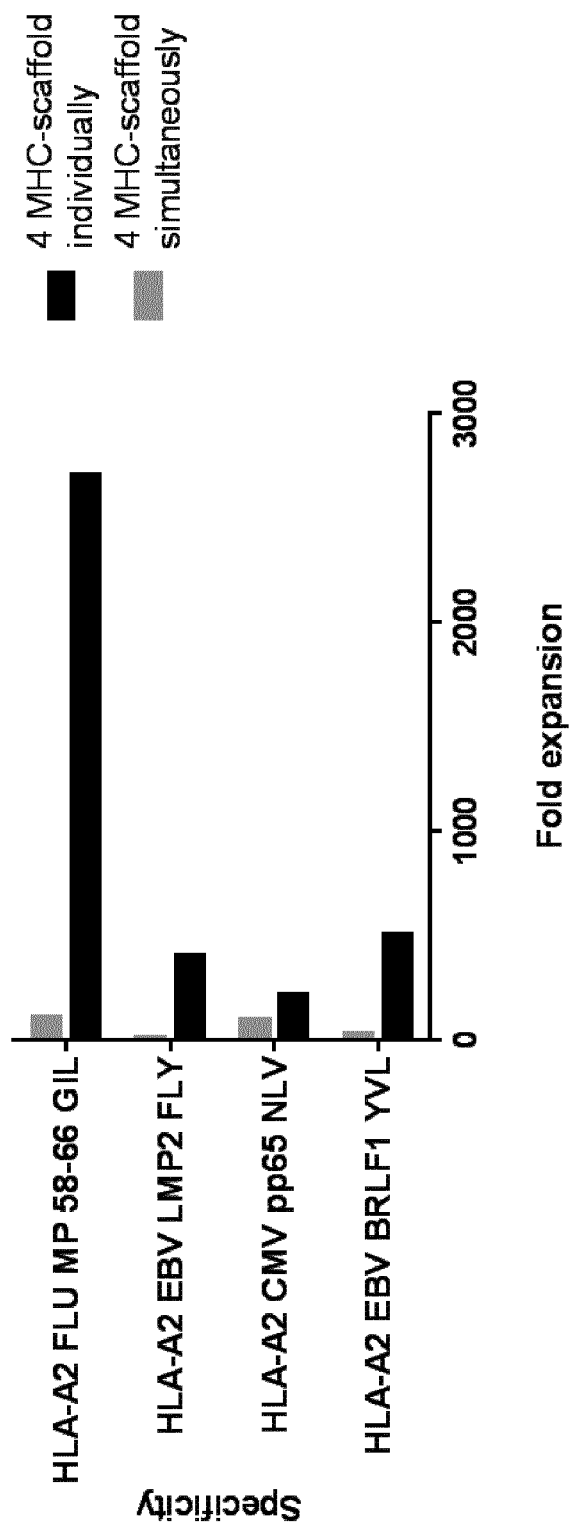
FIG. 12 shows fold expansion of 4 virus responses from a healthy donor after 2 weeks expansion with antigen presenting scaffolds with the ratio 1:10:5:5:5 (scaffold:pMHC:B7-2:IL-15:IL-21). Five cultures were established.

Example 8: Use of Antigen Presenting Scaffolds to Expand Multiple Antigen-Specific CD8 T Cells Simultaneously (FIG. 12)

The antigen presenting scaffold system holds a potential advantage in stimulation of multiple CD8 T cell specificities simultaneously without occurrence of peptide-competition. Broad T cell responses are preferable for clinical applications to avoid immune escape by loss-of-target mechanisms. However, using traditional peptide-based stimulation strategies, competition among the peptides will occur for binding to MHC class I molecules to be presented to T cells.

Presentation advantages are given to peptides with the highest binding affinity and stability. It is consequently challenging to stimulate multiple T cell responses equally well with free peptides. When using antigen presenting scaffolds to stimulate multiple CD8 T cell specificities simultaneously, peptide competition is avoided as the peptides are already inserted into MHC molecules and assembled onto scaffolds.

To demonstrate this property of the antigen presenting scaffolds, an experiment was conducted where PMBCs from a healthy donor with 4 virus responses (HLA-A2 EBV BRLF1 YVL, HLA-A2 CMV pp65 NLV, HLA-A2 EBV LMP2 FLY, and HLA-A2 FLU MP 58-66 GIL) were used to investigate how many different specificities could potentially be stimulated simultaneously in the same culture using antigen presenting scaffolds.

Five cultures were established from this donor, where 4 cultures were used to expand the 4 responses individually, and one culture was used to expand all 4 responses simultaneously. Thus, 4 different antigen presenting scaffold were assembled, each carried 1 of the 4 virus specificities, and these were added individually to culture 1-4, thus one specificity was expanded per culture. Then, in culture 5 all 4 antigen presenting scaffolds were added simultaneously to expand 4 virus responses at the same time, in the same culture. Briefly, the cells were stimulated twice a week by adding for each specificity 0.2 nM final aAPC scaffold in 1 mL of fresh X-VIVO 15 media supplemented with 5% heat inactivated human serum and 20 IU/ml recombinant human IL-2. After 1 week of culturing, the cells were transferred to a 24 well flat bottom culture plate, and once a week a sample was taken from the cultures for MHC tetramer staining to track the expansion of antigen-specific CD8 T cells by flow cytometry. The number of pMHC specific T cells corresponding to the 4 virus responses was assessed by tetramer staining after 2 weeks expansion. The fold expansion was thereafter calculated for each specificity by dividing the absolute number of specific CD8 T cells, obtained after 2 weeks expansion, with the absolute number of specific CD8 T cells from baseline. The fold expansion results are shown in FIG. 12.

It is contemplated that both responses expanded individually using the aAPC scaffolds, and responses expanded simultaneously using the aAPC scaffolds are expanded more efficiently than the corresponding template molecules free in solution. Thus, the corresponding template molecules in solution infer competition between specificities (also irrelevant specificities) and consequently result in an expanded T cell population of lesser antigen specificity and functionality of the T cells than a T cell population expanded using the aAPC scaffolds. This scenario is especially relevant for simultaneous expansion of several specificities.

Conclusion:

(FIG. 12) From this experiment it is clear that the highest fold expansion of antigen-specific CD8 T cells is achieved when only one specificity is stimulated in one culture (black bars). When mixing different antigen presenting scaffolds to expand 4 specificities simultaneously, the fold expansion decreases. Nevertheless, it is demonstrated that the antigen presenting scaffolds are capable of expanding multiple specificities simultaneously. In clinical situations, starting material is often at a minimum, and it is an advantage to stimulate many different specificities in a single sample.

Example 9: The Combination of Stimulatory Molecules on the Antigen Presenting Scaffold Determines the Effect (FIGS. 13-15)

Here it is demonstrated that the combination of molecules, cytokines and co-stimulatory molecules, is important for the result of an antigen presenting scaffold-based T cell expansion. Specific combinations can be used to provide sufficient stimulation to T cells in order for the cells to gain high killing functionality and maintain a young phenotype, which are key features for T cells that are to be used in TIL based ACT, as it correlates with increased tumor regression.

Two experiments were carried out to investigate the functionality and expression of CD28 and PD-1 markers of antigen-specific CD8 T cells after stimulation with various antigen presenting scaffolds, carrying a combination of molecules that are known to provide differential immunological effects. These stimulations were compared with a reference antigen presenting scaffold, carrying a combination of molecules that was previously validated (see FIGS. 4-12), and known to provide positive stimulation to CD8 T cells.

Antigen presenting scaffolds with the ratio 1:10:5:5:5 and 1:8:8:8 were used in these experiments where HLA-A2 EBV LMP2 CLG specific CD8 T cells from a healthy donor were expanded for 2 weeks.

In the experiment using the antigen presenting scaffold with ratio 1:10:5:5:5 (scaffold:pMHC:B7-2:molecule 1:molecule 2), 21 different scaffolds were generated, all carrying the same pMHC molecule, and the B7-2 molecule in ratio 1:10:5 (scaffold:pMHC:B7-2), and additional attachment of different combinations of PD-L1, ICOS, OX40L, CD5, IL-1 IL-6, IL-10 in ratio 5:5 (molecule 1:molecule 2). The functionality of the HLA-A2 EBV LMP2 CLG specific CD8 T cells after expansion with these 21 different antigen presenting scaffolds is shown in FIG. 13. The reference scaffold with the ratio 1:10:5:5:5 (scaffold:pMHC:B7-2:IL-15:IL-21) is shown in duplicate.

Likewise, an alternative scaffold was assembled with ratio 1:8:8:8 (scaffold:pMHC:IL-2:molecule 1). 7 different antigen presenting scaffolds were assembled carrying the same pMHC specificity and IL-2 in ratio 1:8:8 (scaffold:pMHC:IL-2) and additional attachment of different combinations of PD-L1, ICOS, OX40L, CD5, IL-1 IL-6, IL-10 in ratio 8 (molecule 1). The number of specific T cells and the functionality of the HLA-A2 EBV LMP2 CLG specific CD8 T cells after expansion with each of the 7 different antigen presenting scaffold are shown in FIG. 14. The reference scaffold with the ratio 1:8:8:8 (scaffold:pMHC:IL-2:IL-21) is shown in duplicate.

Conclusion (FIGS. 13 and 14) These experiments demonstrate the relative potency of various molecules on the antigen presenting scaffolds to provide relevant stimulation to T cells in order for the cells to expand and develop favorable functional and phenotypical characteristics, characterized by low expression of PD1, high expression of CD28, and multi-functional cytokine response (TNF-α, IFN-γ and CD107a) upon antigen recognition. The expression of all three functional markers simultaneously (circle 3) is interpreted as multi-functionality, indicating that these cells have the highest killing capacity. Antigen presenting scaffolds with the combination scaffold:pMHC:B7-2:IL-1:PD-L1 and scaffold:pMHC:B7-2:IL-15:IL-21 (1:10:5:5:5) (see FIGS. 13A-B), and the scaffold with the combination scaffold:pMHC:IL-2:IL-1 and scaffold:pMHC:IL-2:IL-21(1:8:8:8) (see FIGS. 14A-B), yield the highest number of antigen-specific CD8 T cells with expression of all three markers simultaneously.

Conclusion:

(FIG. 15) from these analyses, the relative expression of CD28 and PD1 was determined. Antigen presenting scaffolds with the combination scaffold:pMHC:B7-2:IL-10:IL-6 and scaffold:pMHC:B7-2:IL-15:IL-21 (1:10:5:5:5) (see FIG. 15A), and scaffold with combination scaffold:pMHC:IL-2:ICOS and scaffold:pMHC:IL-2:IL-21 (1:8:8:8) (see FIG. 15B), yield the highest expression of CD28 among antigen-specific CD8 T cells. Furthermore, antigen presenting scaffold with the combination scaffold:pMHC:B7-2:ICOS:IL10 and scaffold:pMHC:B7-2:PD-L1:IL6 (1:10:5:5:5) (see FIG. 15A), and scaffold with combination scaffold:pMHC:IL-2:IL21 and scaffold:pMHC:IL-2:IL1 (1:8:8:8) (see FIG. 15B), yield the lowest expression of PD-1 among antigen-specific CD8 T cells. High expression of CD28 and low expression of PD1 are ideal features for cell populations for adoptive cell therapy.

The optimal scaffold for T cell stimulation should yield antigen specific T cells with high multifunctional properties, good expansion (high absolute number of specific cells), high expression of CD28 and low expression of PD1. The most promising scaffolds combining these features are: Combinations of pMHC with IL2, IL15, IL21, B7-2, ICOS, IL1.

Example 10: Different Length of Scaffold in Stimulation of Antigen-Specific CD8 T Cells (FIG. 16)

The use of various lengths of scaffolds as a backbone in antigen presenting scaffolds was investigated. Scaffolds of 250 kDa, 750 kDa, and 2000 kDa were used as a backbone in antigen presenting scaffolds of ratio 1:10:5:5:5 (scaffold:pMHC:B7-2:IL-15:IL-21), and applied in stimulation of HLA-A2 EBV LMP2 CLG specific CD8 T cells from a healthy donor for two weeks. The frequency of specific expansion was detected by tetramer staining in order to compare the expansion potential for the three scaffolds.

For all other experiments, a 250 kDa scaffold has been used. By employing a longer scaffold, more molecules can be attached, which may result in increased TCR-pMHC interaction and stimulation, and possibly an enhanced phenotypic and functional outcome of the T cells can be achieved. Alternatively, the molecules can be distributed better on a longer scaffold, because there was more space between the molecules, which may result in an improved stimulation of the T cells.

Conclusion:

(FIG. 16) From this experiment it is shown that all tested dextran lengths can be used as a scaffold in the antigen presenting scaffolds, as specific expansion of antigen specific T cells directed to the scaffold bearing pMHC moiety was obtained for all for them. The 750 kDA scaffold yield the highest frequency of specific CD8 T cells.

Example 11: Parallel Expansion of Multiple Antigen Specificities from One Donor Sample in on Culture (FIG. 17A-B)

Antigen specific CD8 T cells from a healthy donor, with five virus responses, were expanded in parallel essentially as described in example 1, except multiple T cell specificities were expanded in parallel and the frequency of antigen specific T cells from day 0 (baseline) and after 14 days expansion with aAPC scaffold 1:8:8:8 (scaffold:pMHC:IL-2:IL-21) was determined using MHC tetramers.

Figure 17A:
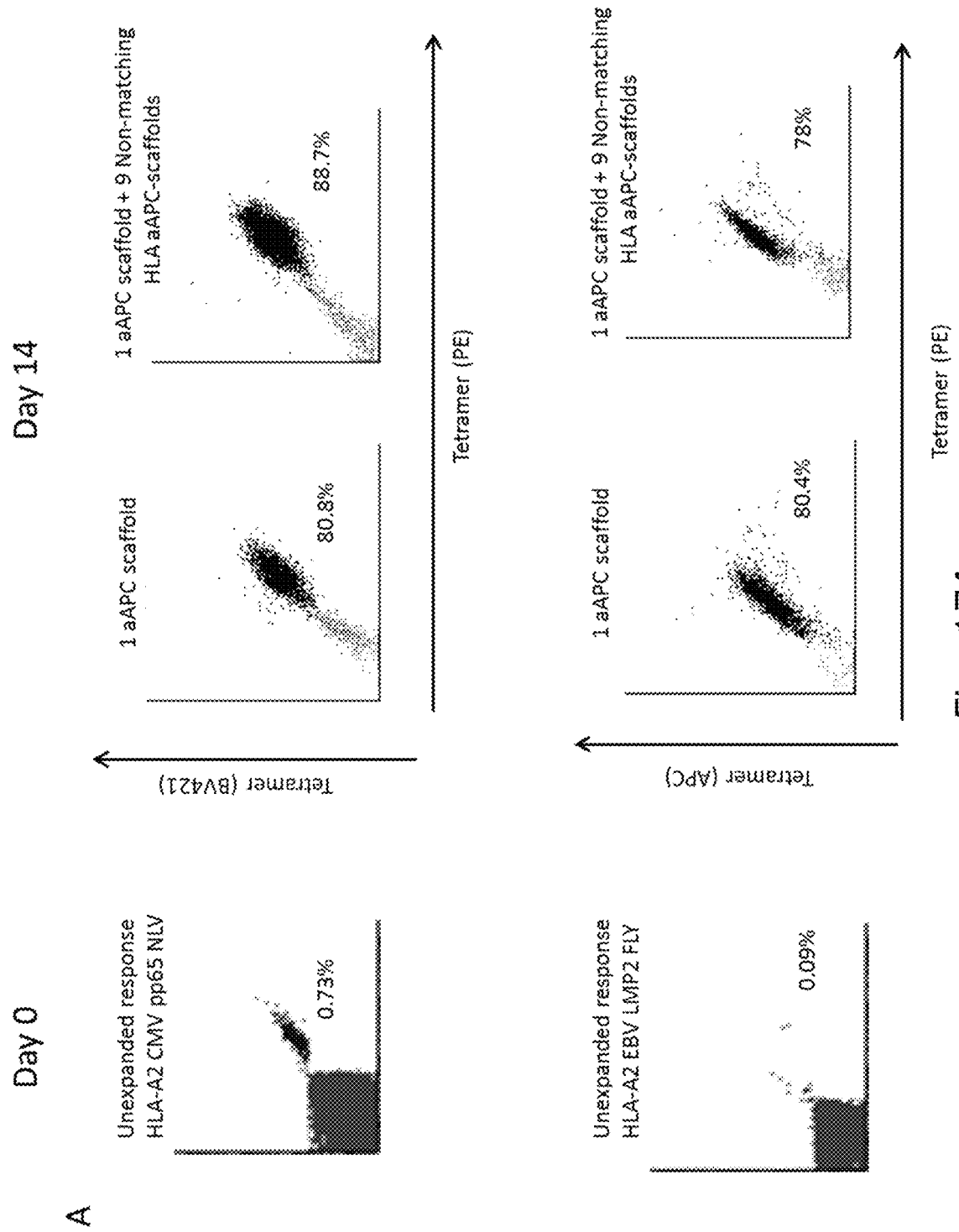

In FIG. 17A, two cultures were established to individually expand HLA-A2 EBV LMP2 FLY and HLA-A2 CMV pp65 NLV specific CD8 T cells, respectively, essentially as done in example 1. These two cultures were respectively compared to two cultures where HLA-A2 EBV LMP2 FLY and HLA-A2 CMV pp65 NLV specific CD8 T cells were also individually expanded, respectively, though using ¹⁄₁₀ of the normal aAPC scaffold concentration plus ⁹⁄₁₀ concentration of aAPC scaffolds with non-matching HLA-types.

Figure 17B:
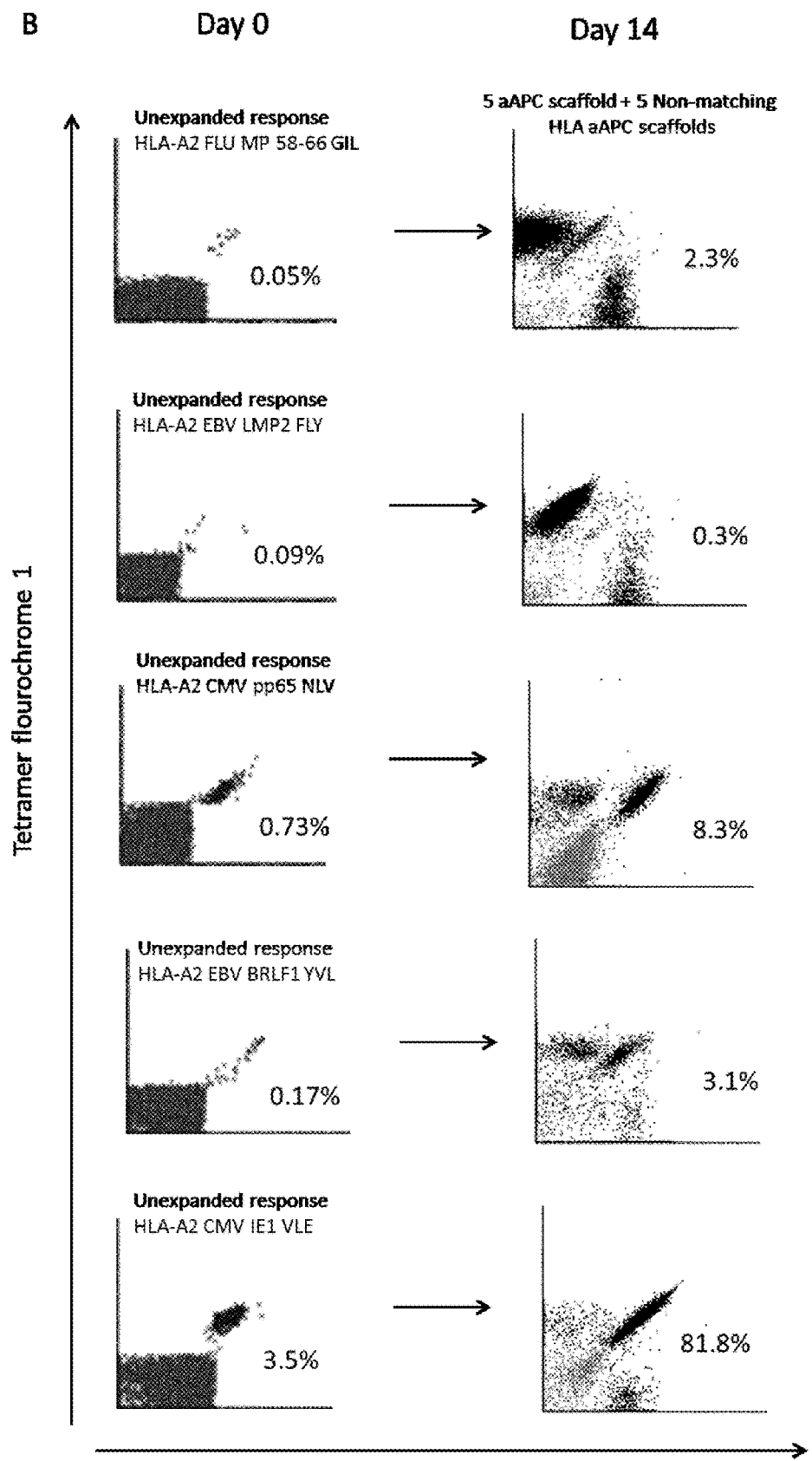

In FIG. 17B, material from one healthy donor containing five known virus responses was used as the starting material to simultaneously expand all five antigen specificities in one single culture. This was essentially done as in example 1 using ¹⁄₁₀ of the aAPC scaffold 1:8:8:8 (scaffold:pMHC:IL-2:IL-21) concentration used in example 1 of the five antigen specificities respectively, plus ⁵⁄₁₀ of aAPC scaffolds with non-matching HLA-type. The frequency of antigen specific T cells for each of the five specificities was measured at day 0 (baseline) and after 14 days expansion using MHC tetramers. The specificity of the five virus responses are respectively, HLA-A2 FLU MP 58-66 GIL, HLA-A2 EBV LMP2 FLY, HLA-A2 CMV pp65 NLV, HLA-A2 EBV BRLF1 YVL, and HLA-A2 CMV IE1 VLE.

Conclusion:

(FIG. 17A-B) From example 11 it can be concluded that antigen-specific T cells (HLA-A2 EBV LMP2 FLY and HLA-A2 CMV pp65 NLV specific CD8 T cells) can be efficiently expanded when using ¹⁄₁₀ of the aAPC scaffold concentration used in example 1, plus ⁹⁄₁₀ of aAPC scaffolds with irrelevant non-matching HLA-type (FIG. 17A). It can also be concluded that five different virus responses from a single donor material can be efficiently expanded in parallel in a single culture by applying multiple aAPC scaffold specificities simultaneously (FIG. 17B).

Example 12: Expansion of Antigen-Specific T Cells with aAPC Scaffolds of Different Size and Stoichiometry of Scaffold, pMHC and Cytokines (FIG. 18A-B)

Antigen-specific CD8 T cells from a healthy donor were expanded in six parallel cultures essentially as in example 1 and the frequency of T cells with the given antigen specificity was measured after 2 weeks expansion using MHC multimers. Scaffolds of MW 250 KDa, 750 KDa, and 2000 KDa each tested with two different scaffold to molecule ratios were used. (A) aAPC scaffold 1:8:8:8 (scaffold:pMHC:IL-2:IL-21), and (B) aAPC scaffold 1:24:24:24 (scaffold:pMHC:IL-2:IL-21).

Conclusion:

(FIG. 18A-B) From example 12 it can be concluded that antigen-specific CD8 T cells can be efficiently expanded with scaffolds of different MW, such as 250 KDa, 750 KDa, and 2000 KDa and scaffold:pMHC:IL-2:IL-21 ratios of 1:8:8:8 (FIG. 18A) and 1:24:24:24 (FIG. 18B) for all scaffold sizes.

Example 13: In Vivo Expansion of OVA-Specific CD8 T Cells in C57BL/6 Mice Using aAPC Scaffolds (FIG. 19)

Four C57BL/6 mice were vaccinated with ovalbumin (OVA) and polyIC to establish an antigen-specific T cell response restricted towards the C57BL/6 allele H2-Kb presenting the OVA derived peptide SIINFEKL (SEQ ID NO:1). The frequency of OVA-specific CD8 T cells were measured pre vaccination, on day 7 and day 19 after i.p. vaccination with OVA+poly IC and day 7 after booster (day 28) using H2-Kb/SIINFEKL tetramers. Four different boosters were administrated on day 21 post vaccination. Mouse 1 had PBS i.v., mouse 2 had OVA i.p., mouse 3 had aAPC scaffold 1:8:8:8 with the H2-Kb/SIINFEKL (scaffold:

pMHC:IL-2:IL21) i.v., and mouse 4 had H2-Kb/SIINFEKL in the same concentration as assembled on the aAPC scaffold 1:8:8:8 i.v. (i.e. the booster for mouse 3). I.e. in mouse 4, the antigenic peptide was given as part of a pMHC complex, but without the aAPC scaffold.

Conclusion:

(FIG. 19) Example 13 demonstrates that aAPC scaffolds can be applied in vivo, that such application is safe (no toxicities observed) and the aAPCs efficiently expand an antigen-specific T cell response in vivo (FIG. 19).

Example 14: Comparison of Expansion of Antigen-Specific CD8 T Cells Using aAPC Scaffold Versus Peptide Pulsed Monocyte Derived Dendritic Cells (FIG. 20A-D)

Dendritic cells were generated from autologous PBMC's from an HLA-A0201 CMV positive donor using PromoCell's Dendritic Cell Generation protocol and Media, which promote in vitro maturation of human Monocytes (hMo) into mature CD83+ monocyte-derived Dendritic Cells (moDCs). Monocytes were differentiated into moDCs, using a combination of PromoCell Monocyte Attachment Medium (C-28051) and the PromoCell Dendritic Cell Generation Medium (C-28050). Briefly, PBMC's in PromoCell Monocyte Attachment Medium were plated out in tissue culture plates at a density of 2-3 million/cm2 for 1 hour at 5% CO2 and 37° C. Monocytes were capture by removing non-adherent cells. Differentiation into immature moDC (day 0) was started by adding PromoCell Dendritic Cell Generation Medium supplemented with 1× Component A of the Cytokine Pack moDC (supplied at 100×) and incubation for 3 days at 37° C. and 5% CO2. Medium change was performed on day 3 by aspirating the medium from the cells and adding fresh PromoCell DC Generation Medium supplemented with 1× Component A of the Cytokine Pack moDC to the cells. The moDC maturation process was completed by supplementing the whole volume with 1× of Component B of the Cytokine Pack moDC (supplied at 100×) on day 6 and incubated at 37° C. and 5% CO2 for an additional 40 hours. moDC's were counted by Trypan Blue staining.

Peptide pulsed moDC's were generated by suspending 37.500 cells/mL in X-VIVO media containing 50 µg/ml peptide (CMV pp65 NLVPMVATV (SEQ ID NO:2)) and incubated for 4 hours at 37° C. After incubation, cells were washed once in X-VIVO media and suspended in 50 µL X-VIVO+5%.

HLA-A201/CMV pp65 NLVPMVATV peptide specific T cells were expanded from 100.000 PBMC's from a healthy donor with initially 0.01% HLA-A201/CMV pp65 NLVPMVATV positive T cells. The expansion was done under four conditions in parallel in the presence of either (A) free MHC complex (HLA-A201/NLVPMVATV) and IL2 and IL21, (B) aAPC scaffold with the ratio 1:8:8:8 (HLA-A201/NLVPMVATV) (scaffold:pMHC:IL-2:IL-21), (C) 37.500 unpulsed moDC's derived from the same donor supplemented with IL-7 to a final concentration of 120 U/ml (day one) and IL-12 to a final concentration of 120 U/ml (day 2) or (D) 37.500 NLVPMVATV peptide pulsed moDC's derived from the same donor supplemented with IL-7 to a final concentration of 120 U/ml (day one) and IL-12 to a final concentration of 120 U/ml (day 2). All conditions were cultured for 2 weeks in X-VIVO media supplemented with 5% human serum. The expansion of HLA-A201/CMV pp65 NLVPMVATV peptide specific T cells was traced by MHC tetramer staining after two weeks. Representative dot plots are shown in FIG. 20.

Conclusion:

(FIG. 20) Example 14 demonstrates that expansion of antigen-specific CD8 T cells using aAPC scaffold is significantly (approximately a factor of 2) more efficient (FIG. 20B, 5.5%, 550 fold expansion) for expansion of antigen-specific T cells as compared to using peptide pulsed moDC (FIG. 20D, 2.8%, 280 fold expansion).

REFERENCES

WO2002072631
WO2009003492
WO2009094273

Items

The invention will now be described in further details in the following non-limiting items.

Item 1. An artificial antigen presenting cell (aAPC) scaffold comprising a polymeric backbone to which are attached the following template molecules:
  i. at least one major histocompatibility complex molecule comprising an antigenic peptide (pMHC),
  ii. at least one cytokine selected from the group consisting of IL-21, IL-2, IL-15, IL-1, IL-6, IL-10 and IL-7,
  iii. optionally, at least one co-stimulatory molecule selected from the group consisting of B7.2 (CD86), B7.1 (CD80), CD40, ICOS and PD-L1, and
  iv. optionally, at least one CD47 molecule.

Item 2. The aAPC scaffold according to item 1, wherein the template molecules comprise at least two different cytokines selected from the group consisting of IL-21, IL-2, IL-15, IL-1, IL-6, IL-10 and IL-7.

Item 3. The aAPC scaffold according to item 1 or 2, wherein the template molecules are attached to the polymeric backbone via non-covalent interactions between a coupling agent located on the polymeric backbone and an affinity tag on the template molecule.

Item 4. The aAPC scaffold according to item 3, wherein the coupling agent is streptavidin and the affinity tag is biotin.

Item 5. The aAPC scaffold according to any one of the preceding items, wherein the polymeric backbone is selected from the group consisting of polysaccharides, vinyl polymers, poly ethylene glycol, poly propylene glycol, streptactin and poly-streptavidin.

Item 6. The aAPC scaffold according to any one of the preceding items, wherein the polymeric backbone is a polysaccharide.

Item 7. The aAPC scaffold according to items 5 or 6, wherein the polysaccharide is dextran.

Item 8. The aAPC scaffold according to item 7, wherein the dextran has a molecular weight in the range of 50-3000 kDa, such as 100-2500 kDa, such as 250-2500 kDa.

Item 9. The aAPC scaffold according to items 7 or 8, wherein the dextran has a molecular weight selected from the group of consisting of 250 kDa, 270 kDa, 750 kDa, and 2000 kDa.

Item 10. The aAPC scaffold according to any one of the preceding items, wherein the at least one pMHC molecule is a vertebrate MHC molecule, such as a human, murine, rat, porcine, bovine or avian molecule.

Item 11. The aAPC scaffold according to item 10, wherein the vertebrate MHC molecule is a human molecule.

Item 12. The aAPC scaffold according to any one of the preceding items, wherein the at least one pMHC molecule is selected from the group consisting of MHC class I molecules, MHC class II molecules, MHC class III molecules, CD1a, CD1b, CD1c, CD1d and MR1.

Item 13. The aAPC scaffold according to item 12, wherein the at least one pMHC molecule is a MHC class I molecule.

Item 14. The aAPC scaffold according to any one of the preceding items, wherein the antigenic peptide of the pMHC is a cancer-associated epitope or virus epitope.

Item 15. The aAPC scaffold according to item 14, wherein the cancer-associated epitope is a virus epitope associated with a virus-induced cancer.

Item 16. The aAPC scaffold according to item 14 or 15, wherein the virus epitope is from a virus selected from the group consisting of human papillomavirus (HPV), Merkel cell polyomavirus (MCV), cytomegalovirus (CMV), Epstein-Barr virus (EBV), human T-lymphotropic virus (HTLV), hepatitis B virus (HBV), hepatitis C virus (HCV) and influenza virus.

Item 17. The aAPC scaffold according to any one of the preceding items, wherein the pMHC molecules are identical and present only a single variant of an antigenic peptide.

Item 18. The aAPC scaffold according to any one of the preceding items, wherein each polymeric backbone comprises at least 5 pMHC molecules, such as at least 8, such as at least 10, such as at least 20, such as at least 30, such as at least 40, such as at least 50 or such as at least 100.

Item 19. The aAPC scaffold according to any one of the preceding items, wherein said aAPC scaffold is immobilized on a solid support.

Item 20. The aAPC scaffold according to item 19, wherein the solid support is selected from the group consisting of beads, well plates, particles, micro arrays and membranes.

Item 21. The aAPC scaffold according to any one of the preceding items, wherein the template molecules comprise at least IL-21.

Item 22. The aAPC scaffold according to any one of the preceding items, wherein the template molecules comprise at least IL-15 and IL-21.

Item 23. The aAPC scaffold according to any one of the preceding items, wherein the template molecules comprise at least B7.2 (CD86).

Item 24. The aAPC scaffold according to any one of the preceding items, wherein
  i. the polymeric backbone is dextran,
  ii. the co-stimulatory molecule is B7.2 (CD86), and
  iii. the cytokines are IL-15 and IL-21.

Item 25. The aAPC scaffold according to item 24, wherein the ratio between pMHC, IL-15, IL-21 and B7.2 (CD86) on the dextran backbone is 2:1:1:1.

Item 26. The aAPC scaffold according to any one of items 24 or 25, wherein the ratio between dextran backbone, pMHC, IL-15, IL-21 and B7.2 (CD86) is 1:10:5:5:5.

Item 27. The aAPC scaffold according to any one of items 1-20, wherein the template molecules comprise at least IL-6 and IL-10.

Item 28. The aAPC scaffold according to item 27, wherein
  i. the polymeric backbone is dextran,
  ii. the co-stimulatory molecule is B7.2 (CD86), and
  iii. the cytokines are IL-6 and IL-10.

Item 29. The aAPC scaffold according to item 28, wherein the ratio between pMHC, IL-6, IL-10 and B7.2 (CD86) on the dextran backbone is 2:1:1:1.

Item 30. The aAPC scaffold according to any one of items 28 or 29, wherein the ratio between dextran backbone, pMHC, IL-6, IL-10 and B7.2 (CD86) is 1:10:5:5:5.

Item 31. The aAPC scaffold according to any one of items 1-21, wherein
  i. the polymeric backbone is dextran, and
  ii. the cytokines are IL-2 and IL-21.

Item 32. The aAPC scaffold according to item 31, wherein the ratio between pMHC, IL-2 and IL-21 on the dextran backbone is 1:1:1.

Item 33. The aAPC scaffold according to any one of items 31 or 32, wherein the ratio between dextran backbone, pMHC, IL-2 and IL-21 is 1:8:8:8.

Item 34. The aAPC scaffold according to item 1, wherein the polymeric backbone comprises at least IL-1 and PD-L1.

Item 35. The aAPC scaffold according to item 34, wherein
  i. the polymeric backbone is dextran,
  ii. the co-stimulatory molecules are B7.2 (CD86) and PD-L1, and
  iii. the cytokine is IL-1.

Item 36. The aAPC scaffold according to item 35, wherein the ratio between pMHC, IL-1, B7.2 (CD86) and PD-L1 on the dextran backbone is 2:1:1:1.

Item 37. The aAPC scaffold according to any one of items 35 or 36, wherein the ratio between dextran backbone, pMHC, IL-1, B7.2 (CD86) and PD-L1 is 1:10:5:5:5.

Item 38. A method for simultaneous in vitro stimulation and expansion of T cells, comprising the following steps:
  i. providing a sample comprising T cells,
  ii. contacting said sample with a solution comprising an aAPC scaffold according to any one of the preceding items,
  iii. stimulating and expanding T cells with specificity for said aAPC scaffold in culture, and
  iv. harvesting the T cells of step iii) from the culture to obtain an expanded antigen-specific population of T cells.

Item 39. The method according to item 38, wherein the solution comprising an aAPC scaffold of step ii) has been filtered before contact with the sample.

Item 40. The method according to item 39, wherein the solution comprising an aAPC scaffold is filtered by centrifugation through molecular weight cut-off filters.

Item 41. The method according to any one of items 38-40, wherein said sample of step i) comprises T-cells of at least 2 different specificities, such as at least 5 different specificities, such as at least 10 different specificities, such as at least 15 different specificities, such as at least 20 different specificities, or such as at least 50 different specificities.

Item 42. The method according to any one of items 38-41, wherein said solution comprising an aAPC scaffold comprises at least 2 different aAPC scaffolds, such as at least 5 different aAPC scaffolds, such as at least 10 different aAPC scaffolds, such as at least 15 different aAPC scaffolds, such as at least 20 different aAPC scaffolds, or such as at least 20 different aAPC scaffolds.

Item 43. The method according to any one of items 38-42, wherein T-cells of at least 2 different specificities are stimulated and expanded in parallel in the same sample, such as at least 5 different specificities, such as at least 10 different specificities, such as at least 15 different specificities, or such as at least 20 different specificities.

Item 44. The method according to any one of items 38-43, wherein the method comprises the following steps:
  i. providing a sample comprising T cells with at least 5 different specificities,
  ii. contacting said sample with a solution comprising at least 5 different aAPC scaffolds,
  iii. parallel stimulation and expansion of said T cells with at least 5 different specificities for said at least 5 different aAPC scaffolds in culture, and iv. harvesting the T cells of step iii) from the culture to obtain an expanded antigen-specific population of T cells with at least 5 different specificities.

Item 45. The method according to any one of items 38-44, wherein the sample is selected from the group consisting of peripheral blood mononuclear cells, tumors, tissue, bone marrow, biopsies, serum, blood, plasma, saliva, lymph fluid, pleura fluid, cerospinal fluid and synovial fluid.

Item 46. The method according to any one of items 38-47, wherein the T cells are selected from the group consisting of CD8 T cells, CD4 T cells, regulatory T cells, natural killer T (NKT) cells, gamma-delta T cells and innate mucosal-associated invariant T (MAIT) cells.

Item 47. The method according to any one of items 38-46, wherein the T cells are CD8 T cells.

Item 48. The method according to any one of items 38-47, wherein the T cells are expanded to a clinically relevant number.

Item 49. The method according to any one of items 38-48, wherein the antigenic peptide of the pMHC is a cancer-associated epitope or virus epitope.

Item 50. The method according to item 49, wherein the cancer-associated epitope is a virus epitope associated with a virus-induced cancer.

Item 51. The method according to item 49 or 50, wherein the virus epitope is from a virus selected from the group consisting of human papillomavirus (HPV), Merkel cell polyomavirus (MCV), cytomegalovirus (CMV), Epstein-Barr virus (EBV), human T-lymphotropic virus (HTLV), hepatitis B virus (HBV), hepatitis C virus (HCV) and influenza virus.

Item 52. An expanded T cell population obtained by the method according to any one of items 38-51.

Item 53. An expanded T-cell population obtained by the method according to any one of items 38-51 for use as a medicament.

Item 54. An expanded T-cell population obtained by the method according to any one of items 38-51 for use in the treatment of a cancer or viral condition.

Item 55. The expanded T-cell population for use according to item 54, wherein the cancer is associated with a viral condition.

Item 56. The expanded T-cell population for use according to item 54 or 55, wherein the viral condition is associated with a virus selected from the group consisting of human papillomavirus (HPV), Merkel cell polyomavirus (MCV), cytomegalovirus (CMV), Epstein-Barr virus (EBV), human T-lymphotropic virus (HTLV), hepatitis B virus (HBV), hepatitis C virus (HCV) and influenza virus.

The invention claimed is:

1. An artificial antigen presenting cell (aAPC) scaffold comprising a polymeric backbone to which are attached the following template molecules:
   i. at least two different gamma-chain receptor cytokines selected from the group consisting of IL-21, IL-2, IL-15, IL-4, IL-9, and IL-7, and
   ii. at least one antigen,
   wherein the polymeric backbone is soluble and non-magnetic and wherein the at least two different gamma-chain receptor cytokines comprise at least IL-21.

2. The aAPC scaffold according to claim 1, wherein the at least two gamma-chain receptor cytokines are selected from the group consisting of IL-21, IL-2, and IL-15.

3. The aAPC scaffold according to claim 1, wherein the at least two gamma-chain receptor cytokines comprise:
   i. at least IL-2 and IL-21, or
   ii. at least IL-15 and IL-21.

4. The aAPC scaffold according to claim 1, wherein the at least one antigen is a major histocompatibility complex molecule comprising an antigenic peptide (pMHC).

5. The aAPC scaffold according to claim 4, wherein each polymeric backbone comprises at least 5 pMHC molecules.

6. The aAPC scaffold according to claim 4, wherein the antigen comprises a cancer-associated epitope or virus epitope.

7. The aAPC scaffold according to claim 6, wherein the virus epitope is from a virus selected from the group consisting of human papillomavirus (HPV), Merkel cell polyomavirus (MCV), cytomegalovirus (CMV), Epstein-Barr virus (EBV), human T-lymphotropic virus (HTLV), hepatitis B virus (HBV), hepatitis C virus (HCV) and influenza virus.

8. The aAPC scaffold according to claim 1, wherein the polymeric backbone is a polysaccharide.

9. The aAPC scaffold according to claim 1, wherein:
  i. the polymeric backbone is dextran,
  ii. the gamma-chain receptor cytokines are IL-2 and IL-21, and
  iii. the antigen is a major histocompatibility complex molecule comprising an antigenic peptide (pMHC).

10. The aAPC scaffold according to claim 1, wherein the co-stimulatory molecules comprise at least B7.2 (CD86).

11. The aAPC scaffold according to claim 1, wherein the template molecules comprise at least one CD47 molecule.

12. The aAPC scaffold according to claim 1, wherein the template molecules are attached to the polymeric backbone via non-covalent interactions between a coupling agent located on the polymeric backbone and an affinity tag on the template molecule.

13. A method for simultaneous in vitro stimulation and expansion of T cells, comprising:
  i. providing a sample comprising T cells,
  ii. contacting said sample with a solution comprising an aAPC scaffold according to claim 1,
  iii. stimulating and expanding T cells with specificity for said aAPC scaffold in culture, and
  iv. harvesting the T cells of step iii) from the culture to obtain an expanded antigen-specific population of T cells.

14. The method according to claim 13, wherein T-cells of at least 2 different specificities are stimulated and expanded in parallel in the same sample.

15. The method according to claim 13, wherein the method comprises:
  i. providing a sample comprising T cells with at least 5 different specificities,
  ii. contacting said sample with a solution comprising at least 5 different aAPC scaffolds,
  iii. parallel stimulation and expansion of said T cells with at least 5 different specificities for said at least 5 different aAPC scaffolds in culture, and
  iv. harvesting the T cells of step iii) from the culture to obtain an expanded antigen-specific population of T cells with at least 5 different specificities.

16. The method according to claim 13, wherein the antigen comprises a cancer-associated epitope or virus epitope.

17. The aAPC scaffold according to claim 1, wherein the following template molecules are further attached to the polymeric backbone:
  i. at least one co-stimulatory molecule selected from the group consisting of B7.2 (CD86), B7.1 (CD80), CD40, ICOS, PD-L1, and/or
  ii. at least one CD47 molecule.

18. The aAPC scaffold according to claim 1, wherein a concentration of each of the gamma-chain receptor cytokines is below about 4.8 nM.

* * * * *

SEQUENCE LISTING

```
<160> NUMBER OF SEQ ID NOS: 2

<210> SEQ ID NO 1
<211> LENGTH: 8
<212> TYPE: PRT
<213> ORGANISM: Mus musculus

<400> SEQUENCE: 1

Ser Ile Ile Asn Phe Glu Lys Leu
1               5

<210> SEQ ID NO 2
<211> LENGTH: 9
<212> TYPE: PRT
<213> ORGANISM: Cytomegalovirus

<400> SEQUENCE: 2

Asn Leu Val Pro Met Val Ala Thr Val
1               5
```